United States Patent [19]

Brown et al.

[11] Patent Number: 5,502,065
[45] Date of Patent: Mar. 26, 1996

[54] INDOLE DERIVATIVES AS 5-HT$_1$-LIKE AGONISTS

[75] Inventors: Alan D. Brown; Roger P. Dickinson; Martin J. Wythes, all of Sandwich, United Kingdom

[73] Assignee: Pfizer Inc., New York, N.Y.

[21] Appl. No.: 307,566

[22] PCT Filed: Apr. 8, 1993

[86] PCT No.: PCT/EP93/00867

§ 371 Date: Sep. 21, 1994

§ 102(e) Date: Sep. 21, 1994

[87] PCT Pub. No.: WO93/21178

PCT Pub. Date: Oct. 28, 1993

[30] Foreign Application Priority Data

Apr. 14, 1992 [GB] United Kingdom ............... 9208161

[51] Int. Cl.$^6$ .................. A61K 31/44; C07D 209/04; C07D 213/04
[52] U.S. Cl. .................. 514/339; 514/323; 514/414; 548/402; 548/405; 548/406; 548/466; 548/469; 546/2; 546/9; 546/13; 546/14; 546/192; 546/193; 546/194; 546/201; 546/273; 544/225; 544/226; 544/229; 544/238; 544/297; 544/298; 544/322; 544/331; 544/333; 544/405
[58] Field of Search ................ 548/466, 469, 548/402, 405, 406; 546/192, 193, 194, 201, 273, 2, 9, 13, 14; 544/238, 297, 298, 322, 331, 333, 405, 225, 226, 229; 514/323, 414, 339

[56] References Cited

FOREIGN PATENT DOCUMENTS

| 0438230 | 7/1991 | European Pat. Off. . |
| 9206973 | 8/1988 | WIPO ................... 548/466 |
| 9118897 | 10/1988 | WIPO ................... 548/466 |

OTHER PUBLICATIONS

CA119:249833a Indole . . . Antagonist, Macor et al. p. 970, 1993.

A. R. Martin, et al., QSAR Studies of 5–Substituted–3–(1, 2,3,6–Tetrahydropyridin–4–yl)–1H–indoles at Serotonin Binding Sites, *8th Camerino—Noordwijkerhout Symposium*, Sep. 8–12, 1991.

A. R. Martin, et al., Preparation of 5–Substituted Indoles via Halogen–Metal Exchange and Palladium Catlayzed Cross Coupling Strategies, *13th International Congress of Heterocyclic Chemisty*, Aug. 11–16, 1991.

Y. Yang, et al., *Heterocycles*, 34 (b), 1169 (1992), Synthesis of Some 5–Substituted Indoles.

*Primary Examiner*—Joseph K. McKane
*Attorney, Agent, or Firm*—Peter C. Richardson; Paul H. Ginsburg; Grover F. Fuller, Jr.

[57] ABSTRACT

The present invention provides compounds of the formula:

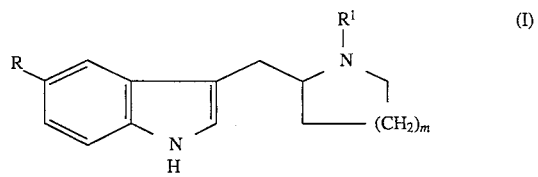

and pharmaceutically acceptable salts thereof.

11 Claims, No Drawings

INDOLE DERIVATIVES AS 5-HT$_1$-LIKE AGONISTS

The present invention relates to indole derivatives which act on 5-hydroxytryptamine (5-HT) receptors.

More particularly the present invention relates to 3,5-disubstituted indoles which are selective agonists at the "5-HT$_1$-like" subtype of the 5-hydroxytryptamine receptor. Such "5-HT$_1$-like" receptors are present in the carotid vascular bed and their activation causes vasoconstriction with a consequent reduction in carotid blood flow. Compounds which have "5-HT$_1$-like" agonist activity are therefore useful in the treatment of medical conditions which are thought to result from excessive dilation of the carotid bed such as migraine, cluster headache, chronic paroxysmal hemicrania and headache associated with vascular disorders. Certain compounds of the present invention are also agonists at central 5-HT$_1$ receptors and are therefore useful for the treatment of depression, anxiety, eating disorders, obesity and drug abuse.

The present invention provides compounds of the formula:

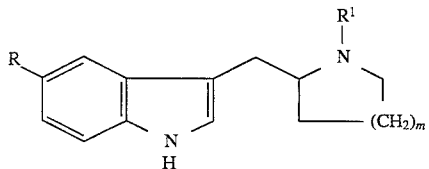

(I)

and pharmaceutically acceptable salts thereof, wherein R is phenyl, pyridinyl, pyridazinyl, pyrimidinyl, pyrazinyl, furyl or thienyl, all of which may be optionally substituted by halo, $C_1$–$C_4$ alkyl, $C_1$–$C_4$ alkoxy or a group of the formula:

—X—R$^2$;

R$^1$ is H, $C_1$–$C_6$ alkyl, $C_3$–$C_7$ cycloalkyl, $C_5$–$C_7$ cycloalkenyl, $C_3$–$C_6$ alkenyl or $C_1$–$C_6$ alkynyl, said alkyl group being optionally substituted by $C_3$–$C_7$ cycloalkyl, $C_3$–$C_7$ cycloalkyloxy, OH, $C_1$–$C_6$ alkoxy, CONR$^3$R$^4$, SO$_2$NR$^3$R$^4$, COR$^5$, SOR$^5$, SO$_2$R$^5$, CO$_2$R$^6$, aryl, aryloxy, aryl($C_1$–$C_6$)alkoxy or heteroaryl, said alkenyl group being optionally substituted by aryl and said cycloalkyl group being optionally substituted by OH; the cycloalkyl and cycloalkenyl groups being optionally linked to the N-atom by a $C_1$–$C_2$ alkylene moiety;

R$^2$ is COR$^7$, CO$_2$R$^7$, SOR$^7$, SO$_2$R$^7$, CONR$^3$R$^4$, SO$_2$NR$^3$R$^4$, NHCOR$^7$, NHCONR$^3$R$^4$, NHSO$_2$R$^7$, NHSO$_2$NR$^3$R$^4$, OH or CN;

R$^3$ and R$^4$ are either each independently selected from H, $C_3$–$C_7$ cycloalkyl and $C_1$–$C_6$ alkyl, said alkyl group being optionally substituted by $C_3$–$C_7$ cycloalkyl or aryl, or R$^3$ and R$^4$ taken together represent $C_3$–$C_6$ alkylene optionally interrupted by O, S(O)$_n$, NH or N($C_1$–$C_6$ alkyl);

R$^5$ is $C_1$–$C_6$ alkyl, $C_3$–$C_7$ cycloalkyl, $C_3$–$C_7$ cycloalkyl($C_1$–$C_6$)alkylene, aryl($C_1$–$C_6$)alkylene, or aryl;

R$^6$ is $C_1$–$C_6$ alkyl, $C_3$–$C_7$ cycloalkyl or aryl($C_1$–$C_6$)alkylene;

R$^7$ is $C_1$–$C_6$ alkyl;

X is a direct link or $C_1$–$C_7$ alkylene;

m is 1 or 2; and n is 0, 1 or 2.

"aryl" for substituents other than R means phenyl optionally substituted by $C_1$–$C_6$ alkyl, $C_1$–$C_6$ alkoxy or halo; and "heteroaryl" for substituents other than R means pyridinyl, pyrimidinyl, pyrazinyl, furyl, thienyl, pyrrolyl, thiazolyl or oxazolyl.

Alkyl, alkoxy and alkenyl groups having three or more carbon atoms, and alkynyl groups having four or more carbon atoms, can be straight- or branched-chain.

Halo means fluoro, chloro, bromo or iodo.

When R is phenyl, it is preferably substituted phenyl, the substituents being preferably at the 3- or 4-position of the ring.

A preferred groups of compounds of formula (I) is that wherein R$^1$ is (R$^5$CO)$C_1$–$C_2$ alkylene; (RO$_2$C)$C_1$–$C_2$ alkylene; (R$^3$R$^4$NOC)$C_1$–$C_2$ alkylene; R$^3$R$^4$NO$_2$SCH$_2$CH$_2$; R$^3$NSO$_2$ $C_1$–$C_2$ alkylene; R$^3$SOC$_1$–$C_2$ alkylene; R$^3$SO$_2$C$_1$–$C_2$ alkylene; (R$^5$O)C$_2$–$C_3$ alkylene; ($C_3$–$C_7$ cycloalkyl)CH$_2$; (phenyl)C$_1$–$C_2$ alkylene; (pyridyl)C$_1$–$C_2$ alkylene; $C_5$–$C_6$ cycloalkyl optionally substituted with HO; $C_3$–$C_5$ alkenyl optionally substituted with phenyl; or cyclohexenyl;

Preferably R$^1$ is $C_1$–$C_6$ alkyl. Most preferably it is H or CH$_3$.

Preferably R$^3$ and R$^4$ are either each independently selected from H and $C_1$–$C_4$ alkyl, or R$^3$ and R$^4$ taken together represent $C_3$–$C_6$ alkylene interrupted by O.

Most preferably R$^3$ and R$^4$ are either each independently selected from H, or $C_1$–$C_4$ alkyl, or R$^3$ and R$^4$ taken together with the nitrogen atom to which they are attached represent morpholino.

Preferably R$^7$ is methyl, ethyl or n-propyl.

Preferably X is a direct link or methylene.

Preferably m is 1.

In a further aspect, therefore, the invention provides compounds of formula (I) wherein:

R is substituted phenyl, pyridinyl, pyrimidinyl, thienyl or furyl, each optionally substituted by a group of the formula:

—X—R$^2$;

R$^1$ is H, $C_1$–$C_6$ alkyl, $C_1$–$C_4$ alkoxy($C_1$–$C_6$)alkylene, R$^4$R$^3$NCO($C_1$–$C_6$)alkylene, or $C_3$–$C_6$ cycloalkyl($C_1$–$C_4$)alkylene;

R$^2$ is COR$^7$, CO$_2$R$^7$, SOR$^7$, SO$_2$R$^7$, CONR$^3$R$^4$, SO$_2$NR$^3$R$^4$, NHSO$_2$R$^7$, CN or OH;

R$^3$ and R$^4$ are either each independently selected from H and $C_1$–$C_4$ alkyl, or R$^3$ and R$^4$ taken together represent $C_3$–$C_6$ alkylene interrupted by O;

R$^7$ is methyl, ethyl or n-propyl;

X is a direct link or methylene; and m is 1.

In an even more preferred aspect the invention provides compounds of formula I wherein R is phenyl optionally substituted at the 3-or 4-position, or 2-, 3- or 4-pyridinyl optionally substituted at the 5- or 6-position, both optionally substituted with sulphamoyl, N,N-dimethylsulphamoyl, carbamoyl, N-methylcarbamoyl, N,N-dimethylcarbamoyl, morpholinocarbonyl, methyl- or ethyl- or n-propylsulphonyl or -sulphinyl, methyl- or ethyl-sulphonylmethyl, acetyl, hydroxymethyl, methoxycarbonyl, ethanesulphonamidomethyl, cyano, carbamoylmethyl, 1-hydroxyprop-2-yl, N,N-dimethylcarbamoylmethyl, ethylcarbamoyl, dimethylcarbamoyl or methoxycarbonyl; R$^1$ is hydrogen, methyl, ethyl, 2-methoxyethyl, cyclopropylmethyl, benzyloxycarbonyl, 2-carbamoylethyl, 2-dimethylcarbamoylethyl; and m is 1.

The preferred compounds of the formula (I) have the R-configuration at the 2-position of the pyrrolidine or piperidine ring, i.e.

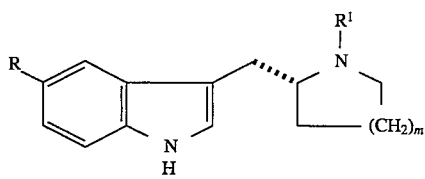

Preferred compounds of the invention include the following:

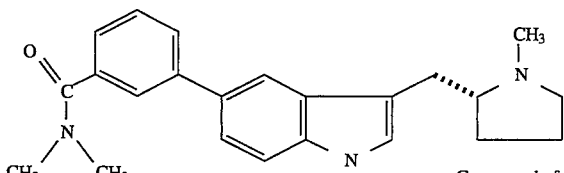

Compound of Example 13;

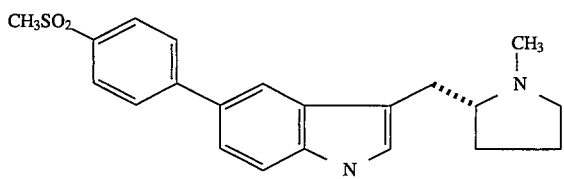

Compound of Example 1;

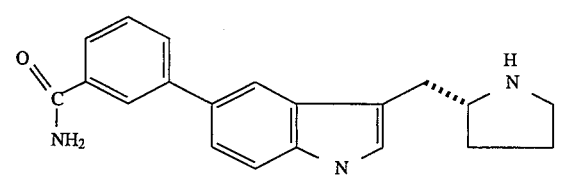

Compound of Example 38;

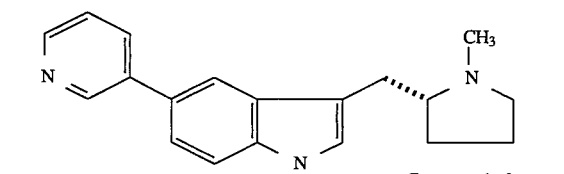

Compound of Example 56; and

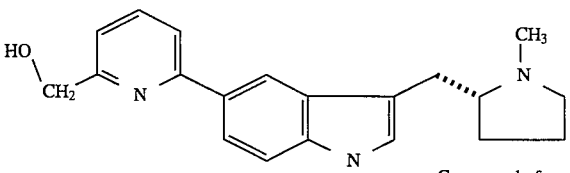

Compound of Example 63

The pharmaceutically acceptable salts of the compounds of the formula (I) include acid addition salts formed with acids which form nontoxic salts such as the hydrochloride, hydrobromide, hydroiodide, sulphate, bisulphate, phosphate, hydrogen phosphate, acetate, maleate, fumarate, lactate, tartrate, citrate, gluconate, benzoate, methanesulphonate, benzenesulphonate and para-toluenesulphonate salts. For a review on suitable pharmaceutical salts see Berge et al, J. Pharm. Sci., 66, 1–19 (1977).

The compounds of the formula (I) contain at least one chiral centre and therefore exist as at least one pair of enantiomers. The invention includes both the individual stereoisomers of the compounds of the formula (I) together with mixtures thereof. Separation of diastereoisomers may be achieved by conventional techniques, e.g. by fractional cystallisation, chromatography or H.P.L.C. of a diastereoisomeric mixture of a compound of the formula (I) or a suitable salt or derivative thereof. An individual enantiomer of a compound of the formula (I) may also be prepared from a corresponding optically pure intermediate or by resolution, either by H.P.L.C. of the racemate using a suitable chiral support or by fractional crystallisation of the diastereoisomeric salts formed by reaction of the racemate with a suitable optically active acid.

Certain compounds of the formula (I) can exist in different tautomeric forms. The invention includes the different tautomeric forms where appropriate.

The compounds of the formula (I) which are provided by the present invention can be prepared by the following methods:

1) All compounds of the formula (I) can be prepared by palladium-catalysed cross-coupling of a compound of the formula:

$$RM \qquad (II)$$

wherein R is as defined above for a compound of formula (I) and M is an optionally substituted metal substituent suitable for cross-coupling reactions, with a compound of formula (III)

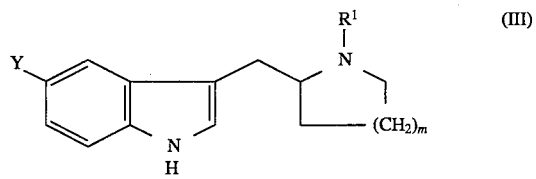

wherein $R^1$ and m are as defined for a compound of the formula (I) and Y is iodo or bromo and is preferably bromo, or is —$OSO_2CF_3$. Such a reaction should be carried out in the presence of a suitable catalyst such as a palladium or nickel catalyst. The type of catalyst used will vary with the character of M, the substrate and the structure of the compounds of formulae (II) and (III).

Suitable optionally substituted metal substituents for M above are described in Synthesis 1991, pages 413–432 (and the references described therein). Thus M can be, for example, any of the following:

(alkyl)$_3$Sn—, (alkyl)$_2$B—; (HO)$_2$B—; (alkoxy)$_2$B—, Li—; Cu—; chloroZn—; haloMg—; arylHg— or chloroHg—.

In a typical procedure a compound of the formula (II) wherein M is a trialkylstannane, e.g. tri-n-butylstannane, is reacted with a compound of the formula (III) in the presence of a suitable palladium catalyst, e.g. palladium (II) acetate, a suitable triarylphosphine, e.g. tri-o-tolylphosphine, a suitable base, e.g. triethylamine, and in a suitable solvent, e.g. acetonitrile. The reaction can be carried out at from room temperature to, and preferably at, the reflux temperature of the solvent and is preferably carried out under an inert atmosphere, e.g. under nitrogen or argon.

The intermediates of the formula (II) can be prepared by reacting a compound of the formula:

$$R—Y^1 \qquad (IV)$$

wherein R is as defined for a compound of the formula (I) and $Y^1$ is halo, preferably bromo or iodo, or is —$OSO_2CF_3$, as appropriate.

Compounds of formula (II) can be prepared by suitable metalation of a compound of formula (IV).

For a typical procedure (when M is a trialkylstannane) a compound of formula (IV) is reacted with a hexaalkyldistannane, e.g. hexa-n-butyldistannane, in the presence of a suitable palladium catalyst, e.g. palladium (II) acetate, a suitable base, e.g. triethylamine, a suitable triarylphosphine, e.g. tri-o-tolylphosphine, and in a suitable solvent, e.g. acetonitrile. The reaction is preferably carried out at an elevated temperature and under an inert atmosphere, e.g. at the reflux temperature of the solvent and under nitrogen.

The intermediates of the formula (IV) can be prepared by conventional methods.

The intermediates of the formula (III) can be prepared as shown in Scheme 1:

In a typical procedure a 5-haloindole of the formula (V) is converted to a magnesium derivative by reaction with a suitable Grignard reagent, e.g. ethylmagnesium bromide or methylmagnesium iodide, in a suitable solvent, e.g. diethyl ether or tetrahydrofuran, and this derivative is then reacted in situ with an acid chloride of the formula (VI) to provide a 3-acylindole of the formula (VII).

The acid chlorides of the formula (VI) can be prepared by conventional methods such as from the corresponding carboxylic acids, e.g. using oxalyl chloride and a trace of N,N-dimethylformamide in dichloromethane.

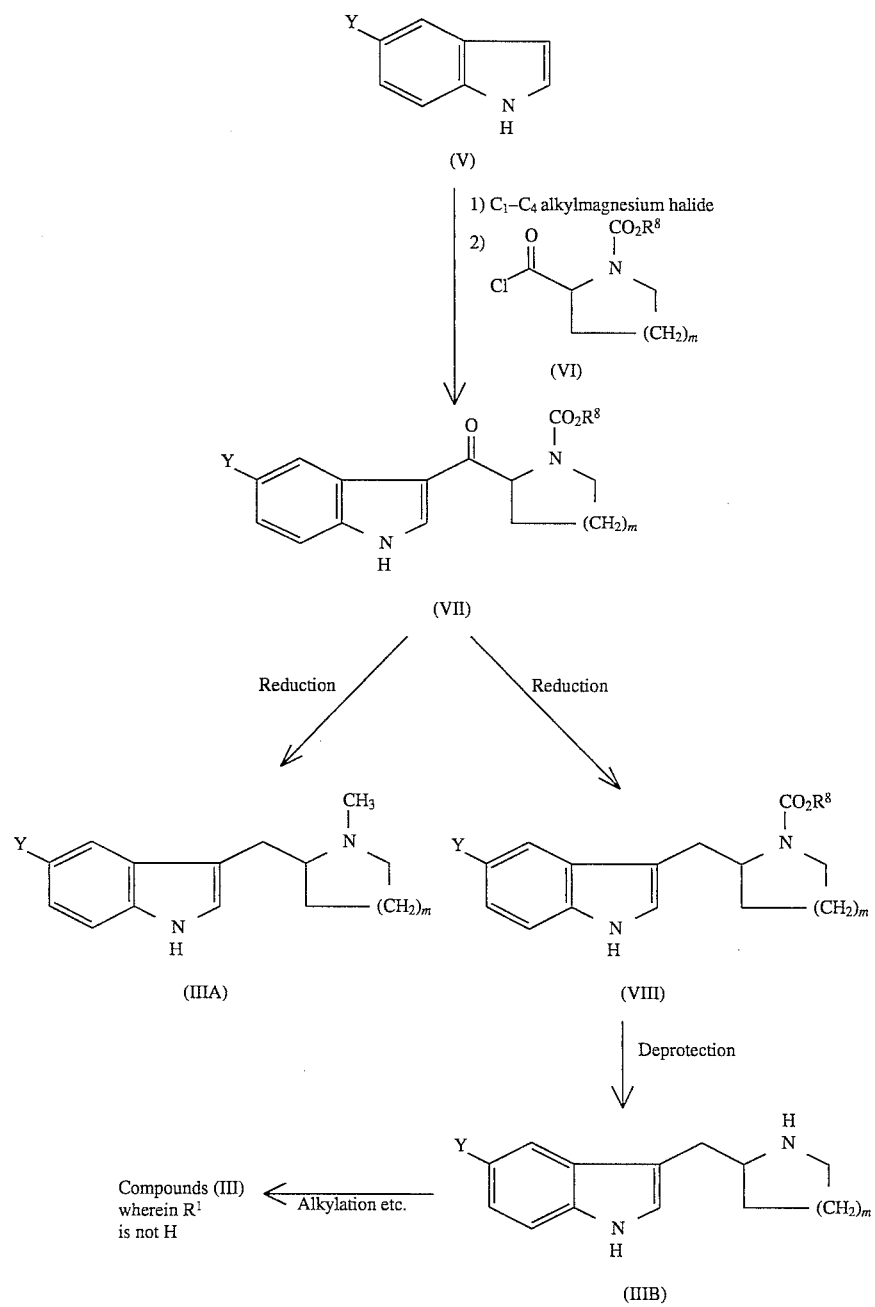

Scheme 1 wherein m and Y are as previously defined for a compound of the formula (III) and $R^8$ is benzyl or t-butyl.

A compound of the formula (III) wherein $R^1$ is methyl (i.e. a compound of the formula (IIIA)) can be prepared directly from a compound of the formula (VII) by reduction with a suitable reducing agent, e.g. lithium aluminium hydride, in a suitable solvent, e.g. tetrahydrofuran.

A compound of the formula (VII) can be reduced to a compound of the formula (VIII) with a suitable reducing agent, e.g. lithium borohydride, in a suitable solvent, e.g. tetrahydrofuran.

Deprotection of a compound of the formula (VIII) can be achieved using standard methodology, e.g. under acidic conditions when $R^8$ is t-butyl and by catalytic hydrogenation when $R^8$ is benzyl, to give a compound of the formula (IIIB).

Further useful non-hydrogenolytic N-deprotection procedures, when $R^8$ is benzyl, are either to employ hydrogen bromide in glacial acetic acid at about 0° C. or a Lewis acid-catalysed nucleophilic deprotection using, for example, boron trifluoride etherate and excess ethanethiol in a suitable solvent such as dichloromethane at about room temperature.

Further processes for the preparation of the compounds of formula (III) and the intermediates used to prepare them are as follows:

1. A compound of formula (III) may be obtained by selective N-alkylation of the saturated heterocyclic ring of a compound of formula (IIIB):

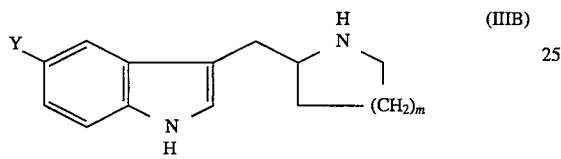

(IIIB)

wherein Y and m are as previously defined for formula (III), using one or more of the following methods.

(a) By reaction of a compound of formula (IIIB) with a compound of formula $R^1X$, wherein $R^1$ is as defined for formula (I), and X is a suitable leaving group, e.g. halo (preferably chloro, bromo or iodo), $C_1$–$C_4$ alkanesulphonyloxy, trifluoromethanesulphonyloxy or arylsulphonyloxy (preferably benzenesulphonyloxy or p-toluenesulphonyloxy), in the presence of an appropriate base, e.g. sodium or potassium carbonate or bicarbonate, or triethylamine, in a suitable solvent such as a $C_1$–$C_4$ alkanol, 1,2-dimethoxyethane, acetonitrile, dimethylformamide or N,N-dimethylacetamide, and optionally in the presence of sodium or potassium iodide. The reaction can be conducted at from about 0° C. to about 150° C., preferably at from about room temperature to about 100° C.

(b) By reductive alkylation of a compound of formula (IIIB) using the appropriate aldehyde-, ketone- or carboxylic acid containing $R^1$ precursor. In the case of an aldehyde or ketone precursor, the substrate (IIIB) and carbonyl reagent may be reacted together under conventional catalytic hydrogenation conditions or in the presence of sodium cyanoborohydride, in a suitable solvent such as methanol or ethanol, at about room temperature. Alternatively, the reductive alkylation may be achieved by a two-step procedure in which the intermediate enamine is formed initially under conventional conditions and subsequently reduced to the required amine, e.g. using sodium cyanoborohydride in tetrahydrofuran-methanol at about room temperature. In the case of a carboxylic acid precursor, the substrate (IIIB) and the said acid reagent may be reacted together in the presence of excess sodium borohydride in a suitable solvent; preferably the carboxylic acid itself is used as solvent whenever possible. Since this reductive alkylation proceeds via in situ formation of the corresponding sodium triacyloxyborohydride, obvious variations are to employ preformed intermediate when commercially available or to preform it in a separate in situ step using the stoichiometric amount of carboxylic acid in a suitable solvent. An example of the latter procedure involves the treatment of six equivalents of the carboxylic acid with two equivalents of sodium borohyride in dry tetrahydrofuran at about room temperature. When formation of the required sodium triacyloxyborohydride is complete, the reaction mixture is treated with a solution of one equivalent of the substrate (IIIB) in the same solvent and the subsequent reaction step is conducted at from about room temperature to about 70° C., preferably 50°–55° C.

(c) When $R^1$ is $C_2$–$C_4$ alkyl or $C_3$–$C_7$ cycloalkyl, each substituted at the 2-position with a hydroxy group, by reaction of a compound of formula (IIIB) with the appropriate epoxide-containing $R^1$ precursor, optionally in the presence of a tertiary amine base, e.g. triethylamine, and preferably in a suitable solvent such as $C_1$–$C_4$ alkanol. The reaction can be conducted at from about 0° C. to about 150° C., preferably at from about room temperature to about 60° C. When $R^1$ is 2-hydroxyethyl, an "ethylene oxide equivalent" is preferably employed. Thus a compound of formula (IIIB) may be reacted with ethylene carbonate in a suitable solvent such as dimethylformamide at about 120° C.

(d) When $R^1$ is $C_2$–$C_4$ alkyl substituted at the 2-position with an electron withdrawing group such as $R^5CO$, $R^6O_2C$, $R^3R^4NOC$, $R^3R^4NO_2S$, $R^5SO$, $R^5SO_2$ and certain aryl and heteroaryl systems (e.g. 2- or 4-pyridyl), by conjugate addition (Michael-type reaction) of a compound of formula (IIIB) to the corresponding α,β-unsaturated ketone-, ester-, amide-, sulphonamide-, sulphoxide-, sulphone-, arene- or heteroarene-containing $R^1$ precursor respectively, wherein $R^3$, $R^4$, $R^5$ and $R^6$ are as defined for formula (I), optionally in the presence of a tertiary amine base such as triethylamine. The reaction may optionally be conducted in a suitable solvent, e.g. N,N-dimethylacetamide, at from about 0° C. to about 100° C., preferably at about 100° C.

Certain compounds of formula (III) can be prepared from other compounds of formula (III) by, for example, the following conventional functional group transformations within the $R^1$ substituent:

(a) a compound of formula (I) wherein $R^1$ contains a $R^3R^4NOC$ substituent is obtainable from a corresponding ester of formula (I), i.e. wherein $R^1$ contains a $R^6O_2C$ substituent, by direct amination using an amine of formula $R^3R^4NH$. The reaction is preferably carried out using an excess of the amine in a suitable solvent such as a $C_1$–$C_4$ alkanol at an elevated temperature, e.g. the reflux temperature of the reaction medium. For low boiling amines, the reaction is preferably conducted in a sealed vessel. The same over-all transformation can be effected indirectly via the intermediacy of the corresponding carboxylic acid, i.e. a compound of formula (III) wherein $R^1$ contains a $HO_2C$ substituent. Depending on the nature of the ester, its deprotection may be achieved by acid or alkaline hydrolysis, protonolysis (e.g. when $R^6$ is t-butyl) or hydrogenolysis (e.g. when $R^6$ is benzyl). Conversion of the acid to the required amide may also be achieved by a variety of methods. For example, the acid may be activated by formation of the corresponding acyl halide, e.g. bromide or chloride, followed by reaction of the latter with an amine of formula $R^3R^4NH$ optionally in the presence of a reaction-inert base to act as acid scavenger. Alternatively, any of a host of standard amide bond-forming (peptide coupling) reagents may be used. For example, the acid may be activated using a carbodiimide such as 1-ethyl-3-dimethylamino-propylcarbodiimide, optionally in the presence of 1-hydroxybenzotriazole and a reaction-inert amine such as N-methylmorpholine, followed by in situ reaction of the activated acid with an amine of formula $R^3R^4NH$;

(b) a compound of formula (III) wherein $R^1$ contains a $R^5SO$, or $R^5SO_2$ substituent is obtainable from the corresponding sulphide of formula (I), i.e. wherein $R^1$ contains a $R^5S$ substituent, either by controlled oxidation using a stoichiometric amount of oxidising agent, or by using the required excess of oxidising agent, respectively. Suitable oxidising agents are, for example, a peracid such as meta-chloroperbenzoic acid, hydrogen peroxide or nitronium tetrafluoroborate.

2. A compound of formula (I) may be obtained by selective N-alkylation of the saturated heterocyclic ring of a compound of formula (IX):

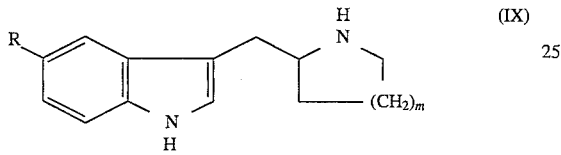

wherein R and m are as previously defined for formula (I), using one or more of the following methods.

(a) By reaction of a compound of formula (IX) with a compound of formula $R^1X$, wherein $R^1$ is as defined for formula (I), and X is a suitable leaving group, e.g. halo (preferably chloro, bromo or iodo), $C_1$–$C_4$ alkanesulphonyloxy, trifluoromethanesulphonyloxy or arylsulphonyloxy (preferably benzenesulphonyloxy or p-toluenesulphonyloxy), in the presence of an appropriate base, e.g. sodium or potassium carbonate or bicarbonate, or triethylamine, in a suitable solvent such as a $C_1$–$C_4$ alkanol, 1,2-dimethoxyethane, acetonitrile, dimethylformamide or N,N-dimethylacetamide, and optionally in the presence of sodium or potassium iodide. The reaction can be conducted at from about 0° C. to about 150° C., preferably at from about room temperature to about 100° C.

(b) By reductive alkylation of a compound of formula (IX) using the appropriate aldehyde-, ketone- or carboxylic acid-containing $R^1$ precursor. In the case of an aldehyde or ketone precursor, the substrate (IX) and carbonyl reagent may be reacted together under conventional catalytic hydrogenation conditions or in the presence of sodium cyanoborohydride, in a suitable solvent such as methanol or ethanol, at about room temperature. Alternatively, the reductive alkylation may be achieved by a two-step procedure in which the intermediate enamine is formed initially under conventional conditions and subsequently reduced to the required amine, e.g. using sodium cyanoborohydride in tetrahydrofuran-methanol at about room temperature. In the case of a carboxylic acid precursor, the substrate (IX) and the said acid reagent may be reacted together in the presence of excess sodium borohydride in a suitable solvent; preferably the carboxylic acid itself is used as solvent whenever possible. Since this reductive alkylation proceeds via in situ formation of the corresponding sodium triacyloxyborohydride, obvious variations are to employ preformed intermediate when commercially available or to preform it in a separate in situ step using the stoichiometric amount of carboxylic acid in a suitable solvent. An example of the latter procedure involves the treatment of six equivalents of the carboxylic acid with two equivalents of sodium borohyride in dry tetrahydrofuran at about room temperature. When formation of the required sodium triacyloxyborohydride is complete, the reaction mixture is treated with a solution of one equivalent of the substrate (IX) in the same solvent and the subsequent reaction step is conducted at from about room temperature to about 70° C., preferably 50°–55° C.

(c) When $R^1$ is $C_2$–$C_4$ alkyl or $C_3$–$C_7$ cycloalkyl, each substituted at the 2-position with a hydroxy group, by reaction of a compound of formula (IX) with the appropriate epoxide-containing $R^1$ precursor, optionally in the presence of a tertiary amine base, e.g. triethylamine, and preferably in a suitable solvent such as $C_1$–$C_4$ alkanol. The reaction can be conducted at from about 0° C. to about 150° C., preferably at from about room temperature to about 60° C. When $R^1$ is 2-hydroxyethyl, an "ethylene oxide equivalent" is preferably employed. Thus a compound of formula (IX) may be reacted with ethylene carbonate in a suitable solvent such as dimethylformamide at about 120° C.

(d) When $R^1$ is $C_2$–$C_4$ alkyl substituted at the 2-position with an electron withdrawing group such as $R^5CO$, $R^6O_2C$, $R^3R^4NOC$, $R^3R^4NO_2S$, $R^5SO$, $R^5SO_2$ and certain aryl and heteroaryl systems (e.g. 2- or 4-pyridyl), by conjugate addition (Michael-type reaction) of a compound of formula (IX) to the corresponding $\alpha,\beta$-unsaturated ketone-, ester-, amide-, sulphonamide-, sulphoxide-, sulphone-, arene- or heteroarene-containing $R^1$ precursor respectively, wherein $R^3$, $R^4$, $R^5$ and $R^6$ are as defined for formula (I), optionally in the presence of a tertiary amine base such as triethylamine. The reaction may optionally be conducted in a suitable solvent, e.g. N,N-dimethylacetamide, at from about 0° C. to about 100° C., preferably at about 100° C.

3. Certain compounds of formula (I) can be prepared from other compounds of formula (I) by, for example, the following conventional functional group transformations within the $R^1$ substituent:

(a) a compound of formula (I) wherein $R^1$ contains a $R^3R^4NOC$ substituent is obtainable from a corresponding ester of formula (I), i.e. wherein $R^1$ contains a $R^5O_2C$ substituent, by direct amination using an amine of formula $R^3R^4NH$. The reaction is preferably carried out using an excess of the amine in a suitable solvent such as a $C_1$–$C_4$ alkanol at an elevated temperature, e.g. the reflux temperature of the reaction medium. For low boiling amines, the reaction is preferably conducted in a sealed vessel. The same over-all transformation can be effected indirectly via the intermediacy of the corresponding carboxylic acid, i.e. a compound of formula (III) wherein $R^1$ contains a $HO_2C$ substituent. Depending on the nature of the ester, its deprotection may be achieved by acid or alkaline hydrolysis, protonolysis (e.g. when $R^5$ is t-butyl) or hydrogenolysis (e.g. when $R^5$ is benzyl). Conversion of the acid to the required amide may also be achieved by a variety of methods. For example, the acid may be activated by formation of the corresponding acyl halide, e.g. bromide or chloride, followed by reaction of the latter with an amine of formula $R^3R^4NH$ optionally in the presence of a reaction-inert base to act as acid scavenger. Alternatively, any of a host of standard amide bond-forming (peptide coupling) reagents may be used. For example, the acid may be activated using a carbodiimide such as 1-ethyl-3-dimethylaminopropylcarbodiimide, optionally in the presence of 1-hydroxybenzotriazole and a reaction-inert amine such as N-methylmorpholine, followed by in situ reaction of the activated acid with an amine of formula $R^3R^4NH$;

(b) a compound of formula (III) wherein $R^1$ contains a $R^5SO$, or $R^5SO_2$ substituent is obtainable from the corresponding sulphide of formula (I), i.e. wherein $R^1$ contains a $R^5S$ substituent, either by controlled oxidation using a stoichiometric amount of oxidising agent, or by using the required excess of oxidising agent, respectively. Suitable oxidising agents are, for example, a peracid such as metachloroperbenzoic acid, hydrogen peroxide or nitronium tetrafluoroborate.

Compounds of formula (IX) can be prepared by deprotection of a compound of formula (X):

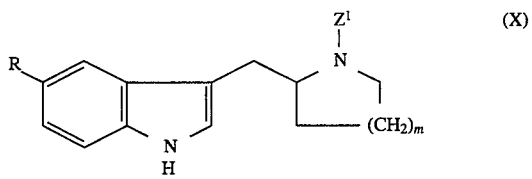
(X)

wherein R is as defined above for formula (I) and $Z^1$ is a protecting group such as —COOR$^8$ where $R^8$ is as defined for compound (VIII).

This can be achieved using standard methodology, e.g. under acidic conditions when $R^8$ is t-butyl and by catalytic hydrogenation when $R^8$ is benzyl, to give a compound of the formula (IX).

Further useful non-hydrogenolytic N-deprotection procedures, when $R^8$ is benzyl, are either to employ hydrogen bromide in glacial acetic acid at about 0° C. or a Lewis acid-catalysed nucleophilic deprotection using, for example, boron trifluoride etherate and excess ethanethiol in a suitable solvent such as dichloromethane at about room temperature.

Compounds of the formula (X) can be prepared by palladium-catalysed cross-coupling of a compound of the formula:

RM     (II)

wherein R is as defined above for a compound of formula (I) and M is an optionally substituted metal substituent suitable for cross-coupling reactions, with a compound of formula (VIII):

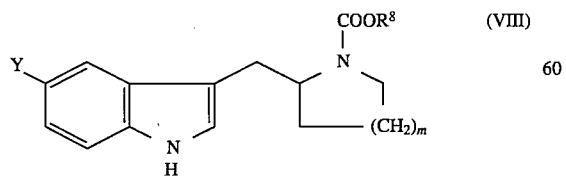
(VIII)

wherein $R^8$, Y and m are as defined above.

Such a reaction should be carried out in the presence of a suitable catalyst such as a palladium or nickel catalyst. The type of catalyst used will vary with the character of M, the substrate and the structure of the compounds of formulae (II) and (VIII).

Suitable optionally substituted metal substituents for M above are described in Synthesis 1991, pages 413–432 (and the references described therein). Thus M can be, for example, any of the following:

(alkyl)$_3$Sn—, (alkyl)$_2$B—; (HO)$_2$B—; (alkoy)$_2$B—, Li—; Cu—; chloroZn—; haloMg—; arylHg— or chloroHg—.

In a typical procedure a compound of the formula (II) wherein M is a trialkylstannane moiety, e.g. tri-n-butylstannane, is reacted with a compound of the formula (VIII) in the presence of a suitable palladium catalyst, e.g. palladium (II) acetate, a suitable triarylphosphine, e.g. tri-o-tolylphosphine, .a suitable base, e.g. triethylamine, and in a suitable solvent, e.g. acetonitrile. The reaction can be carried out at from room temperature to, and preferably at, the reflux temperature of the solvent and is preferably carried out under an inert atmosphere, e.g. under nitrogen or argon.

The intermediates of the formula (II) can be prepared as described previously.

4. Certain compounds of the formula (I) in which the substituent $R^2$ of the substituent group —X—$R^2$ on the phenyl or heterocyclic ring of R in formula (I) (and therefore forming part of R) is varied, can be prepared from other compounds of the formula (I) by functional group interconversion of the $R^2$ substituent as follows:

a) A compound of the formula (I) wherein $R^2$ is CONR$^3$R$^4$ can be prepared from a compound of the formula (I) wherein $R^2$ is CO$_2$R$^7$ by reaction with an amine of the formula:

HNR$^3$R$^4$.

The reaction is preferably carried out using an excess of the amine in a suitable solvent, e.g. a $C_1$–$C_4$ alkanol, and at an elevated temperature, e.g. at the reflux temperature of the solvent. For amines with a low boiling point the reaction is usually carried out in a sealed vessel.

b) A compound of the formula (I) wherein $R^2$ is CONR$^3$R$^4$ can also be prepared from a compound of the formula (I) wherein $R^2$ is CO$_2$R$^7$ by first hydrolysing the ester to the corresponding carboxylic acid using standard conditions, followed by either:

(i) condensation of the acid with an amine of the formula:

HNR$^3$R$^4$ under standard peptide coupling conditions, e.g. using dicyclohexylcarbodiimide or N,N'-carbonyldiimidazole; or (ii) conversion of the acid to a corresponding acyl halide, e.g. the chloride or bromide, followed by reaction with an amine of the formula:

HNR$^3$R$^4$, optionally in the presence of an additional base.

c) A compound of the formula (I) wherein $R^2$ is CONH$_2$ can be prepared from a compound of the formula (I) wherein $R^2$ is CN by a controlled hydrolysis, e.g. using concentrated sulphuric acid.

d) A compound of the formula (I) wherein $R^2$ is SO$_2$R$^7$ can be prepared from a compound of the formula (I) wherein $R^2$ is SOR$^7$ by oxidation with a suitable oxidising agent, e.g, metachloroperbenzoic acid or hydrogen peroxide.

e) A compound of the formula (I) wherein $R^2$ is NHCONR$^3$R$^4$ wherein $R^3$ and/or $R^4$ is $C_1$–$C_6$ alkyl or hydrogen can be prepared from a compound of the formula (I) wherein $R^2$ is NHCOR$^7$ by first hydrolysing the amide to the corresponding primary amine using standard conditions, followed by reaction of the amine with an isocyanate of the formula ($C_1$–$C_6$ alkyl)NCO.

f) A compound of the formula (I) wherein $R^2$ is NHSO$_2$R$^7$ can be prepared from a compound of the formula (I) wherein $R^2$ is NHCOR$^7$ by first generating the corresponding primary amine as in method 5(e) above, followed by reaction thereof with the appropriate alkanesulphonyl halide (preferably the chloride) or alkanesulphonic anhydride, optionally in the presence of an additional base.

g) A compound of the formula (I) wherein $R^2$ is COR$^7$ can be prepared from a compound of the formula (I) wherein $R^2$ is CN by first reacting with a Grignard reagent of the formula:

($C_1$–$C_6$ alkyl)MgY$^3$ wherein $y^3$ is chloro, bromo or iodo, followed by hydrolysis of the imine intermediate obtained.

h) A compound of formula (I) wherein $R^2$ is OH can be prepared from a compound of formula (I) wherein $R^2$ is COR$^7$ or wherein $R^2$ is $C_2R^7$ by treatment with a suitable reducing agent e.g. lithium aluminium hydride or by treatment with a suitable metaloalkane reagent, e.g, a Grignard reagent of the formula ($C_1$–$C_4$ alkyl)MgY$^3$ wherein $y^3$ is chloro, bromo or iodo.

5. Compounds of formula (I) can be prepared by suitable indole N-deprotection of a compound of formula:

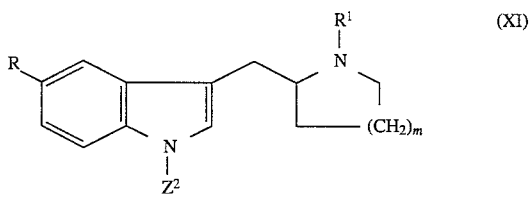
(XI)

wherein R, $R^1$ and m are as defined for a compound of the formula (I) but $R^1$ is not hydrogen, or $R^1$ is a protecting group $Z^1$ wherein $Z^1$ is —COOR$^8$ wherein $R^8$ is as defined for formula (VIII) and $Z^2$ is a suitable indole N-protecting group such as: an alkoxycarbonyl group e.g. t-butyloxycarbonyl or a trialkylsilyl group e.g. triisopropylsilyl, e.g. t-butyldimethylsilyl. Suitable indole N-deprotection of a compound of formula (XI) can be achieved using standard methodology; for example, when $Z^2$ is t-butyloxycarbonyl, by protonolysis using trifluoroacetic acid or hydrogen chloride or, when $Z^2$ is trialkylsilyl, by protonolysis using hydrogen chloride or by treatment with an appropriate fluoride source such as tetra-n-butylammonium fluoride.

Compounds of formula (XI) can be prepared by suitably catalysed cross coupling of a compound of formula:

R—X (XII)

wherein R is as defined for a compound of the formula (I) and X is halo or trifluoromethanesulphonyl, with a compound of the formula:

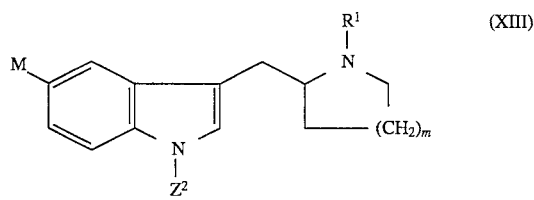
(XIII)

wherein $R^1$ and m are as defined for a compound of the formula (XI), $Z^2$ is as defined above for formula (XI) and M is as defined in formula (II), e.g. a trialkylstannane such as tri-n-butylstannane; e.g. a dialkylborane such as diethylborane; lithium; halomagnesium; chlorozinc; copper; aryl or chloromercury; dihydroxyborane; dialkoxyborane. Such reactions should be carried out in the presence of a suitable palladium or nickel catalyst. The type of catalyst will vary with the character of M, the substrate and the structure of the compounds of formula (XIII) and (XII).

In a typical procedure a compound of formula (XIII) where M is tri-n-butylstannane, is reacted with a compound of formula (XII) in the presence of a suitable palladium catalyst, e.g. tetrakistriphenylphosphinepalladium (O), in a suitable solvent, e.g. toluene. The reaction can be carried out at from room temperature to, and preferably at, the reflux temperature of the solvent and is preferably carried out under an inert atmosphere, e.g. under nitrogen or argon.

Compounds of formula (XIII) can be prepared by suitable metalation of a compound of formula:

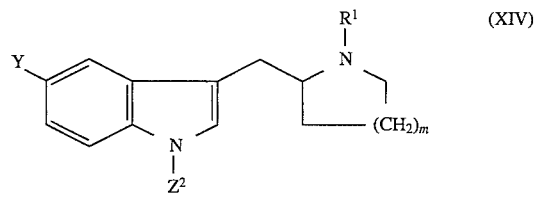
(XIV)

wherein $R^1$, $Z^2$ and m are as defined above for a compound of formula (XIII) and Y is halo, preferably bromo, or —OSO$_2$CF$_3$.

In a typical procedure for the preparation of a compound of the formula (XIV) wherein M is a trialkylstannane, e.g. tri-n-butylstannane, a compound of the formula (XIV) is reacted with n-butyllithium (solution in hexanes) in a suitable solvent, e.g. tetrahydrofuran and the resultant solution is treated with the corresponding trialkylstannylhalide, e.g. tri-n-butylstannylchloride, or the corresponding hexaalkyldistannane e.g. hexa-n-butyldistannane.

In an alternative typical procedure for the preparation of a compound of formula (XIII) wherein M is trialkylstannane, e.g. tri-n-butylstannane a compound of the formula (XIV) is reacted with a hexaalkyldistannane e.g. hexa-n-butyldistannane, in the presence of a suitable catalyst, e.g. palladium (II) acetate, a suitable base, e.g. triethylamine, a suitable triarylphosphine, e.g. tri-o-tolylphosphine, and in a suitable solvent, e.g. acetonitrile.

The reaction is preferably carried out at an elevated temperature and under an inert atmosphere, e.g. at the reflux temperature of the solvent and under nitrogen.

A compound of formula (XIV) may be obtained from a compound of formula (III) using standard methodology; for example, when $Z^2$ is trialkylsilyl (e.g. triisopropylsilyl or t-butyldimethylsilyl), by treating a compound of formula (III) with a suitable base, such as potassium hydride, in a suitable solvent, such as tetrahydrofuran and then reacting the resultant anion with a suitable silylating agent, such as the corresponding trialkylsilyl trifluoromethanesulphonate or the corresponding trialkylsilyl chloride; for example, when $Z^2$ is alkoxycarbonyl, e.g. t-butyloxycarbonyl, by treating with a suitable alkoxycarbonylating agent e.g. di-t-butyldicarbonate in a suitable solvent e.g. acetonitrile and, where appropriate, in the presence of a suitable catalyst e.g. 4-dimethylaminopyridine.

All of the above reactions are conventional and appropriate reagents and reaction conditions for their performance and procedures for isolating the desired products will be well known to those skilled in the art, in accordance with literature precedents and by reference to the Examples and Preparations hereto.

A pharmaceutically acceptable acid addition salt is readily prepared by mixing together solutions containing the free base and the desired acid. The salt generally precipitates from solution and is collected by filtration, or is recovered by evaporation of the solvent.

The compounds of the formula (I) and their salts are selective agonists at the "5-HT$_1$-like" subtype of 5-hydroxytryptamine receptor and are therefore useful in the curative or prophylactic treatment of migraine and associated conditions such as cluster headache, chronic paroxysmal hemicrania and headache associated with vascular disorders. Certain compounds of the formula (I) are also agonists at central 5-HT$_1$ receptors and are therefore useful for the treatment of depression, anxiety, eating disorders, obesity and drug abuse.

The in vitro evaluation of the "5-HT$_1$-like" receptor agonist activity of the compounds of the formula (I) is carried out by testing the extent to which they mimic sumatriptan in contracting the dog isolated saphenous vein strip (P. P. A. Humphrey et al., *Br. J. Pharmacol.*, 94, 1123 (1988)). This effect can be blocked by methiothepin, a known 5-HT antagonist, Sumatriptan is known to be useful in the treatment of migraine and produces a selective increase in carotid vascular resistance in the anaesthetized dog and a consequent decrease in carotid arterial blood flow. It has been suggested (W. Feniuk et al., *Br. J. Pharmacol.*, 96, 83 (1989)) that this is the basis of its efficacy.

In therapy, the compounds of the formula (I) and their salts can be administered alone, but will generally be administered in admixture with a pharmaceutical carrier selected with regard to the intended route of administration and standard pharmaceutical practice. For example, they cain be administered orally in the form of tablets containing such excipients as starch or lactose, or in capsules or ovules either alone or in admixture with excipients, or in the form of elixirs, solutions or suspensions containing flavouring or colouring agents.

They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For buccal or sublingual administration the compounds of the formula (I) may be administered in the form of tablets or lozenges which can be formulated in a conventional manner.

For oral, parenteral, buccal and sublingual administration to patients the daily dosage level of the compounds of the formula (I) and their salts will be from 0.01 to 20 mg/kg (in single or divided doses). Thus tablets or capsules of the compounds will contain from 5 mg to 0.5 g of active compound for administration singly or two or more at a time, as appropriate. The physician in any event will determine the actual dosage which will be most suitable for an individual patient and it will vary with the, age, weight and response of the particular patient. The above dosages are exemplary of the average case; there can, of course, be individual instances where higher or lower dosage ranges are merited, and such are within the scope of this invention.

Alternatively, the compounds of formula (I) can be administered in the form of a suppository or pessary, or they may be applied topically in the form of a lotion, solution, cream, ointment or dusting powder. For example, they can be incorporated into a cream consisting of an aqueous emulsion or polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) can also be administered intranasally or by inhalation and are conveniently delivered in the form of a solution or suspension from a pump spray container that is squeezed or pumped by the patient or as an aerosol spray presentation from a pressurized container or a nebulizer with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the formula (I) and a suitable powder base such as lactose or starch.

Aerosol formulations are preferably arranged so that each metered dose or "puff" of aerosol contains 20 µg to 1000 µg of a compound of the formula (I) for delivery to the patient. The overall daily dose with an aerosol will be within the range 100 µg to 10 mg which may be administered in a single dose or, more usually, in divided doses throughout the day.

Thus the invention further provides:

a) A pharmaceutical composition comprising a compound of the formula (I), or a pharmaceutically acceptable salt thereof, together with a pharmaceutically acceptable diluent or carrier;

b) A compound of the formula (I), or a pharmaceutically acceptable salt or composition thereof, for use as a medicament;

c) The use of a compound of the formula (I), or of a pharmaceutically acceptable salt or composition thereof, for the manufacture of a medicament for the curative or prophylatic treatment of migraine or an associated condition such as cluster headache, chronic paroxysmal hemicrania or headache associated with vascular disorders, or for the treatment of depression, anxiety, an eating disorder, obesity or drug abuse;

d) A method of treating a human being to cure or prevent migraine or an associated condition such as cluster headache, chronic paroxysmal hemicrania or headache associated with vascular disorders, or depression, anxiety, an eating disorder, obesity or drug abuse, which comprises treating said human being with an effective amount of a compound of the formula (I) or with a pharmaceutically acceptable salt or composition thereof;

e) The use of a compound of the formula (I), or of a pharmaceutically acceptable salt or composition thereof, for the manufacture of a medicament for the curative or prophylactic treatment of a medical condition for which a selective agonist of 5-HT$_1$-like receptors is indicated; and f) A method of treating a human being to cure or prevent a medical condition for which a selective agonist of 5-HT$_1$-like receptors is indicated which comprises treating said human being with an effective amount of a compound of the formula (I) or with a pharmaceutically acceptable salt or composition thereof;

The following Examples illustrate the preparation of the compounds of the formula (I) and wherein:

Examples 1 to 34, 47, 48 and 50 to 55 illustrate the cross-coupling process used to make the compounds of the present invention.

Examples 35 to 39 illustrate the preparation of N-pyrrolidines by the removal of a protecting group e.g. a benzyloxycarbonyl group from the N-atom of the pyrrolidine ring.

Examples 40 to 46 illustrate the alkylation of N-pyrrolidines e.g. those prepared in Examples 35, 38 and 39.

Examples 49, 63 and 66 illustrate the reduction of 5-substituted indole derivatives of the invention using lithium aluminium hydride.

Examples 56 and 57 illustrate the use of boron compounds (boranes) as coupling agents in place of the tin compounds (stannanes) of the, preceding Examples.

Examples 58 and 59 illustrate the preparation of 5-substituted indoles of the invention by the removal of a protecting group (e.g. t-butoxycarbonyl) from the N-atom of the indole ring.

Examples 60 and 61 illustrate the process of Examples 1 to 34 to produce indole derivatives of the invention with a cyclopropylmethyl group on the N-atom of the pyrrolidine ring.

Examples 62, 64 and 65 illustrate the preparation of 5-substituted indole derivatives of the invention involving the removal from the N-atom of the indole ring of a silyl protecting group.

EXAMPLE 1

This Example illustrates the preparation of:

3-(1-Methylpyrrolidin-2(R)-ylmethyl)-5-(4-methylsulphonylphenyl)-1H-indole

A mixture of 4-methylsulphonylphenyltri-n-butylstannane (see Preparation 15) (680 mg, 1.53 mmol) tri-o-tolyphosphine (120 mg, 0,394 mmol), palladium (II) acetate (15 mg, 0.067 mmol), triethylamine (0.40 ml, 2.87 mmol) and 5-bromo-3-(1-methylpyrrolidin-2(R)-ylmethyl)-1H-indole (400 mg, 1.36 mmol) (see Preparation 36) in anhydrous acetonitrile (5 ml) was heated under reflux, under nitrogen, for 18 hours. The reaction mixture was then evaporated under reduced pressure and dichloromethane (25 ml) was added. The resultant solution was washed with aqueous sodium carbonate, dried (Na$_2$SO$_4$) and evaporated. The residue was purified by column chromatography on silica gel, eluting with ethyl acetate/diethylamine (98:2) to afford, after combination and evaporation of the appropriate fractions, the title compound as a white foam, (189 mg). Found: C,68.17; H,6.81; N,7.53; C$_{21}$H$_{24}$N$_2$O$_2$S.$\frac{1}{20}$ CH$_2$Cl$_2$ requires: C,67.83; H,6.51; N,7.52%.

$[\alpha]_D^{25}$+63° (c=0.1 in methanol)

$^1$H-NMR (CDCl$_3$): δ=1.50–1.70(m,2H), 1.70–1.90(m, 2H), 2.15–2.30(m,1H), 2.40–2.57(m,1H), 2.50(s,3H), 2.60–2.77 (m,1H), 3.10–3.30(m,2H), 3.12(s,3H), 5.35(s, $\frac{1}{10}$H), 7.10(s,1H), 7.45–7.50(m,2H), 7.82(d,2H), 7.85(s, 1H), 8.00(d,2H), 8.22,(s,1H) ppm.

EXAMPLES 2 TO 34

The compounds of the following tabulated Examples were prepared by similar methods to that of Example 1 using the appropriate phenyltri-n-butylstannane derivatives (see Preparations 2 to 12, 1, 13, 14 and 16 to 34) and 5-bromo-3-(1-methylpyrrolidin-2(R)-ylmethyl)-1H-indole as the starting materials.

The compounds have the general formula:

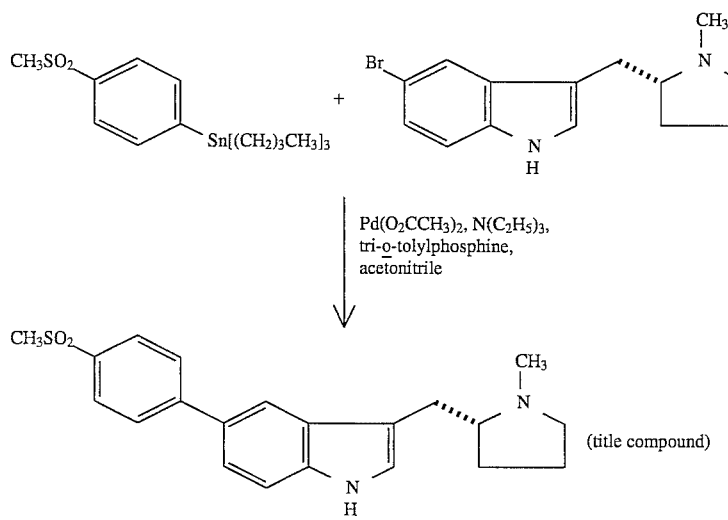

| Ex No | R | Analysis (%) | $^1$H—NMR (in CDCl$_3$ unless otherwise stated) | $[\alpha]_D^{25}$ (c = 0.1 in methanol) |
|---|---|---|---|---|
| 2 | SO$_2$NH$_2$ — phenyl (para) | — | (D$_6$—DMSO/CDCl$_3$): δ=1.10–1.55 (m, 4H), 1.90–2.00 (m, 1H), 2.10–2.25 (m, 1H), 2.17(s, 3H), 2.25–2.40 (m, 1H), 2.60–3.00 (m, integral obscured by solvent), 6.78(s, 1H), 7.05 (d, 1H), 7.13 (d, 1H), 7.43 (d, 2H), 7.45 (s, 1H), 7.65 (d, 2H), 9.98(s, 1H) ppm. | — |
| 3 | SO$_2$NH$_2$ — phenyl (meta) | — | (D$_6$—DMSO/CDCl$_3$): δ=1.25–1.65 (m, 4H), 1.90–2.10 (m, 1H), 2.15–2.50 (m, integral obscured by solvent), 2.25(s, 3H), 2.78–3.00 (m, 2H), 6.45 (s, 1H), 6.85 (s, 1H), 7.12–7.33 (m, integral obscured by solvent), 7.55(s, 1H, 7.57 (d, 1H), 7.87 (s, 1H), 9.83(s, 1H) ppm. | — |
| 4 | SO$_2$NHCH$_3$ — phenyl (para) | Found: C, 64.34; H, 6.45; N, 10.33; C$_{21}$H$_{25}$N$_3$O$_2$S .3/20CH$_2$Cl$_2$ required: C, 64.11; H, 6.44; N, 10.60. | δ=1.50–1.70 (m, 2H), 1.70–1.90 (m, 2H), 2.15–2.30 (m, 1H), 2.40–2.55 (m, 1H), 2.48(s, 3H), 2.55–2.70 (m, 4H), 3.10–3.30 (m, 2H) 4.40 (s, 1H), 7.10 (s, 1H), 7.38–7.50 (m, 2H), 7.79 (d, 2H), 7.80 (s, 1H), 7.90 (d, 2H), 8.15 (s, 1H) ppm. | +53° |

-continued

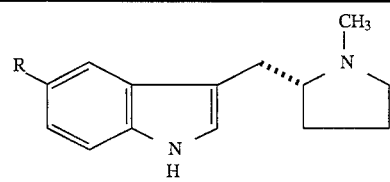

| Ex No | R | Analysis (%) | $^1$H-NMR (in CDCl$_3$ unless otherwise stated) | $[\alpha]_D^{25}$ (c = 0.1 in methanol) |
|---|---|---|---|---|
| 5 | SO$_2$NHCH$_3$ (3-substituted phenyl) | Found: C, 62.70; H, 6.49; N, 10.42; C$_{21}$H$_{25}$N$_3$O$_2$S .1/4CH$_2$Cl$_2$ requires: C, 63.00; H, 6.35; N, 10.38. | δ=1.50–1.95 (m, 4H), 2.15–2.30 (m, 1H), 2.40–2.60 (m, 1H), 2.47(s, 3H), 2.50 (s, 3H), 2.60–2.80 (m, 1H), 3.10–3.30 (m, 2H), 4.47 (s, 1H), 5.31 (s, 1/2H), 7.10 (s, 1H), 7.38–7.50 (m, 2H), 7.58 (dd, 1H), 7.75–7.92 (m, 3H), 8.15 (s, 1H), 8.17 (s, 1H) ppm. | +48° |
| 6 | SO$_2$N(CH$_3$)$_2$ (4-substituted phenyl) | Found: C, 62.04; H, 6.74; N, 9.57; C$_{22}$H$_{27}$N$_3$O$_2$S .2/5CH$_2$Cl$_2$ requires; C, 62.35; H, 6.49; N, 9.74. | δ=1.50–1.70 (m, 2H), 1.70–1.90 (m, 2H), 2.15–2.30(m, 1H), 2.40–2.60(m, 1H), 2.48(s, 3H), 2.60–2.80 (m, 1H), 2.77(s, 6H), 3.10–3.30 (m, 2H), 5.30 (s, 4/5H), 7.10 (s, 1H), 7.44–7.52 (m, 2H), 7.75–7.90 (m, 5H), 8.20(s, 1H) ppm. | +64° |
| 7 | SO$_2$N(CH$_3$)$_2$ (3-substituted phenyl) | Found: C, 65.63; H, 6.88; N, 10.18; C$_{22}$H$_{27}$N$_3$O$_2$S.1/15 CH$_2$Cl$_2$ requires: C, 65.69; H, 6.77; N, 10.40. | δ=1.55–1.75 (m, 2H), 1.75–1.95(m, 2H), 2.20–2.35 (m, 1H), 2.40–2.85(m, 2H), 2.50(s, 3H), 2.77(s, 6H), 3.13–3.30(m, 2H), 7.12(s, 1H), 7.40–7.50 (m, 2H), 7.60(dd, 1H), 7.70(d, 1H), 7.79(s, 1H), 7.88(d, 1H), 8.05 (s, 1H), 8.20(s, 1H) ppm. | +54° |
| 8 | CONH$_2$ (4-substituted phenyl) | — | δ=1.55–1.75 (m, 2H), 1.75–1.90 (m, 2H), 2.18–2.30 (m, 1H), 2.40–2.60 (m, 1H), 2.51(s, 3H), 2.60–2.75 (m, 1H), 3.10–3.30 (m, 2H), 6.13 (s, 1H), 6.37(s, 1H), 7.07(s, 1H), 7.18–7.25 (m, 2H), 7.72 (d, 2H), 7.82(s, 1H), 7.90(d, 2H), 8.75(s, 1H) ppm. | +179° |

-continued

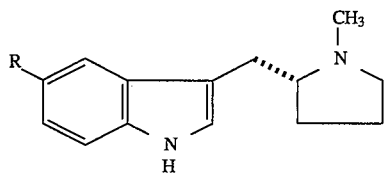

| Ex No | R | Analysis (%) | $^1$H—NMR (in CDCl$_3$ unless otherwise stated) | $[\alpha]_D^{25}$ (c = 0.1 in methanol) |
|---|---|---|---|---|
| 9 | CONH$_2$ (3-substituted phenyl) | — | δ=1.55–1.75 (m, 2H), 1.75–2.00 (m, 2H), 2.20–2.35 (m, 1H), 2.45–2.60 (m, 1H), 2.50(s, 3H), 2.65–2.78 (m, 1H), 3.10–3.35 (m, 2H), 5.85 (s, 1H), 6.28(s, 1H), 7.10(s, 1H), 7.45–7.55 (m, 2H), 7.58 (dd, 1H), 7.78 (d, 1H), 7.85(d, 1H), 7.90(s, 1H), 8.15 (s, 1H), 8.35(s, 1H) ppm. | +36° |
| 10 | CONHCH$_3$ (4-substituted phenyl) | Found: C, 73.12; H, 7.33; N, 11.27; C$_{22}$H$_{26}$N$_3$O.3/4H$_2$O requires: C, 73.20; H, 7.40; N, 11.64. | δ=1.25(s, 11/2H), 1.50–1.70(m, 2H), 1.70–1.92(m, 2H), 2.15–2.30(m, 1H), 2.38–2.60(m, 1H), 2.50(s, 3H), 2.60–2.75 (m, 1H), 2.95–3.15 (m, 5H), 6.25(s, 1H), 7.10(s, 1H), 7.35–7.50 (m, 2H), 7.70 (d, 2H), 7.80(s, 1H), 7.82(d, 2H), 8.30 (s, 1H) ppm. | +74° |
| 11 | CONHCH$_3$ (3-substituted phenyl) | Found: C, 73.98; H, 7.43; N, 11.72; C$_{22}$H$_{25}$N$_3$O.1/2H$_2$O requires: C, 74.13; H, 7.35; N, 11.79. | (D$_6$—DMSO): δ=1.38–1.78(m, 4H), 1.95–2.15(m, 1H), 2.20–2.40(m, 1H), 2.35 (s, 3H), 2.40–2.60 (m, 1H), 2.70–3.12 (m, 5H), 7.18(s, 1H), 7.30–7.45 (m, 2H), 7.58(dd, 1H), 7.70 (d, 1H), 7.75–7.88 (m, 2H), 8.10(s, 1H), 8.52(s, 1H) ppm. | +87° |
| 12 | CON(CH$_3$)$_2$ (4-substituted phenyl) | Found: C, 73.45; H, 7.44; N, 11.30; C$_{23}$H$_{27}$N$_3$O.3/4H$_2$O requires: C, 73.67; H, 7.66; N, 11.21. | δ=1.50–1.70 (m, 2H), 1.70–1.92 (m, 31/2H), 2.15–2.30 (m, 1H), 2.40–2.55 (m, 1H), 2.48(s, 3H), 2.58–2.70 (m, 1H), 2.95–3.30 (m, 8H), 7.07 (s, 1H), 7.38–7.14 (m, 2H), 7.50(d, 2H), 7.68(d, 2H), 7.80 (s, 1H), 8.26(s, 1H) ppm. | +60° |

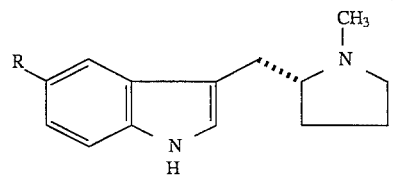

| Ex No | R | Analysis (%) | $^1$H—NMR (in CDCl$_3$ unless otherwise stated) | $[\alpha]_D^{25}$ (c = 0.1 in methanol) |
|---|---|---|---|---|
| 13 | CON(CH$_3$)$_2$ (phenyl) | Found: C, 72.92; H, 7.45; N, 10.80; C$_{23}$H$_{27}$N$_3$O.1/4CH$_2$Cl$_2$ requires: C, 72.97; H, 7.24; N, 10.98. | δ=1.50–1.70 (m, 2H), 1.70–1.90 (m, 2H), 2.15–2.30 (m, 1H), 2.35–2.57(m, 1H), 2.45(s, 3H), 2.57–2.70 (m, 1H), 2.90–3.30 (m, 2H), 3.05 (s, 3H), 3.18( s,3H), 5.30(s, 1/2H), 7.07 (s, 1H), 7.35(d, 1H), 7.38–7.42(m, 2H), 7.45(dd, 1H), 7.65–7.75 (m, 2H), 7.80 (s, 1H), 8.28(s, 1H) ppm. | +38° |
| 14 | CON(morpholino) (phenyl) | Found: C, 71.70; H, 7.20; N, 9.99; C$_{25}$H$_{29}$N$_3$O$_2$.1/5CH$_2$Cl$_2$ requires: C, 71.41; H, 6.95; N, 9.99. | δ=1.50–1.70 (m, 2H), 1.70–1.90 (m, 2H), 2.15–2.28 (m, 1H), 2.30–2.55 (m, 1H), 2.45(s, 3H), 2.60–2.70 (m, 1H), 3.08–3.30 (m, 2H), 3.40–3.95(m, 8H), 5.30 (s, 2/5H), 7.05 (s, 1H), 7.36(d, 1H), 7.38–7.42(m, 2H), 7.48(dd, 1H), 7.70 (s, 1H), 7.72(d, 1H), 7.78(s, 1H), 8.28 (s, 1H) ppm. | −84° |
| 15 | SO$_2$CH$_3$ (phenyl) | — | δ=1.50–1.88 (m, 4H), 2.17–2.30 (m, 1H), 2.40–2.55 (m, 1H), 2.47(s, 3H), 2.62–2.72 (m, 1H), 3.05–3.30 (m, 2H), 3.12 (s, 3H), 7.10(s, 1H), 7.40–7.50(m, 2H), 7.63(dd, 1H), 7.80 (s, 1H), 7.90(d, 1H), 7.92(d, 1H), 8.18 (s, 1H), 8.21(s, 1H) ppm. | +102° |
| 16 | SO$_2$CH$_2$CH$_3$ (phenyl) | Found: C, 68.89; H, 7.09; N, 7.62; C$_{22}$H$_{26}$N$_2$O$_2$S requires: C, 69.08; H, 6.85; N, 7.32. | δ=1.32(t, 3H), 1.48–1.90(m, 4H), 2.18–2.30(m, 1H), 2.38–2.58(m, 1H), 2.46(s, 3H), 2.60–2.72 (m, 1H), 3.05–3.30 (m, 4H), 7.10(s, 1H), 7.38–7.50 (m, 2H), 7.62 (dd, 1H), 7.80 (s, 1H), 7.82(d, 1H), 7.92(d, 1H), 8.12 (s, 1H), 8.16(s, 1H) ppm. | +79° |

-continued

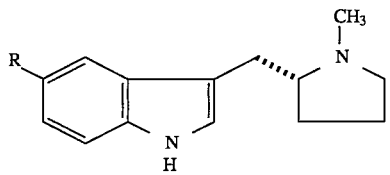

| Ex No | R | Analysis (%) | $^1$H—NMR (in CDCl$_3$ unless otherwise stated) | $[\alpha]_D^{25}$ (c = 0.1 in methanol) |
|---|---|---|---|---|
| 17 | SO$_2$CH$_2$CH$_2$CH$_3$ (3-phenyl) | Found: C, 69.27; H, 7.29; N, 7.29; C$_{23}$H$_{28}$N$_2$O$_2$S requires: C, 69.66; H, 7.12; N, 7.06. | δ=1.02(t, 3H), 1.50–2.00(m, 6H), 2.20–2.37(m, 1H), 2.40–2.65(m, 1H), 2.47(s, 3H), 2.65–2.80 (m, 1H), 3.05–3.17 (m, 4H), 7.15(s, 1H), 7.40–7.50 (m, 2H), 7.60(dd, 1H), 7.80 (s, 1H), 7.85(d, 1H), 7.95(d, 1H), 8.18 (s, 1H), 8.25(s, 1H) ppm. | +88° |
| 18 | CH$_2$SO$_2$CH$_3$ (3-phenyl) | — | δ=1.45–1.90 (m, 4H); 2.15–2.30 (m, 1H), 2.37–2.57 (m, 1H), 2.43(s, 3H), 2.60–2.72 (m, 1H), 2.80 (s, 3H), 3.10–3.30 (m, 2H), 4.35(s, 2H), 7.07(s, 1H), 7.38 (d, 1H), 7.39–7.42 (m, 2H), 7.45 (dd, 1H), 7.67 (s, 1H), 7.70(d, 1H), 7.75(s, 1H), 8.12 (s, 1H) ppm. | +81° |
| 19 | CH$_2$SO$_2$CH$_2$CH$_3$ (3-phenyl) | Found: C, 67.72; H, 7.16; N, 7.11; C$_{23}$H$_{28}$N$_2$O$_2$S .3/5H$_2$O requires: C, 67.82; H, 7.22; N, 6.88. | δ=1.42(t, 3H), 1.55–1.95(m, 5.2H), 2.15–2.42(m, 1H), 2.45–2.60(m, 1H), 2.50(s, 3H), 2.62–2.78 (m, 1H), 2.95 (q, 2H), 3.12–3.32 (m, 2H), 4.35(s, 2H), 7.10(s, 1H), 7.40 (d, 1H), 7.45–7.52 (m, 2H), 7.55 (dd, 1H), 7.65–7.75 (m, 2H), 7.80(s, 1H), 8.10(s, 1H) ppm. | +45° |
| 20 | SOCH$_3$ (3-phenyl) | Found: C, 68.66; H, 7.06; N, 7.52; C$_{21}$H$_{24}$N$_2$OS.4/5H$_2$O requires: C,68.74; H, 7.03; N, 7.63. | δ=1.40–1.90 (m, 5.6H), 2.17–2.30 (m, 1H), 2.40–2.55 (m, 1H), 2.45 (s, 3H), 2.65–2.75 (m, 1H), 2.79(s, 3H), 3.05–3.30(m, 2H), 7.07(s, 1H), 7.45–7.50 (m, 2H), 7.55–7.65 (m, 2H), 7.75–7.80 (m, 1H), 7.80 (s, 1H), 7.92(s, 1H), 8.20(s, 1H) ppm. | — |

-continued

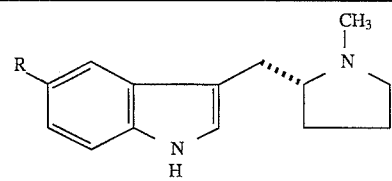

| Ex No | R | Analysis (%) | ¹H—NMR (in CDCl₃ unless otherwise stated) | $[\alpha]_D^{25}$ (c = 0.1 in methanol) |
|---|---|---|---|---|
| 21 | SOCH₂CH₃ (3-substituted phenyl) | Found: C, 69.04; H, 7.37; N, 7.27; C₂₂H₂₆N₂OS.9/10H₂O requires: C, 69.04; H, 7.32; N, 7.31. | δ=1.25(t, 3H), 1.50–1.95(m, 5.8H), 2.16–2.30(m, 1H), 2.38–2.58(m, 1H), 2.48(s, 3H), 2.60–2.72 (m, 1H), 2.78–3.05 (m, 2H), 3.08–3.30 (m, 2H), 7.10 (s, 1H), 7.38–7.50 (m, 2H), 7.50–8.05 (m, 2H), 7.78(d, 1H), 7.80(s, 1H), 7.88 (s, 1H), 8.25 (s, 1H) ppm. | — |
| 22 | COCH₃ (4-substituted phenyl) | Found: C, 72.41; H, 7.20; N, 8.01; C₂₂H₂₄N₂O.9/20CH₂Cl₂ requires: C, 72.75; H, 7.55; N, 7.56. | δ=1.65–1.80, (m, 2H), 1.80–2.06 (m, 2H), 2.35–2.60 (m, 1H), 2.52(s, 3H), 2.65 (s, 3H), 2.70–2.95 (m, 2H), 3.15–3.47 (m, 2H), 5.30(s, 9/10H), 7.20 (s, 1H), 7.40–7.52 (m, 2H), 7.72(d, 2H), 7.80(s, 1H), 8.05 (d, 2H), 8.37(s, 1H) ppm. | +53° |
| 23 | COCH₃ (3-substituted phenyl) | Found: C, 76.35; H, 7.03; N, 8.25; C₂₂H₂₄N₂O.1/5CH₂Cl₂ requires: C, 76.31; H, 7.04; N, 8.02. | δ=1.50–1.91 (m, 4H), 2.15–2.28 (m, 1H), 2.38–2.75 (m, 2H), 2.48(s, 3H), 2.68 (s, 3H), 3.10–3.30 (m, 2H), 7.10(s, 1H), 7.40–7.50(m, 2H), 7.55(dd, 1H), 7.80 (s, 1H), 7.87(d, 1H), 7.92(d, 1H), 8.15 (s, 1H), 8.25(s, 1H) ppm. | +58° |
| 24 | CH₂OH (4-substituted phenyl) | Found: C, 75.38; H, 7.55; N, 8.44; C₂₁H₂₄N₂O.3/4H₂O requires: C, 75.53; H, 7.70; N, 8.39. | δ=1.55–2.05 (m, 6 1/2H), 2.15–2.30 (m, 1H), 2.40–2.55 (m, 1H), 2.45(s, 3H), 2.60–2.75 (m, 1H), 3.10–3.35 (m, 2H), 4.77 (s, 2H), 7.05(s, 1H), 7.40–7.45(m, 2H), 7.45(d, 2H), 7.67 (d, 2H), 7.80(s, 1H), 8.15(s, 1H) ppm. | +59° |

-continued

[Structure: 5-R-substituted indole with 3-position bearing a CH2 group connected to (S)-2-pyrrolidinyl with N-CH3]

| Ex No | R | Analysis (%) | ¹H—NMR (in CDCl₃ unless otherwise stated) | $[\alpha]_D^{25}$ (c = 0.1 in methanol) |
|---|---|---|---|---|
| 25 | 3-(CH₂OH)-C₆H₄– | Found: C, 74.35; H, 7.86; N, 8.51; C₂₁H₂₄N₂O.H₂O requires: C, 74.52; H, 7.74; N, 8.28. | δ=1.50–1.72 (m, 2H), 1.73–1.90 (m, 2H), 2.00–2.15 (m, 3H), 2.17–2.30 (m, 1H), 2.40–2.60 (m, 1H), 2.45(s, 3H), 3.10–3.40 (m, 2H), 4.79 (s, 2H), 7.05(s, 1H), 7.35(d, 1H), 7.40–7.50 (m, 3H), 7.61 (d, 1H), 7.70(s, 1H), 7.82(s, 1H), 8.20 (s, 1H) ppm. | +71° |
| 26 | 3-(CO₂CH₃)-C₆H₄– | — | (CDCl₃/D₆—DMSO): δ=1.30–1.48 (m, 2H), 1.48–1.70 (m, 2H), 1.94–2.10 (m, 1H), 2.15–2.35 (m, integral obscured by solvent), 2.25(s, 3H), 2.38–2.50 (m, 1H), 2.82–3.05 (m, 2H), 3.70 (s, 3H), 6.85(s, 1H), 7.10–7.32(m, integral obscured by solvent), 7.54 (s, 1H), 7.60(d, 1H), 7.70(d, 1H), 8.05 (s, 1H), 9.80(s, 1H) ppm. | +74° |
| 27 | 4-(CH₂NHSO₂CH₂CH₃)-C₆H₄– | Found: C, 66.09; H, 7.35; N, 9.54; C₂₃H₂₉N₃O₂S.1/2H₂O requires: C, 65.69; H, 7.19; N, 9.51. | δ=1.37(t, 3H), 1.45–1.90(m, 5H), 2.18–2.30(m, 1H), 2.37–2.57(m, 1H), 2.47(s, 3H), 2.60–2.72 (m, 1H), 3.00(q, 2H), 3.08–3.30 (m, 2H), 4.35(s, 2H), 4.60 (s, 1H), 7.07 (s, 1H), 7.35–7.50(m, 4H), 7.67(d, 2H), 7.78 (s, 1H), 8.17(s, 1H) ppm. | +70° |
| 28 | 4-(NC)-C₆H₄– | Found: C, 78.81; H, 6.52; N, 13.16; C₂₁H₂₁N₃.1/4H₂O requires C, 78.84; H, 6.77; N, 13.13. | δ=1.50–1.95 (m, 4H), 2.00–2.30 (m, 1.5H), 2.40–2.60 (m, 1H), 1.50 (s, 1H), 2.60–2.75 (m, 1H), 3.10–3.25 (m, 2H), 7.10(s, 1H), 7.25(s, 1H), 7.40–7.50 (m, 2H), 7.65–7.85 (m, 4H), 7.80 (s, 1H), 8.30(s, 1H). | +90° |

-continued

| Ex No | R | Analysis (%) | ¹H—NMR (in CDCl₃ unless otherwise stated) | $[\alpha]_D^{25}$ (c = 0.1 in methanol) |
|---|---|---|---|---|
| 29 | (4-methylphenyl)CH₂C(=O)NH₂ | — | δ=1.50–1.90 (m, 4H), 2.15–2.30 (m, 1H), 2.45(s, 3H), 2.55–2.70(m, 1H), 3.10–3.40(2H), 3.65(s, 2H), 5.45 (s, 2H), 7.05(s, 1H), 7.25(d, 2H), 7.35–7.45 (m, 2H), 7.65 (d, 2H), 8.80(s, 1H), 8.10(s, 1H). | +62° |
| 30 | (4-methylphenyl)C(CH₃)₂OH | Found: C, 76.29; H, 8.05; N, 8.12; C₂₃H₂₈N₂O.7/10 H₂O requires C, 76.05; H, 8.21; N, 7.76. | δ=1.50–1.90 (m, 5.4H), 1.60 (s, 6H), 2.15–2.30 (m, 1H), 2.40–2.55 (m, 1H), 2.50(s, 3H), 2.55–2.70(m, 2H), 3.10–3.30(m, 2H), 7.05(s, 1H), 7.30–7.50 (m, 2H), 7.55 (d, 2H), 7.65(d, 2H), 7.80(s, 1H), 8.10 (s, 1H). | +72° |
| 31 | 3-cyanophenyl | Found: C, 73.06; H, 6.52; N, 12.24; C₂₁H₂₁N₃.5/12CH₂Cl₂ requires C, 73.33; H, 6.27; N, 11.98. | δ=1.65–2.00 (m, 4H), 2.40–2.65 (m, 2H), 2.60(s, 3H), 2.75–2.95(m, 2H), 3.25–3.55(m, 2H), 5.35(s, 5/6H), 7.25 (s, 1H), 7.35–7.65 (m, 4H), 7.80(s, 1H), 7.95(d, 1H), 8.00 (s, 1H), 8.55(s, 1H). | +55° |
| 32 | (3-methylphenyl)CH₂C(=O)N(CH₃)₂ | Found: C, 76.54; H, 7.82; N, 10.78; C₂₄H₂₉N₃O requires C, 76.77; H, 7.78; N, 11.18. | δ=1.50–1.90 (m, 4H), 2.15–2.30 (m, 1H), 2.40–2.55 (m, 1H), 2.50(s, 3H), 2.55–2.90(m, 1H), 3.00(s, 3H), 3.05 (s, 3H), 3.05–3.30 (m, 2H), 3.80(s, 2H), 7.05(s, 1H), 7.20 (d, 1H), 7.35–7.45 (m, 3H), 7.50–7.55 (m, 2H), 7.80(s, 1H), 8.15(s, 1H). | +65° |
| 33 | C₂H₅NH—C(=O)—(3-substituted phenyl) | Found: C, 75.44; H, 7.58; N, 11.22; C₂₃H₂₇N₃O.1/3H₂O requires C, 75.17; H, 7.59; N, 11.43. | δ=1.25(t, 3H), 1.45–1.90(m, 4 2/3H), 2.15–2.30 (m, 1H), 2.40–2.55 (m, 1H), 2.50(s, 3H), 2.55–2.70 (m, 1H), 3.10–3.30 (m, 2H), 3.55 (q, 2H), 6.20(s, 1H), 7.05(s, 1H), 7.35–7.55 (m, 3H), 7.70(d, 1H), 7.75(d, 1H), 7.80(s, 1H), 8.00 (s, 1H), 8.15(s, 1H). | +74° |

-continued

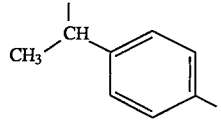

| Ex No | R | Analysis (%) | ¹H—NMR (in CDCl₃ unless otherwise stated) | $[\alpha]_D^{25}$ (c = 0.1 in methanol) |
|---|---|---|---|---|
| 34 | OH–CH(CH₃)–C₆H₄– | Found: C, 77.02; H, 8.12; N, 8.17; C₂₂H₂₆N₂O.1/2H₂O requires C, 76.93; H, 7.92; N, 8.17. | δ=1.45–2.00 (m, 4H), 1.60(d, 3H), 2.15–2.30(m, 1H), 2.35–2.55(m, 1H), 2.50(s, 3H), 2.55–2.70 (m, 1H), 3.10–3.30 (m, 2H), 4.90–5.00 (q, 1H), 7.05 (s, 1H), 7.35–7.50 (m, 4H), 7.65(d, 2H), 7.80(s, 1H), 8.10 (s, 1H). | — |

EXAMPLE 35

This Example illustrates the preparation of:

5-(3-N,N-Dimethylcarbamoylphenyl)-3-(pyrrolidin-2(R)-ylmethyl)-1H-indole

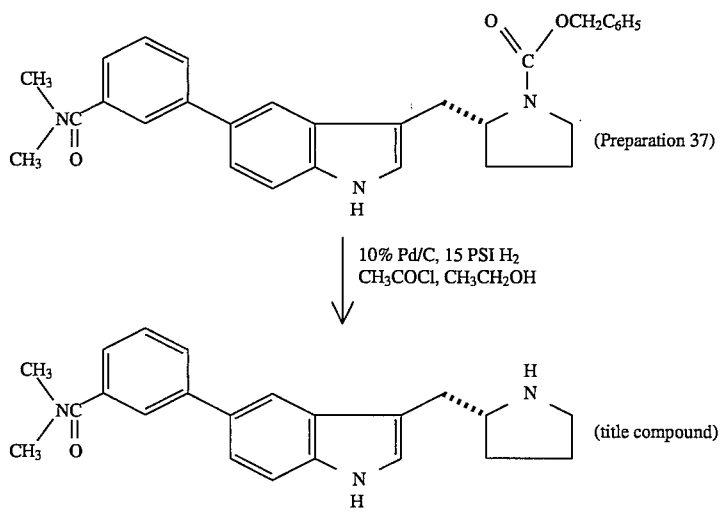

3-(1-Benzyloxycarbonylpyrrolidin-2(R)-ylmethyl)-5-(3-N,N-dimethylcarbamoylphenyl)-1H-indole (904 mg, 1.80mmol) (see Preparation 37) was dissolved in ethanol (100 ml) and acetyl chloride (130 μL, 1.83 mmol) was added dropwise to the resultant solution. 10% Palladium on carbon (300 mg) was then added and the reaction stirred for 18 hours at room temperature under a pressure of 1 bar of hydrogen. The reaction was then halted and the catalyst removed by filtration through arbacel. Solvent removal under reduced pressure gave a white foam which was taken up in dichloromethane (250 ml); washed with aqueous sodium carbonate and dried (Na₂SO₄). Solvent evaporation gave the crude product which was purified by column chromatography on silica gel, eluting with dichloromethane/methanol/ammonium hydroxide (90:10:1) to afford, after combination and evaporation of the appropriate fractions, the title compound as a white foam, (583 mg). Found: C,71.77; H,7.21; N,10.89; C₂₂H₂₅N₃O.3/10 CH₂Cl₂ requires: C,71.82; H,6.92; N,11.27%.

$[\alpha]_D^{25}$ –17° (c=0.1 in methanol).

¹H-N.M.R. (CDCl₃): δ=1.40–1.55(m,1H), 1.65–2.00(m, 3H), 2.70–3.30(m,10H), 3.35–3.50(m,1H), 5.30(s,⅗H), 7.05(s,1H), 7.30(d,1H), 7.30–7.50(m,3H), 7.60–7.75(m, 2H), 7.80(s,1H), 8.60(s,1H).

EXAMPLE 36

This Example illustrates the preparation of:

5-(3-Hydroxymethylphenyl)-3-(pyrrolidin-2(R)-ylmethyl)-1H-indole

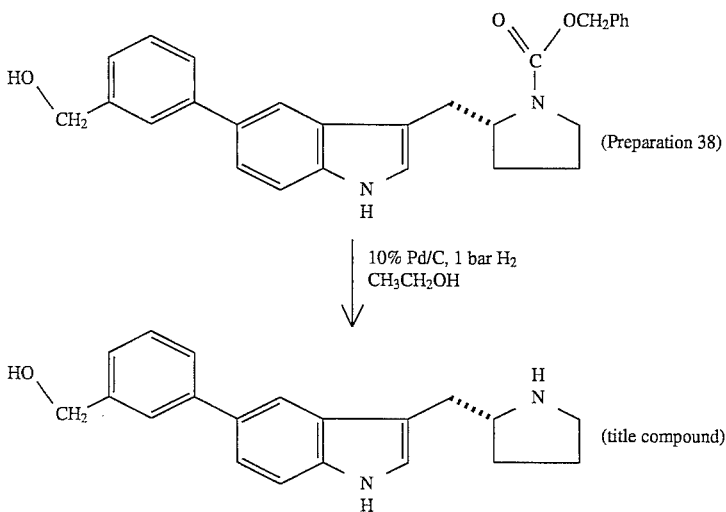

(Preparation 38)

10% Pd/C, 1 bar H₂
CH₃CH₂OH (title compound)

3-(1-Benzyloxycarbonylpyrrolidin-2(R)-ylmethyl)-5-(3-hydroxymethylphenyl)-1H-indole (1.030 g, 2.316 mmol) (see Preparation 38) in ethanol was reduced using catalytic hydrogenation as described in Example 35 except that no acetyl chloride was used in the reaction. This gave the title compound as an off-white foam (453 mg). Found: C,72.36; H,6.76; N,8.20; $C_{20}H_{22}N_2O \cdot \%CH_2Cl_2$ requires: C,72.35; H,6.78; N,8.28%.

$[\alpha]_D^{25}$ –21° (c=0.1 in methanol).

¹H-N.M.R. (CDCl₃/D₆-DMSO): δ=1.40–1.55(m,1H), 1.70–2.00(m,3H), 2.80–2.90(m,1H), 2.90–3.10(m,3H), 3.40–3.50(m,1H), 4.72(s,2H), 5.25(s,¾H), 7.15(s,1H), 7.35(d,1H), 7.35–7.45(m,2H), 7.55(d,1H), 7.70(s,1H), 7.80(s,1H), 8.70(s,1H).

EXAMPLE 37

This Example illustrates the preparation of:

5-(4-Hydroxymethylphenyl)-3-(pyrrolidin-2(R)-ylmethyl)-1H-indole

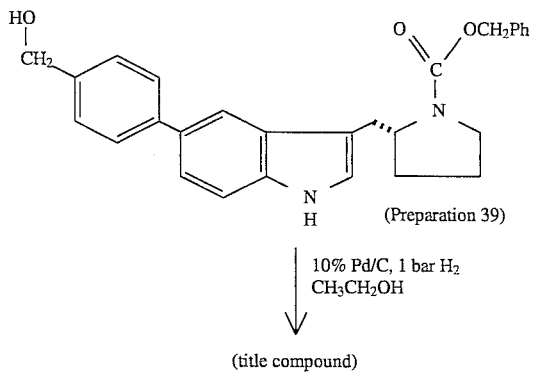

(Preparation 39)

10% Pd/C, 1 bar H₂
CH₃CH₂OH (title compound)

3-(1-Benzyloxycarbonylpyrrolidin-2(R)-ylmethyl)-5-(4-hydroxymethylphenyl)-1H-indole (450 mg, 0.973 mmol) (see Preparation 39) in ethanol was reduced using catalytic hydrogenation as described in Example 35 except that no acetyl chloride was used in the reaction. This gave the title compound as an off-white powder, m.pt. 65°–69° C. (210 mg). Found: C,76.15; H,7.43; N,8.66; $C_{20}H_{22}N_2O \cdot \tfrac{1}{2}H_2O$ requires: C,76.16; H,7.35; N,8.88%.

$[\alpha]_D^{25}$ –11° (c=0.1 in methanol).

¹H-N.M.R. (CD₃OD): δ=1.40–1.60(m,1H), 1.60–2.00(m,3H), 2.70–3.05(m,3H), 3.25–3.50(m,2H), 4.60(s,2H), 7.10(s,1H), 7.30–7.45(m,6H), 7.60(d,2H), 7.80(s,1H).

EXAMPLE 38

This Example illustrates the preparation of:

5-(3-Carbamoylphenyl)-3-(pyrrolidin-2(R)-ylmethyl)-1H-indole

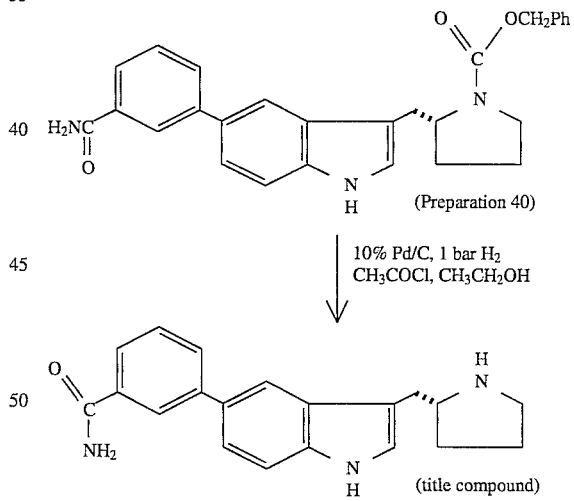

(Preparation 40)

10% Pd/C, 1 bar H₂
CH₃COCl, CH₃CH₂OH (title compound)

3-(1-Benzyloxycarbonylpyrrolidin-2(R)-ylmethyl)-5-(3-carbamoylphenyl)-1H-indole (700 mg, 1.391 mmol) (see Preparation 40) in ethanol was reduced using catalytic hydrogenation, as described in Example 35. This gave the title compound as a white foam (345 mg). Found: C,71.16; H,6.98; N,12.34; $C_{20}H_{21}N_3O \cdot H_2O$ requires: C,71.19; H,6.87; N, 12.45.

$[\alpha]_D^{25}$ –16° (c=0.1 in methanol).

¹H-N.M.R. (CDCl₃/CD₃OD): δ=1.50–1.60(m,1H), 1.70–2.00(m,3H), 2.75–2.90(m,1H), 3.00–3.15(m,3H), 3.40–3.50(m,1H), 7.10(s,1H), 7.40(s,1H), 7.50(dd,1H), 7.75–7.85(m,2H), 7.90(s,1H), 8.15(s,1H).

EXAMPLE 39

This Example illustrates the preparation of:

5-(4-Carbamoylphenyl)-3-(pyrrolidin-2(R)-ylmethyl)-1H-indole

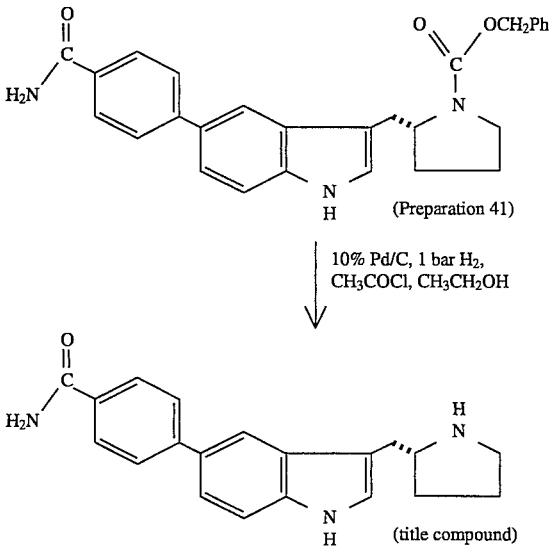

3-(1-Benzyloxycarbonylpyrrolidin-2(R)-ylmethyl)-5-(4-carbamoylphenyl)-1H-indole (355 mg, 0.784 mmol) (see Preparation 41) in ethanol was reduced using catalytic hydrogenation, as described in Example 35. This gave the title compound as a white foam (210 mg). Found: C,72.33; H,6.80; N,12.35; $C_{20}H_{21}N_3O \cdot \sqrt[3]{4}H_2O$ requires: C,72.16; H,6.81; N,12.62%.

$[\alpha]_D^{25}$ –18° (c=0.1 in methanol).

$^1$H-N.M.R. (CDCl$_3$/CD$_3$OD): δ=1.40–1.60(m,1H), 1.70–2.00(m,3H), 2.70–2.85(m,1H), 2.95–3.10(m,3H), 3.35–3.50(m,1H), 7.10(s,1H), 7.40–7.50(m,2H), 7.75(d, 2H)m, 7.85(s,1H), 7.95(d,1H).

EXAMPLE 40

This Example illustrates the preparation of:

5-(3-N,N-Dimethylcarbamoylphenyl)-3-[1-(2-methoxyethyl)pyrrolidin-2(R)-ylmethyl]-1H-indole

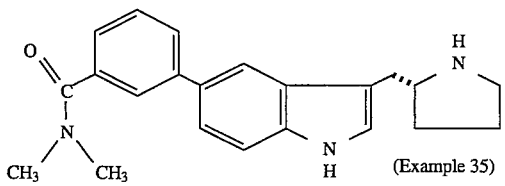

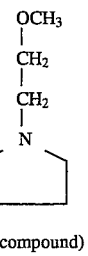

To a stirred solution of 5-(3-N,N-Dimethylcarbamoylphenyl)-3-(pyrrolidin-2(R)-ylmethyl)-1H-indole (100 mg, 0.2565 mmol) (see Example 35) in 1,2-dimethoxyethane (2.0 ml) was added sequentially sodium carbonate (27 mg, 0.25 mmol), sodium iodide (43 mg, 0.29 mmol) and finally 2-bromomethoxyethane (24 µL, 36 mg, 0.259 mmol). The mixture was stirred at reflux under nitrogen, for 14 hours. The reaction was then cooled to room temperature and partitioned between ethyl acetate (200 ml) and aqueous sodium carbonate (200 ml). The organic layer was dried (sodium sulphate) and the solvent removed under reduced pressure to give the crude product. Purification by column chromatography on silica gel, eluting with dichloromethane/methanol/ammonium hydroxide (90:10:0.1) afforded, after combination and evaporation of the appropriate fractions, the title compound as a white foam (63 mg). Found: C,66.46; H,7.28; N,9.30; $C_{25}H_{31}N_3O_2 \cdot \tfrac{2}{3}CH_2Cl_2$ requires: C,66.70; H,7.05; N,9.09%.

$[\alpha]_D^{25}$ +16° (c=0.1 in methanol).

$^1$H-N.M.R. (CDCl$_3$): δ=1.65–2.05(m,4H), 2.60–2.80(m, 2H), 2.85–3.45(m,4H), 2.90(s,3H), 3.10(s,3H), 3.30(s,3H), 3.40–3.70(m,3H), 5.25(s,1⅓H), 7.25(s,1H), 7.20–7.40(m, 4H), 7.60(d,1H), 7.65(s,1H), 7.20(s,1H), 8.70(s,1H).

EXAMPLE 41

This Example illustrates the preparation of:

5-(3-Carbamoylphenyl)-3-[1-(2-methoxyethyl)pyrrolidin-2(R)-ylmethyl]-1H-indole 5-(3-Carbamoylphenyl)-3-(pyrrolidin-2(R)-ylmethyl)-1H-indole (60 mg, 0.1881 mmol) (see Example 38) and 2-bromomethoxyethane were reacted together in 1,2-dimethoxyethane, in the presence of sodium carbonate and sodium iodide using a procedure similar to that described in Example 40. This yielded the title compound as a white foam (48 mg). Found: C,69.82; H,7.33; N,10.23; $C_{23}H_{27}N_3O_2 \cdot \tfrac{1}{8}CH_2Cl_2 \cdot \tfrac{1}{2} H_2O$ requires: C,69.94; H,7.17; N,10.58%.

$[\alpha]_D^{25}$ +38° (c=0.1 in methanol).

$^1$H-N.M.R. (CDCl$_3$): δ=1.25(s,1H), 1.55–1.95(m,4H), 2.15–2.35(m,1H), 2.40–2.55(m,1H), 2.65–2.90(m,2H), 3.15–3.35(m,3H), 3.35(s,3H), 3.50–3.65(m,2H), 5.25(s, ¼H), 5.65(bs,1H), 6.30(bs,1H), 7.05(s,1H), 7.35–7.55(m, 3H), 7.70(d,1H), 7.80(d,1H), 7.85(s,1H), 8.10(bs,2H).

EXAMPLE 42

This Example illustrates the preparation of:

5-(4-Carbamoylphenyl)-3-[1-(2-methoxyethyl)pyrrolidin-2(R)-ylmethyl]-1H-indole 5-(4-Carbamoylphenyl)-3-(pyrrolidin-2(R)-ylmethyl)-1H-indole (60 mg, 0.1881 mmol) (see Example 39) and 2-bromomethoxyethane were reacted together in 1,2- dimethoxyethane, in the presence of sodium carbonate and sodium iodide using a procedure similar to that described in Example 40. This yielded the title compound as a white foam (38 mg). Found: C,65.45; H,7.21; N,9.58; $C_{23}H_{27}N_3O_2 \cdot \frac{1}{2} CH_2Cl_2 \cdot \frac{5}{8}H_2O$ requires: C,65.46; H,6.84; N,9.74%.

$[\alpha]_D^{25}$ +54° (c=0.1 in methanol).

$^1$H-N.M.R. (CDCl$_3$/CD$_3$OD): δ=1.45–1.85(m,4H), 2.20–2.35(m,1H), 2.40–2.55(m,1H), 2.55–2.70(m,1H), 2.70–2.90(m,1H), 3.10–3.30(m,3H) 3.25(s,3H), 3.50(t,2H), 5.25(s,1H), 7.00(s,1H), 7.30–7.35(m,2H), 7.60(d,2H), 7.70(s,1H), 7.80(d,2H).

EXAMPLE 43

This Example illustrates the preparation of:

3-[1-(2-Carbamoylethyl)pyrrolidin-2(R)-ylmethyl]
5-(3-N,N-Dimethylcarbamoylphenyl)-1H-indole

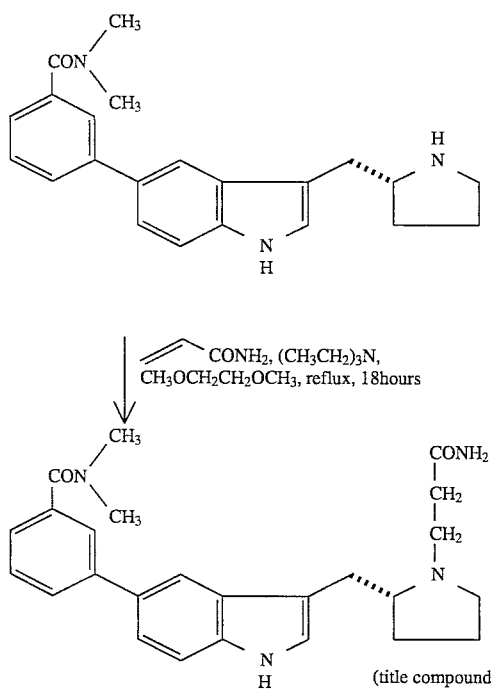

To a stirred solution of 5-(3-N,N-dimethycarbamoylphenyl)-3-(pyrrolidin-2(R)-ylmethyl)-1H-indole (131 mg, 0.336 mmol) (see Example 35) in 1,2-dimethoxyethane (2.6 ml) was added triethylamine (0.13 ml, mmol) and acrylamide (26 mg, 0.369 mmol). The mixture was stirred at reflux, under nitrogen, for 18 hours. The reaction was then cooled to room temperature and partitioned between ethyl acetate (100 ml) and water (100 ml). The organic phase was separated, washed with water (100 ml) and dried (sodium sulphate). Solvent removal under reduced pressure gave the crude product. Purification by column chromatography on silica gel, eluting with dichloromethane/methanol/ammonium hydroxide (90:10:0.5) afforded, after combination and evaporation of the appropriate fractions, the title compound as a white foam (80 mg). Found: C,63.85; H,6.78; N,11.84; $C_{25}H_{30}N_4O_2 \cdot \frac{3}{4}CH_2Cl_2$ requires: C,64.14; H,6.58; N,11.62%.

$[\alpha]_D^{25}$ +54° (c=0.1 in methanol).

$^1$H-N.M.R. (CDCl$_3$): δ=1.50–1.95(m,4H), 2.15–2.60(m, 5H), 2.65–2.80(m,1H), 2.80–2.95(m,1H), 3.00(s,3H), 3.15(s,3H), 3.15–3.35(m,2H), 5.30(s,1½H), 5.50(bs,1H), 7.00(s,1H), 7.25–7.50(m,4H), 7.65(d,1H), 7.70(s,1H), 7.75(s,1H), 8.10(bs,1H), 8.50(s,1H).

EXAMPLE 44

This Example illustrates the preparation of:

3-[1-(2-Carbamoylethyl)pyrrolidin-2(R)-ylmethyl]5-(3-carbamoylphenyl)-1H-indole 5-(3-carbamoyl)-3-(pyrrolidin-2(R)-ylmethyl)-1H-indole (52 mg, 0.155 mmol) (see Example 38) and acrylamide were reacted together in 1,2-dimethoxyethane, in the presence of triethylamine, using a procedure similar to that described in Example 43. This yielded the title compound as a white solid (38 mg). Found: C,66.01; H,6.77; N,12.91; $C_{23}H_{26}N_4O_2 \cdot \frac{1}{3}CH_2Cl_2 \cdot \frac{1}{3}H_2O$ requires: C,65.97; H,6.49; N, 13.19%.

$[\alpha]_D^{25}$ +45° (c=0.1 in methanol).

$^1$H-N.M.R. (CDCl$_3$/CD$_3$OD): δ=1.60–1.95(4H), 2.25–3.00(m,6H), 3.15–3.40(m, integral obscured by solvent), 5.30(s,⅔H), 7.05(s,1H), 7.35–7.45(m,2H), 7.50(dd, 1H), 7.75–7.90(m,2H), 7.90(s,1H), 8.15(s,1H).

EXAMPLE 45

This Example illustrates the preparation of:

3-[1-(2-Carbamoylethyl)pyrrolidin-2(R)-ylmethyl]5-(4-carbamoylphenyl)-1H-indole 5-(4-carbamoylphenyl)-3-(pyrrolidin-2(R)-ylmethyl)-1H-indole (60 mg, 0.180 mmol) (see Example 39) and acrylamide were reacted together in 1,2-dimethoxyethane, in the presence of triethylamine, using a procedure similar to that described in Example 43. This yielded the title compound as a white solid (42 mg). Found: C,64.48; H,6.98; N,12.47; $C_{23}H_{26}N_4O_2 \cdot 2H_2O \cdot \frac{1}{3}CH_3OH$ requires: C,64.10; H,7.22; N,12.82%.

$^1$H-N.M.R. (CDCl$_3$/CD$_3$OD): δ=1.50–1.90(m,4H), 2.15–2.55(m,4H), 2.57–2.70(m,1H), 2.70–2.85(m,1H), 3.10–3.30(m,3H), 3.30(s,1H), 7.00(s,1H), 7.30–7.40(m,2H), 7.65(d,2H), 7.70(s,1H), 7.80(d,2H).

EXAMPLE 46

This Example illustrates the preparation of:

3-[1-(2-N,N-dimethylcarbamoylethyl)pyrrolidin-2(R)-ylmethyl]5-(3-N,N-dimethylcarbamoylphenyl)-1H-indole 5-(3-N,N-dimethylcarbamoylphenyl)-3-(pyrrolidin-2(R)-ylmethyl)-1H-indole (100 mg, 0.256 mmol) (see Example 35) and N,N-dimethylacrylamide were reacted together in 1,2-dimethoxyethane, in the presence of triethylamine, using a procedure similar to that described in Example 43. This yielded the title compound as a white foam (78 mg). Found: C,66.19; H,7.31; N,11.23; $C_{27}H_{34}N_4O_2 \cdot \frac{2}{3}CH_2Cl_2$ requires: C,66.04; H,7.14; N,11.13%.

$[\alpha]_D^{25}$ +5° (c=0.1 in methanol).

$^1$H-N.M.R. (CDCl$_3$): δ=1.50–1.90(m,4H), 2.30–2.50(m, 1H), 2.55–3.10(m,18H), 3.15–3.40(m,2H), 5.25(s,1⅓H), 7.05(s,1H), 7.25(d,1H), 7.30–7.45(m,3H), 7.60–7.65(m, 2H), 7.70(s,1H), 8.50(s,1H).

EXAMPLE 47

This Example illustrates the preparation of:

3-(1-methylpyrrolidin-2(R)-ylmethyl)-5-(2-pyridyl)-1H-indole

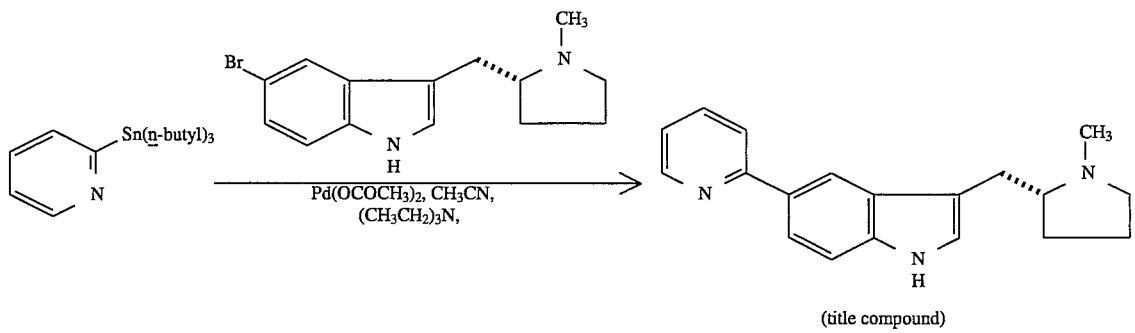

(title compound)

2-Pyridyltri-n-butylstannane and 5-bromo-3-(1-methylpyrrolidin-(R)-ylmethyl)-1H-indole (see Preparation 36) were reacted together in the presence of tri-o-tolylphosphine, triethylamine and palladium (II) acetate using a procedure similar to that described in Example 1. This yielded the title compound. Found: C,75.37; H,6.93; N,13.66; $C_{19}H_{21}N_3 \cdot \frac{1}{6}CH_2Cl_2$ requires: C,75.34; H,7.04; N, 13.75%.

$^1$H-N.M.R. (CDCl$_3$): δ=1.50–1.95(m,4H), 2.20–2.30(m, 1H), 2.45(s,3H), 2.45–2.65(m,1H), 2.65–2.75(m,1H), 3.10–3.25(m,1H), 3.25–3.30(m,1H) 5.25(s,⅓H), 7.10(s, 1H), 7.20(m,1H), 7.45(d,1H), 7.70(d,1H), 7.75(d,1H), 7.85(dd,1H), 8.10(bs,1H), 8.20(s,1H), 8.70(d,1H).

EXAMPLE 48

This Example illustrates the preparation of:

3-(1-Methylpyrrolidin-2(R)-ylmethyl)-5-(5-methoxycarbonyl-3-pyridyl)-1H-indole in the presence of tri-o-tolylphosphine, triethylamine and palladium (II) acetate using a procedure similar to that described in Example 1. This yielded the title compound as an oil. The product, which was impure, was used without characterisation in the preparation of Example 49.

EXAMPLE 49

This Example illustrates the preparation of:

5-(5-Hydroxymethyl-3-pyridyl)-3-(1-methylpyrrolidin-2(R)-ylmethyl)-1H-indole

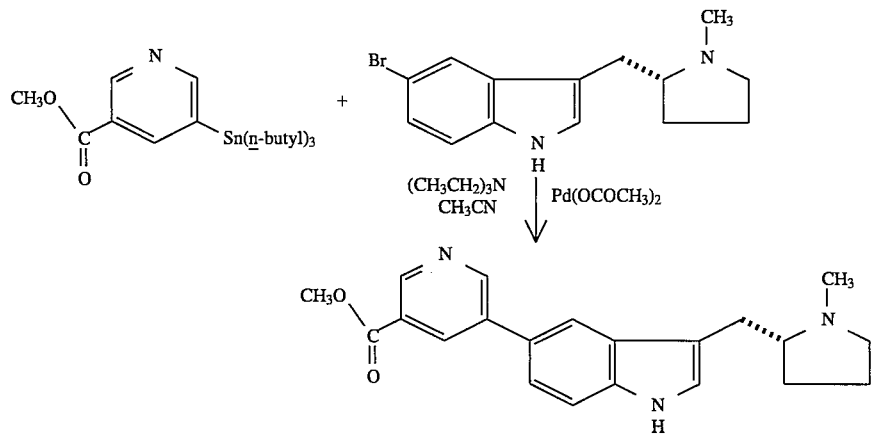

5-Methoxycarbonyl-3-pyridyltri-n-butylstannane (see Preparation and 5-bromo-3-(1-methylpyrrolidin-2(R)-ylmethyl)-1H-indole (see Preparation 36) were reacted together

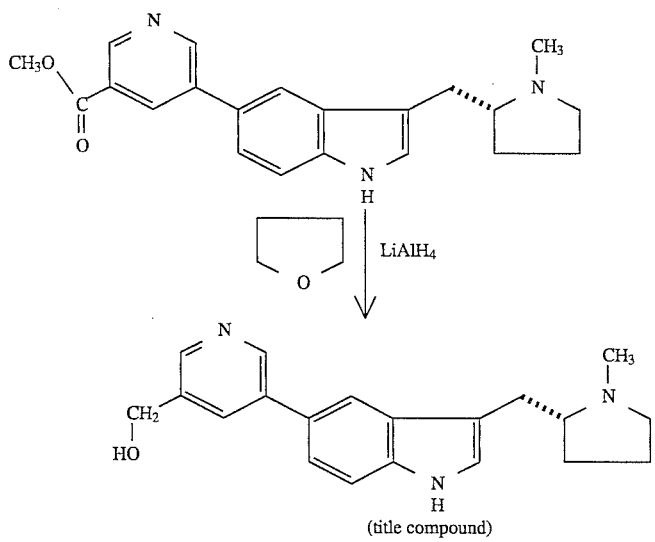

(title compound)

3-(1-Methylpyrrolidin-2(R)-ylmethyl)-5-(5-methoxycarbonyl-2-pyridyl)-1H-indole (50 mg, 0.143 mmol) (see Example 48) in tetrahydrofuran (0.7 ml) was added to a solution composed of lithium aluminium hydride in tetrahydrofuran (0.12 ml of a 1M solution) and tetrahydrofuran (0.3 ml) under nitrogen. The reaction was stirred for 1 hour at room temperature whereupon the reaction mixture was partitioned between aqueous sodium carbonate and ethyl acetate. The aqueous phase was extracted with ethyl acetate and the combined organic phases dried ($Na_2SO_4$). Evaporation of the solvent gave the crude product. This was purified by column chromatography on silica gel, eluting with dichloromethane/methanol/ammonium hydroxide (89:10:1) to afford, after combination of the appropriate fractions, the title compound (21 mg, 0.065 mmol).

LRMS, m/z=322 [MH +].

$^1$H-N.M.R. ($D_6$-DMSO): δ=1.50–1.90, 2.20–2.60(m, integral obscured by solvent), 4.60(s,s,2H), 5.35(bs,1H), 7.25(s,1H), 7.35(d,1H), 7.45(d,1H), 7.80(s,1H), 7.95(s,1H), 8.40(s,1H), 8.75(s,1H).

EXAMPLES 50 to 55

The following examples were prepared from the appropriate stannane and 5-bromo-3-(1-methylpyrrolidin-2(R)-ylmethyl)-1H-indole (see Preparation 36) using a procedure similar to that described in Example 1.

| Ex No | R | Analysis (%) | $^1$H-NMR (in $CDCl_3$ unless otherwise stated) |
|---|---|---|---|
| 50 | $H_2N-C(=O)-$ pyridyl | Found: C, 70.74; H, 6.30; N, 16.08; $C_{20}H_{22}N_4O.1/10$ $CH_2Cl_2$ requires: C, 70.41; H, 6.53; N, 16.34%. | ($D_6$,-DMSO): δ = 1.35–1.75(m, 4H), 2.00–2.10(m, 1H), 2.30(s, 3H), 2.25–2.60(m, integral obscured by solvent), 2.90–3.00(m, 1H), 3.05–3.15(m, 1H), 5.70(s, 1/5H), 7.20(s, 1H), 7.40–7.45(s, 2H), 7.60(bs, 1H), 7.90(s, 1H), 8.20(bs, 1H), 8.40(s, 1H), 8.90(s, 1H), 9.00(s, 1H). |
| 51 | $(CH_3)_2N-C(=O)-$ pyridyl | Found: C, 70.67; H, 7.33; N, 14.45; $C_{22}H_{26}N_4O.3/16$ $CH_2Cl_2$ requires: C, 70.42; H, 7.03; N, 14.81%. | δ = 1.50–1.90(m, 4H), 2.20–2.35(m, 1H), 2.50(s, 3H), 2.40–2.60(m, 1H), 2.65–2.75(m, 1H), 3.05–3.30(m, 8H), 5.30(s, 3/8H), 7.10(s, 1H), 7.40(d, 1H), 7.45(d, 1H), 7.80(s, 1H), 8.00(s, 1H), 8.20(s, 1H), 8.60(s, 1H), 8.95(s, 1H). |
| 52 | pyrimidinyl | Found: C, 73.77; H, 6.84; N, 18.62; $C_{18}H_{20}N_4.1/8H_2O$ requires: C, 73.38; H, 6.93; N, 19.02%. | δ = 1.50–1.90(m, 4H), 2.20–2.30(m, 1H), 2.50(s, 3H), 2.40–2.55(m, 1H), 2.65–2.75(m, 1H), 3.10–3.30(m, 2H), 7.10(s, 1H), 7.40(d, 1H), 7.50(d, 1H), 7.80(s, 1H), 8.60(bs, 1H), 9.00(s, 2H), 9.20(s, 1H). |
| 53 | CN-pyridyl | Found: C, 74.06; H, 5.99; N, 16.38; $C_{20}H_{20}N_4.3/8CH_2Cl_2$ requires: C, 73.64; H, 6.29; N, 16.86%. | δ = 1.50–1.90(m, 4H), 2.20–2.30(m, 1H), 2.50(s, 3H), 2.40–2.55(m, 1H), 2.60–2.75(m, 1H), 3.10–3.30(m, 2H), 5.30 (s, 3/4H), 7.10(s, 1H), 7.35(d, 1H), 7.50(d, 1H), 7.75(s, 1H), 8.15(s, s, 2H), 8.80(s, 1H), 9.10(s, 1H). |

-continued

| Ex No | R | Analysis (%) | ¹H-NMR (in CDCl₃ unless otherwise stated) |
|---|---|---|---|
| 54 | (2-pyridyl-methyl group) | Found: C, 71.16; H, 6.56; N, 17.20; $C_{18}H_{20}N_4.3/16CH_2Cl_2$ requires: C, 70.85; H, 6.66; N, 18.17%. | δ = 1.55–1.95(m, 4H), 2.20–2.30(m, 1H), 2.50 (s, 3H), 2.50–2.80(m, 2H), 3.10–3.35(m, 2H), 5.30(s, 3/8H), 7.10(d, 1H), 7.15(s, 1H), 7.05(d, 1H), 8.10(s, 1H), 8.30(dd, 1H), 8.75 (s, 1H), 8.80(d, 2H). |
| 55 | (2-cyano-4-pyridyl-methyl group) | Found: C, 69.01; H, 5.78; N, 15.48; $C_{20}H_{20}N_4.1/3CH_2Cl_2.1/2$ H₂O requires: C, 69.04; H, 6.17; N, 15.84. | δ = 1.45–1.90(m, 5H), 2.15–2.35(m, 1H), 2.45(s, 3H), 2.35–2.60(m, 1H), 2.60–2.75(m, 1H), 3.10–3.30(m, 2H), 5.30 (s, 2/3H), 7.15(s, 1H), 7.40–7.55(m, 2H), 7.75(d, 1H), 7.85 (s, 1H), 7.95(s, 1H), 8.20(bs, 1H), 8.70(d, 1H). |

EXAMPLE 56

This Example illustrates the preparation of:

3-(1-methylpyrrolidin-2(R)-ylmethyl)-5-(3-pyridyl)-1H-indole

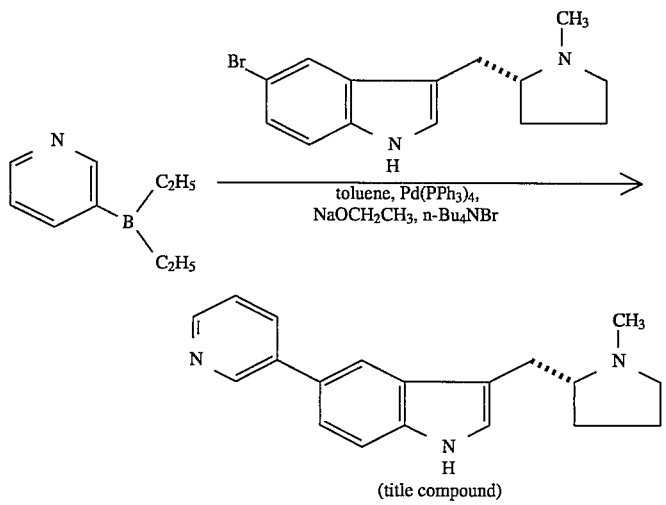

To a stirred solution of 5-bromo-3-(1-methylpyrrolidin-2(R)-ylmethyl)-1H-indole (847 mg, 2.89 mmol) (see Preparation 36) and tetrakis(triphenylphosphine)palladium(O) (116 mg, 0.10 mmol) in toluene (10 ml) under N₂ was added sequentially at room temperature tetra n-butylammonium bromide (64 mg, mmol), ethanolic sodium ethoxide (0.514 g, 7.55 mmol of sodium ethoxide in 2.8 ml of ethanol) and diethyl(3-pyridyl)borane (0.294 g, 2.00 mmol) (see Preparation 49). The reaction was refluxed for 2 hours, cooled to room temperature, diluted with ethyl acetate and washed with a 1:1 mixture of aqueous sodium carbonate and brine. The organic layer was dried (Na₂SO₄) and the solvent removed under reduced pressure to give the crude product. This was purified by column chromatography on silica gel, eluting with dichloromethane/methanol/ammonium hydroxide (89:10:1 ) to afford, after combination of the appropriate fractions, the title compound (300 mg). Found: C,75.92; H,7.36; N,13.52; $C_{19}H_{21}N_3.\!^3\!/\!_5H_2O$ requires: C,75.52; H,7.40; N,13.91%.

¹H-N.M.R. (CDCl₃): δ=1.50–2.15(m,5.2H), 2.25–2.40(m,1H), 2.47(s,3H), 2.50–2.70(m,1H), 2.70–2.80(m,1H), 3.15–3.35(m,2H), 7.15(s,1H), 7.30–7.50(m,3H), 7.80(s,1H), 7.95(d,1H), 8.25(bs,1H), 8.55(d,1H), 8.90(s,1H).

EXAMPLE 57

This Example illustrates the preparation of:

3-(1-methylpyrrolidin-2(R)-ylmethyl)-5-(4-pyridyl)-1H-indole

5-Bromo-3-(1-methylpyrrolidin-2(R)-ylmethyl)-1H-indole (see Preparation 36) and diethyl (4-pyridyl)borane (see Preparation 50) were reacted together in the presence of sodium ethoxide, n-butylammonium bromide and tetrakis(triphenylphosphine)palladium(O) using a procedure similar to that in Example 56. This gave the title compound. Found: C,75.77; H,7.16; N,13.78%; $C_{19}H_{21}N_3.\!^1\!/\!_8CH_2Cl_2$ requires: C,76.06; H,7.09; N,13.91%.

¹H-N.M.R. (CDCl₃): δ=1.50–1.90(m,4H), 2.20–2.30(m, 1H), 2.50(s,3H), 2.40–2.55(m,1H), 3.10–3.30(m,2H), 5.30(s,¼H), 7.10(s,1H), 7.45(d,1H), 7.50(d,1H), 7.60(d, 2H), 7.90(s,1H), 8.25(bs, 1H), 8.65(d,2H).

EXAMPLE 58

This Example illustrates the preparation of:

5-(5-(N-methylcarbamoyl)-3-pyridyl)-3-(1-methylpyrrolidin-2(R)-ylmethyl)-1H-indole

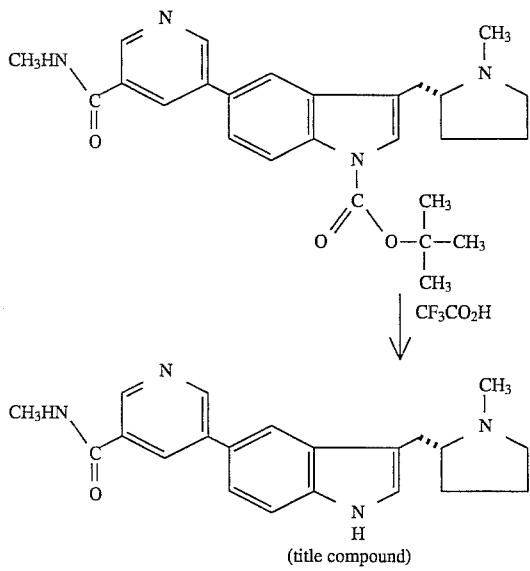

(title compound)

1-(t-Butoxycarbonyl)-5-(5-N-methycarbamoyl-3-pyridyl)-3-(1-methylpyrrolidin-2(R)-ylmethyl)-indole (88 mg, 0.20 mmol) (see Preparation was dissolved in trifluoroacetic acid (2.0 ml) and the reaction was stirred for ½ an hour at room temperature, followed by 1½ hours at reflux. The reaction was then cooled to room temperature and the trifluoroacetic acid removed by evaporation under reduced pressure followed by azetroping with dichloromethane. The residue was partitioned between ethyl acetate and aqueous sodium carbonate. The aqueous phase was extracted with ethyl acetate and the organic layers combined and dried ($Na_2SO_4$). Solvent removal under reduced pressure gave the crude product. This was purified by column chromatography on silica gel to afford, after combination of the appropriate fractions, the title compound (30 mg). Found: C,70.81; H,6.78; N,15.32; $C_{21}H_{24}N_4O.⅛CH_2Cl_2$ requires: C,70.66; H,6.81; N,15.61%.

$^1$H-N.M.R. ($CDCl_3$): δ=1.50–1.95(m,4H), 2.20–2.35(m, 1H), 2.47(s,3H), 2.45–2.65(m,1H), 2.65–2.75(m,1H), 3.07(s,s,3H), 3.10–3.30(m,2H), 5.30(s,¼H), 7.10(s,1H), 7.40–7.50(m,2H), 7.85(s,1H), 8.20(s,1H), 8.37(s,1H), 8.90(s,1H), 9.00(s,1H).

EXAMPLE 59

This Example illustrates the preparation of:

5-(6-N,N-dimethylcarbamoyl-2-pyridyl)-3-(1-methylpyrrolidin-2(R)-ylmethyl)-1H-indole

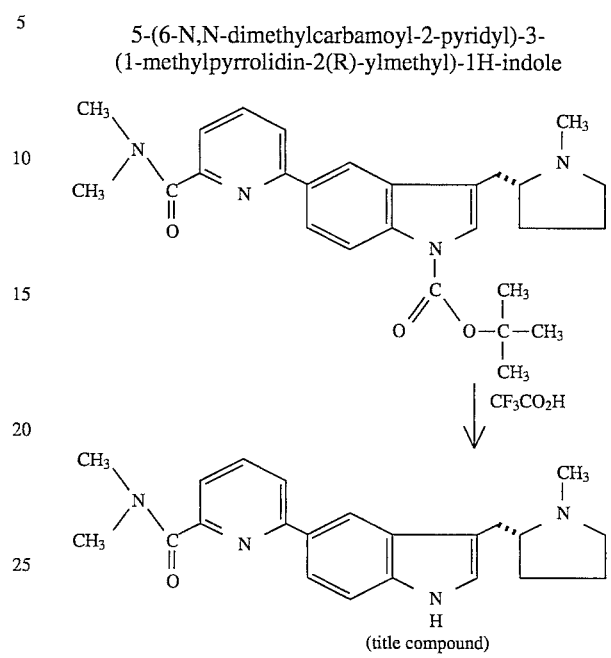

(title compound)

1-(t-butoxycarbonyl)-5-(6-N,N-dimethylcarbamoyl-2-pyridyl)-3-(1-methylpyrrolidin-2(R)-ylmethyl)-indole (see Preparation 54) was reacted with trifluoroacetic acid using a procedure similar to that described in Example 58. This yielded the title compound. Found: C,70.91%; H,7.36; N, 14.47; $C_{22}H_{26}N_4O.⅛CH_3CH_2O_2CCH_3.½H_2O$ requires: C,70.65; H,7.38; N,14.65%.

$^1$H-N..M.R. ($D_6$-DMSO): δ=1.15(t,⅜H), 1.35–1.75(m, 5H), 1.95(s,⅜H), 2.35(s,3H), 2.20–2.65(m, integral obscured by solvent), 2.80–3.10(m,2H), 3.00(s,3H), 3.05(s, 3H), 3.97(q,¼H), 7.17(s,1H), 7.30–7.50(m,2H), 7.77(d,1H), 7.90(dd,1H), 7.95(d,1H), 8.20(s,1H).

EXAMPLE 60

This Example illustrates the preparation of:

3-(1-Cyclopropylmethylpyrrolidin-2(R)-ylmethyl)-5-(5-pyrimidinyl)-1H-indole

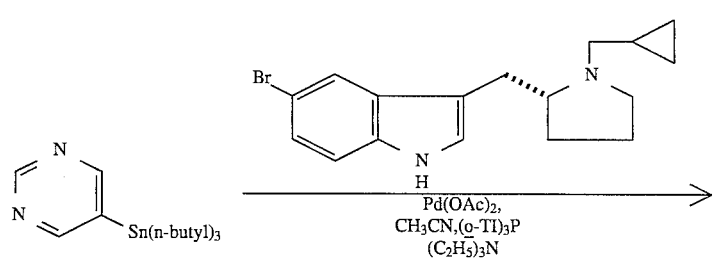

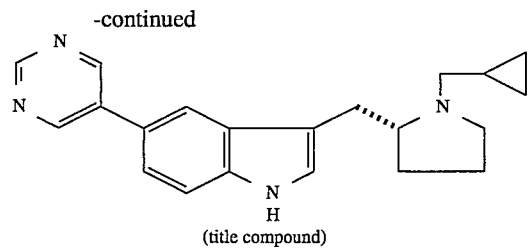

(title compound)

(5-Pyrimidinyl)tri-n-butylstannane (see Preparation 45) and 5-bromo-3-(1-cyclopropylmethylpyrrolidin-2(R)-ylmethyl)-1H-indole (see Preparation 56) were reacted together in the presence of palladium (II) acetate [Pd(OAc)$_2$], tri-o-tolylphosphine [(o-Tl)$_3$P] and triethylamine [(C$_2$H$_5$)$_3$N] using a procedure similar to that described in Example 1. This yielded the title compound. Found: C,73.72; H,7.53; N,15.84; C$_{21}$H$_{24}$N$_4$.⅛CH$_2$Cl$_2$.⅛H$_2$O requires: C,73.47; H,7.15; N,16.23%.

$^1$H-N.M.R. (CDCl$_3$): δ=0.10–0.20(m,2H), 0.40–0.60(m, 2H), 0.90–1.05(m,1H), 1.40–1.90(m,4¼H), 2.00–2.15(m, 1H), 2.20–2.40(m,1H), 2.65–3.10(m,2H), 2.90–3.00(m,1H), 3.15–3.30m,1H), 3.40–3.55(m,1H), 5.25(s,¼ 1H), 7.15(bs, 1H), 7.37(d,1H), 7.45(d,1H), 7.68(s,1H), 8.20(bs,1H), 9.00(s,2H), 9.10(s,1H).

EXAMPLE 61

This Example illustrates the preparation of:

5-(5-Carbamoyl-3-pyridyl)-3-(1-cyclopropylmethylpyrrolidin-2(R)-ylmethyl)-1H-indole $^1$H-N.M.R. (D$_6$-DMSO): δ=0.10–0.20(m,2H), 0.35–0.55(m,2H), 0.80–0.95(m,1H), 1.40–1.75(m,4H), 1.90–2.05(m,1H), 2.05–2.25(m,1H), 2.40–2.60(m, integral obscured by solvent), 2.80–2.90(m,1H), 3.05–3.15(m,1H), 3.15–3.50(m, integral obscured by solvent), 5.70(s,⅜H), 7.20(s,1H), 7.40–7.42(m,2H), 7.60(bs,1H), 7.87(s,1H), 8.25(bs, 1H), 8.40(m,1H), 8.90(d,1H), 9.00(d,1H).

EXAMPLE 62

This Example illustrates the preparation of:

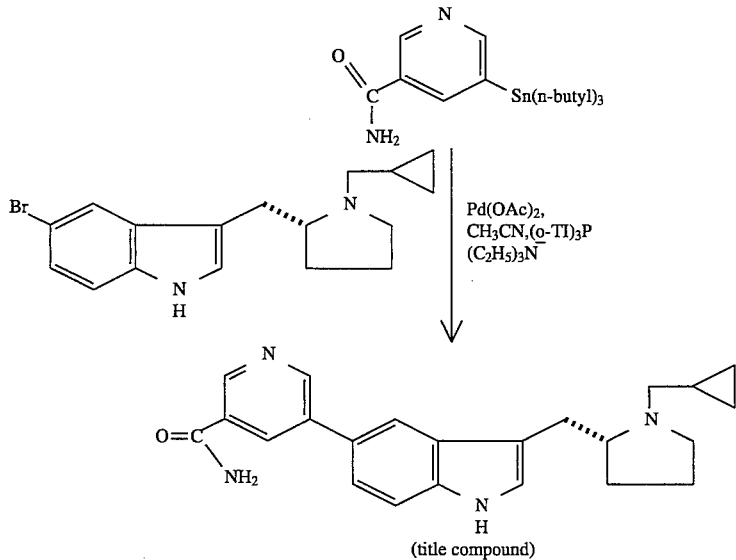

(title compound)

5-Carbamoyl-3-pyridyltri-n-butylstannane (see Preparation 43) and 5-bromo-3-(1-cyclopropylmethylpyrrolidin-2(R)-ylmethyl)-1H-indole (see Preparation 56) were reacted together in the presence of palladium (II) acetate, tri-o-tolylphosphine and triethylamine using a procedure similar to that described in Example 1. This yielded the title compound. Found: C,71.56; H,7.13; N,13.72. C$_{23}$H$_{26}$N$_4$O.³⁄₁₆CH$_2$Cl$_2$ requires: C,71.33; H,6.,81; N,14.35%.

5-(6-Methoxycarbonyl-2-pyridyl)-3-(1-methylpyrrolidin-2(R)-ylmethyl)-1H-indole

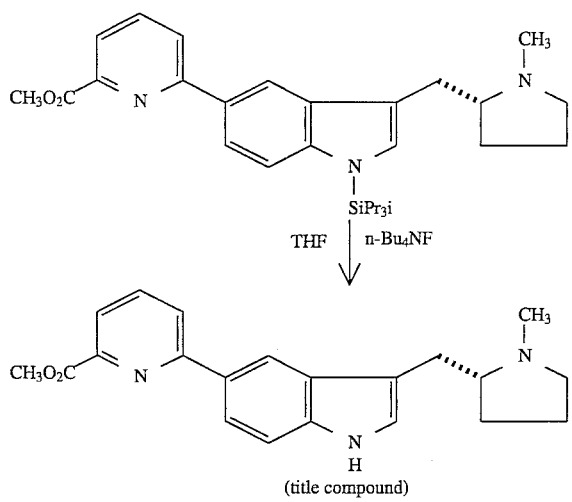

(title compound)

A solution of tetra-n-butylammonium fluoride (n-Bu₄NF) in tetrahydrofuran (1.15 ml, 1M solution, 1.15 mmol) was added in one portion to a solution of 5-(3-methoxycarbonyl-2-pyridyl)-3-(1-methylpyrrolidin-2(R)-ylmethyl)-1-triisopropylsilylindole (370 mg, 0.730 mmol) (see Preparation 60) in tetrahydrofuran (3.0 ml), under nitrogen. The reaction was halted after 15 minutes and the solvent removed under reduced pressure. The residue was dissolved in ethyl acetate and the resultant solution washed with aqueous sodium carbonate. The organic layer was dried ($Na_2SO_4$) and the solvent removed under reduced pressure. The residue was purified by column chromatography on silica gel to afford, after combination of the appropriate fractions, the title compound (200 mg) as a clear oil. Found: C,70.64; H,6.99; N,11.72. $C_{21}H_{23}N_3O_2 \cdot \frac{1}{2}H_2O$ requires: C,70.36; H,6.75; N,11.72%.

¹H-N.M.R. (CDCl₃): δ=1.50–1.95(m,5H), 2.12–2.25(m,1H), 2.45–2.60(m,1H), 2.50(s,3H), 2.60–2.80(m,1H), 3.10–3.20(m,1H), 3.20–3.35(m,1H), 4.05(s,3H), 7.05(s,1H), 7.45(d,1H), 7.85–8.02(m,4H), 8.10(ms,1H), 8.30(s,1H).

EXAMPLE 63

This Example illustrates the preparation of:

5-(6-Hydroxymethyl-2-pyridyl)-3-(1-methylpyrrolidin-2(R)-ylmethyl)-1H-indole

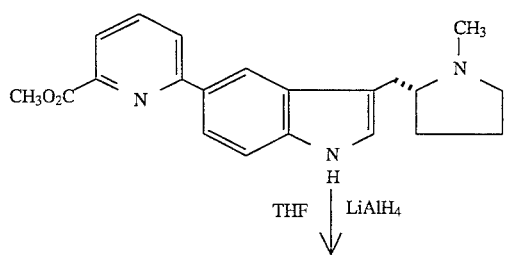

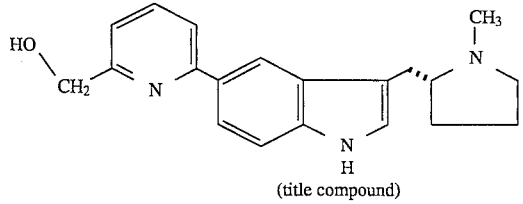

(title compound)

A solution of 5-(3-Methoxycarbonyl-2-pyridyl)-3-(1-methylpyrrolidin-2(R)-ylmethyl)-1H-indole (393 mg, 1.073 mmol) (see Example 62) in tetrahydrofuran (2.5 ml) was added dropwise, with stirring, to a flask containing a solution of lithium aluminium hydride in tetrahydrofuran (35.9 mg of LiAlH₄ in 10.0 ml THF) under a nitrogen atmosphere. The reaction was stirred for 24 hours whereupon the reaction mixture was quenched with aqueous sodium carbonate and the aqueous phase extracted with ethyl acetate. The combined organic layers were dried ($Na_2SO_4$) and the solvent removed under reduced pressure. The residue was purified by column chromatography on silica gel, eluting with dichloromethane/methanol/ammonium hydroxide (90:10:0.7), to afford, after combination and evaporation of the appropriate fractions, the title compound as a white foam (298 mg). Found: C,71.55; H,6.93; N,12.20. $C_{20}H_{22}N_3O \cdot \frac{1}{5}CH_2Cl_2$ requires: C,71.70; H,6.97; N,12.42%.

$[\alpha]_D^{25}$ +51° (c=0.1 in MeOH).

¹H-N.M.R. (CDCl₃): δ=1.55–2.00(m,4H), 2.40–2.80(m,1H), 2.50(s,3H), 2.50–2.70(m,1H), 2.70–2.85(m,1H), 3.18–3.35(m,2H), 4.82(s,2H), 5.25(s,⅖H), 7.05–7.12(m,2H), 7.45(d,1H), 7.62–7.80(m,2H), 7.88(d,1H), 8.20–8.30(m,2H).

EXAMPLE 64

This Example illustrates the preparation of:

5-(5-Carbamoyl-2-thienyl)-3-(1-methylpyrrolidin-2(R)-ylmethyl)-1H-indole

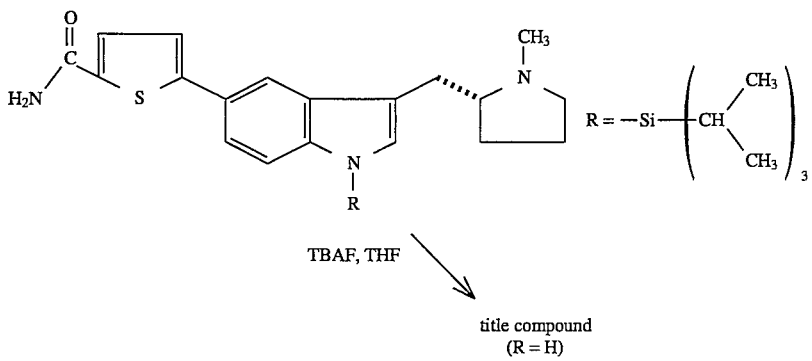

TBAF, THF title compound
(R = H)

5-(5-Carbamoyl-2-thienyl)-3-(1-methylpyrrolidin-2(R)-ylmethyl)-1-triisopropylsilylindole (see Preparation 61) was reacted with tetra-n-butylammonium fluoride in tetrahydrofuran, using a procedure similar to that described in Example 62. This yielded the title compound as an off-white foam. Found: C,64.93; H,6.33; N,11.60. $C_{19}H_{21}N_3OS \cdot \frac{3}{16}CH_2Cl_2$ requires: C,64.84; H,6.06; N,11.82%.

$^1$H-N.M.R. (D$_6$-DMSO): δ=1.40–1.80(m,4H), 2.05–2.20(m,1H), 2.35(s,3H), 2.40–2.70(m, integral obscured by solvent), 2.90–3.15(m,2H), 5.75(s,⅜H, 7.15(s,1H), 7.25–7.40(m,4H), 7.70(d,1H), 7.80(s,1H), 7.90(bs,1H), 10.95(bs,1H).

EXAMPLE 65

This Example illustrates the preparation of:

5-(5-Methoxycarbonyl-2-furyl)-3-(1-methylpyrrolidin-2(R)-ylmethyl)-1H-indole

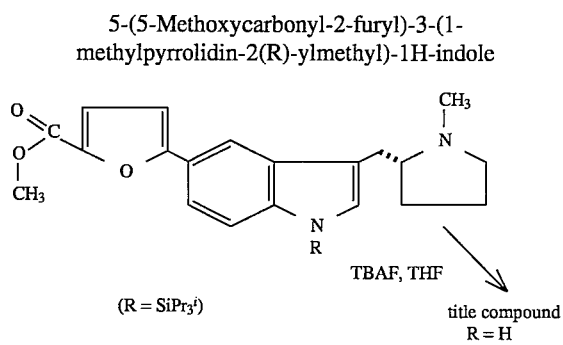

(R = SiPr₃$^i$)

TBAF, THF title compound R = H 5-(5-Methoxycarbonyl-2-furyl)-3-(1-methylpyrrolidin-2(R)-ylmethyl)-1-triisopropylsilylindole (see Preparation 62) was reacted with tetra-n-butylammonium fluoride in tetrahydrofuran, using a procedure similar to that described in Example 62. This gave the title compound as a foam. Found: C,70.74; H,6.52; N,8.47. $C_{20}H_{22}N_2O_3$ requires: C,70.98; H,6.52; N,8.28%.

$^1$H-N.M.R. (CDCl$_3$): δ=1.45–1.90(m,4H), 2.15–2.25(m,1H), 2.50(s,3H), 2.45–2.70(m,2H), 3.10–3.25(m,2H), 3.92(s,3H), 6.70(d,1H), 7.10(s,1H), 7.18–7.25(m, integral obscured by solvent), 7.40(d,1H), 7.62(d,1H), 8.00(s,1H), 8.10(bs,1H).

EXAMPLE 66

This Example illustrates the preparation of:

5-(5-Hydroxymethyl-2-furyl)-3-(1-methylpyrrolidin-2(R)-ylmethyl)-1H-indole

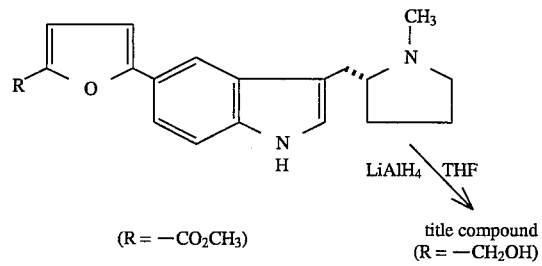

(R = —CO₂CH₃)

LiAlH₄ THF title compound
(R = —CH₂OH)

5-(5-Methoxycarbonyl-2-furyl)-3-(1-methylpyrrolidin-2(R)-ylmethyl)-1H-indole (see Example 65) was reacted with lithium aluminium hydride, in tetrahydrofuran, using a procedure similar to that described in Example 63. This gave the title compound. Found: C,70.59; H,6.81; N,8.41. $C_{19}H_{22}N_2O_2 \cdot \frac{3}{16}CH_2Cl_2$ requires: C,70.62; H,6.91; N,8.59%.

$^1$H-N.M.R. (CDCl$_3$): δ=1.50–2.10(m,4H), 2.18–2.32(m, 1H), 2.50(s,3H), 2.50–2.55 (m,1H), 2.60–2.80(m,1H), 3.10–3.30(m,2H), 4.80(s,2H), 5.30(s,⅜H), 6.40(d,1H), 6.50(d,1H), 7.02(s,1H), 7.32(d,1H), 7.50(d,1H), 7.90(s,1H), 8.02(bs,1H).

EXAMPLE 67

The in vitro evaluation of the "5-HT$_1$-like" receptor agonist activity of the compounds of the invention is carried out by testing the extent to which they mimic sumatriptan in contracting the isolated dog saphenous vein strip (P. P. A. Humphrey et al., Brit. J. Pharmacol., 1988, 94, 1123). This effect can be blocked by methiothepin, a known 5-HT antagonist. Sumatriptan is known to be useful in the treatment of migraine and produces a selective increase in carotid vascular resistance in the anaesthetized dog and a consequent decrease in carotid arterial blood flow. It has been suggested (W. Feniuk et al., Brit. J. Pharmaco., 1989, 96, 83) that this is the basis of its efficacy.

Biological activity

The following Table illustrates the in vitro activities for a range of the compounds of the invention on dog isolated saphenous vein strip. EC$_{50}$ represents the concentration of compound which causes 50% of the maximum contraction effected by it.

TABLE

| EXAMPLE | EC$_{50}$(M) | PERCENTAGE AGONISM RELATIVE TO 5-HT RESPONSE |
|---|---|---|
| 3 | $3.78 \times 10^{-9}$ | 85 |
| 37 | $7.60 \times 10^{-8}$ | 72 |
| 46 | $1.60 \times 10^{-7}$ | 78 |
| 53 | $2.60 \times 10^{-8}$ | 75 |
| 60 | $9.20 \times 10^{-9}$ | 105 |
| 64 | $2.50 \times 10^{-8}$ | 79 |
| 66 | $1.90 \times 10^{-8}$ | 80 |

The following Preparations illustrate the preparation of starting materials used in the preceding Examples:

PREPARATION 1

3-N,N-Dimethylcarbamoylphenyltri-n-butylstannane

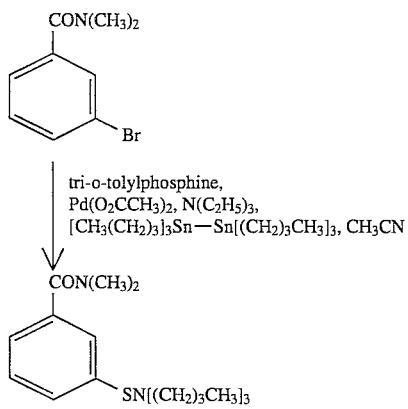

A mixture of 3-bromo-N,N-dimethylbenzamide (2.74 g, 12.01 mmol), tri-o-tolylphosphine (960 mg, 3.15 mmol), palladium (II) acetate (120 mg, 0.54 mmol), triethylamine (3.20 ml, 22.96 mmol) and hexa-n-butyldistannane (6.96 g, 4.6 ml, 12.00 mmol) in anhydrous acetonitrile (40 ml) was heated under reflux, under nitrogen, for 18 hours. The reaction mixture was then evaporated under reduced pressure and dichloromethane (25 ml) was added. The resultant solution was washed with aqueous sodium carbonate, dried (Na$_2$SO$_4$) and evaporated. The residue was purified by column chromatography on silica gel eluting initially with hexane until the tri-o-tolylphosphine and unreacted hexabutyldistannane had been eluted and then with hexane/ethyl acetate (1:1) to afford, after combination and evaporation of the appropriate fractions, the title compound as a light brown oil, (1.90 g). Found: C, 57.39; H, 8.41; N, 3.04; C$_{21}$H$_{37}$NOSn requires: C, 57.56; H, 8.51; N, 3.20%.

$^1$H-NMR (CDCl$_3$): δ=0.90 (t,9H), 1.05 (t,6H), 1.30 (m,6H), 1.52 (m,6H), 2.95 (s,3H), 3.12 (s,3H), 7.30–7.38 (m,2H), 7.40–7.55 (m,2H) ppm.

PREPARATIONS 2 TO 34

The stannane derivatives of the following tabulated Preparations were prepared by similar methods to that of Preparation 1 using the appropriate substituted bromo- or iodobenzenes as the starting materials.

The derivatives have the general formula:

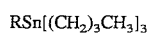

| Prep No | R | Starting material (corresponding bromo- or iodo-benzene) | Analysis (%) | $^1$H-NMR (CDCl$_3$) |
|---|---|---|---|---|
| 2 | SO$_2$NH$_2$ (para) | bromo- | — | δ = 0.90(t, 9H), 1.10(t, 6H), 1.55(m, 6H), 4.82(s, 2H), 7.62(d, 2H), 7.84(d, 2H)ppm. |
| 3 | SO$_2$NH$_2$ (meta) | bromo- | — | δ = 0.90(t, 9H), 1.10(t, 6H), 1.35(m, 6H), 1.55(m, 6H), 4.82(s, 2H), 7.46(dd, 1H), 7.68(d, 1H), 7.85(d, 1H), 8.00(s, 1H)ppm. |
| 4 | SO$_2$NHCH$_3$ (para) | bromo- | — | δ = 0.90(t, 9H), 1.10(t, 6H), 1.35(m, 6H), 1.55(m, 6H), 2.68(d, 3H), 4.38(q, 1H), 7.65 (d, 2H), 7.80(d, 2H)ppm. |
| 5 | SO$_2$NHCH$_3$ (meta) | bromo- | — | δ = 0.90(t, 9H), 1.10(t, 6H), 1.35(m, 6H), 1.55(m, 6H), 2.65(d, 3H), 4.28(q, 1H), 7.23 (dd, 1H), 7.68(d, 1H), 7.75(d, 1H), 7.95 (s, 1H)ppm. |

-continued

| Prep No | R | Starting material (corresponding bromo- or iodo-benzene) | Analysis (%) | $^1$H-NMR (CDCl$_3$) |
|---|---|---|---|---|
| 6 | 4-SO$_2$N(CH$_3$)$_2$-C$_6$H$_4$- | bromo- | — | δ = 0.90(t, 9H), 1.10(t, 6H), 1.35(m, 6H), 1.55(m, 6H), 2.70(s, 6H), 7.55–7.70(m, 4H)ppm. |
| 7 | 3-SO$_2$N(CH$_3$)$_2$-C$_6$H$_4$- | bromo- | — | δ = 0.90(t, 9H), 1.10(t, 6H), 1.35(m, 6H), 1.55(m, 6H), 2.70(s, 6H), 7.50(dd, 1H), 7.65–7.75(m, 2H), 7.90(s, 1H)ppm. |
| 8 | 4-CONH$_2$-C$_6$H$_4$- | bromo- | — | δ = 0.90(t, 9H), 1.05(t, 6H), 1.35(m, 6H), 1.55(m, 6H), 6.25(s, 2H), 7.55(d, 2H), 7.75(d, 2H)ppm. |
| 9 | 3-CONH$_2$-C$_6$H$_4$- | bromo- | — | δ = 0.90(t, 9H), 1.05(t, 6H), 1.35(m, 6H), 1.55(m, 6H), 5.90(s, 1H), 6.05(s, 1H), 7.40(dd, 1H), 7.60(d, 1H), 7.70(d, 1H), 7.90(s. 1H)ppm. |
| 10 | 4-CONHCH$_3$-C$_6$H$_4$- | bromo- | — | δ = 0.88(t, 9H), 1.05(t, 6H), 1.30(m, 6H), 1.50(m, 6H), 3.00(m, 3H), 6.15(s, 1H), 7.50(d, 2H), 7.67(d, 2H)ppm. |
| 11 | 3-CONHCH$_3$-C$_6$H$_4$- | bromo- | — | δ = 0.90(t, 9H), 1.05(t, 6H), 1.30(m, 6H), 1.55(m, 6H), 3.00(s, 3H), 6.05(s, 1H), 7.35(dd, 1H), 7.55(d, 1H), 7.65(d, 1H), 7.85(s, 1H)ppm. |
| 12 | 4-CON(CH$_3$)$_2$-C$_6$H$_4$- | bromo- | Found: C, 57.23; H, 8.45; N, 3.05; C$_{21}$H$_{37}$NOSn requires: C, 57.56; H, 8.51; N, 3.20. | δ = 0.85(t, 9H), 1.05(t, 6H), 1.32(m, 6H), 1.52(m, 6H), 3.00(s, 3H), 3.10(s, 3H), 7.35(d, 2H), 7.47(d, 2H)ppm. |
| 13 | 3-(morpholine-CO)-C$_6$H$_4$- | bromo- | Found: C, 57.73; H, 8.52; N, 2.65; C$_{23}$H$_{39}$NO$_2$Sn requires: C, 57.52; H, 8.18; N, 2.92. | δ = 0.85(t, 9H), 1.05(t, 6H), 1.30(m, 6H), 1.50(m, 6H), 3.25–3.95(m, 8H), 7.25–7.40(m, 2H), 7.45(s, 1H), 7.50(d, 1H)ppm. |
| 14 | 3-SO$_2$CH$_3$-C$_6$H$_4$- | bromo- | Found: C, 51.09; H, 7.50; N, NIL; C$_{19}$H$_{34}$O$_2$SSn requires: C, 51.26; H, 7.70; N, NIL. | δ = 0.90(t, 9H), 1.10(t, 6H), 1.30(m, 6H), 1.55(m, 6H), 3.05(s, 3H), 7.50(dd, 1H), 7.72(d, 1H), 7.85(d, 1H), 8.00(s, 1H)ppm. |

-continued

| Prep No | R | Starting material (corresponding bromo- or iodo-benzene) | Analysis (%) | $^1$H-NMR (CDCl$_3$) |
|---|---|---|---|---|
| 15 | 4-($SO_2CH_3$)-phenyl | bromo- | Found: C, 51.37; H, 7.62; N, NIL; $C_{19}H_{34}O_2SSn$ requires: C, 51.26; H, 7.70; N, NIL. | δ = 0.90(t, 9H), 1.10(m, 6H), 1.35(m, 6H), 1.55(m, 6H), 3.10(s, 3H), 7.70(d, 2H), 7.90(d, 2H)ppm. |
| 16 | 3-($SO_2CH_2CH_3$)-phenyl | bromo- | — | δ = 0.90(t, 9H), 1.10(m, 9H), 1.35(m, 6H), 1.55(m, 6H), 3.10(q, 2H), 7.50(dd, 1H), 7.75(d, 1H), 7.80(d, 1H), 7.95(s, 1H)ppm. |
| 17 | 3-($SO_2CH_2CH_2CH_3$)-phenyl | bromo- | — | δ = 0.90(t, 9H), 1.00(t, 3H), 1.15(t, 6H), 1.35(m, 6H), 1.55(m, 6H), 1.75(m, 2H), 3.10(t, 2H), 7.52(dd, 1H), 7.75(d, 1H), 7.85(d, 1H), 8.00(s, 1H)ppm. |
| 18 | 3-($CH_2SO_2CH_3$)-phenyl | bromo- | — | δ = 0.90(t, 9H), 1.05(t, 6H), 1.35(m, 6H), 1.55(m, 6H), 2.75(s, 3H), 4.12(s, 2H), 7.35–7.50(m, 4H)ppm. |
| 19 | 3-($CH_2SO_2CH_2CH_3$)-phenyl | bromo- | — | δ = 0.88(t, 9H), 1.08(t, 6H), 1.20–1.40(m, 9H), 1.55(m, 6H), 2.82(q, 2H), 4.20(s, 2H), 2.30–2.55(m, 4H)ppm. |
| 20 | 3-($SOCH_3$)-phenyl | bromo- | — | δ = 0.90(t, 9H), 1.10(t, 6H), 1.35(m, 6H), 1.55(m, 6H), 2.75(s, 3H), 7.40–7.60(m, 3H), 7.70(s, 1H)ppm. |
| 21 | 3-($SOCH_2CH_3$)-phenyl | bromo- | — | δ = 0.90(t, 9H), 1.10(t, 6H), 1.20(t, 3H), 1.35(m, 6H), 1.55(m, 6H), 2.78(m, 1H), 2.84(m, 1H), 7.40–7.65(m, 4H)ppm. |
| 22 | 4-($COCH_3$)-phenyl | iodo- | — | δ = 0.90(t, 9H), 1.10(t, 6H), 1.35(m, 6H), 1.52(m, 6H), 2.60(s, 3H), 7.58(d, 2H), 7.88(d, 2H)ppm. |
| 23 | 3-($COCH_3$)-phenyl | bromo- | Found: C, 58.61; H, 8.24; N, NIL; $C_{20}H_{34}OSn$ requires: C, 58.71; H, 8.37; N, NIL. | δ = 0.87(t, 9H), 1.10(t, 6H), 1.35(m, 6H), 1.55(m, 6H), 2.60(s, 3H), 7.40(dd, 1H), 7.65(d, 1H), 7.88(d, 1H), 8.07(s, 1H)ppm. |
| 24 | 4-($CH_2OH$)-phenyl | bromo- | Found: C, 55.74; H, 8.24; N, NIL; $C_{19}H_{34}SnO.1/5CH_2Cl_2$ requires: C, 55.68; H, 8.37; N, NIL. | δ = 0.90(t, 9H), 1.10(t, 6H), 1.40(m, 6H), 1.60(m, 7H), 4.65(d, 2H), 5.30(s, 2/5H), 7.45(d, 2H), 7.50(d, 2H)ppm. |

-continued

| Prep No | R | Starting material (corresponding bromo- or iodo-benzene) | Analysis (%) | $^1$H-NMR (CDCl$_3$) |
|---|---|---|---|---|
| 25 | 3-(CH$_2$OH)-C$_6$H$_4$- | iodo- | Found: C, 56.82; H, 8.45; N, NIL; C$_{19}$H$_{34}$SnO requires: C, 57.00; H, 8.56; N, NIL. | δ = 0.88(t, 9H), 1.05(t, 6H), 1.35(m, 6H), 1.55(m, 6H), 4.68(d, 2H), 7.08–7.50(m, 4H)ppm. |
| 26 | 3-(CO$_2$CH$_3$)-C$_6$H$_4$- | bromo- | — | δ = 0.90(t, 9H), 1.10(t, 6H), 1.35(m, 6H), 1.55(m, 6H), 3.92(s, 3H), 7.19(dd, 1H), 7.65(d, 1H), 7.95(d, 1H), 8.13(s, 1H)ppm. |
| 27 | 4-(CH$_2$NHSO$_2$CH$_2$CH$_3$)-C$_6$H$_4$- | bromo- | Found: C, 51.78; H, 8.00; N, 2.64; C$_{21}$H$_{39}$NO$_2$SSn requires C, 51.66; H, 8.05; N, 2.87. | δ = 0.88(t, 9H), 1.05(t, 6H), 1.20–1.40(m, 9H), 1.50 (m, 6H), 2.95 (q, 2H), 4.30(d, 2H), 4.45(m, 1H), 7.28 (d, 2H), 7.48(d, 2H)ppm. |
| 28 | 4-(CN)-C$_6$H$_4$- | iodo- | — | δ = 0.90(t, 9H), 1.10(t, 6H), 1.30(m, 6H), 1.50(m, 6H), 7.55–7.65(m, 4H). |
| 29 | 4-(CH$_2$C(O)NH$_2$)-C$_6$H$_4$- | bromo- | — | δ = 0.90(t, 9H), 1.10(t, 6H), 1.30(m, 6H), 1.50(m, 6H), 3.60(s, 2H), 5.40(s, 1H), 5.65(s, 1H), 7.20(d, 2H), 7.45(d, 2H). |
| 30 | 4-(C(CH$_3$)$_2$OH)-C$_6$H$_4$- | iodo- | — | δ = 0.90(t, 9H), 1.10(t, 6H), 1.30(m, 6H), 1.40–1.60(m, 6H), 1.55(s, 6H), 7.35–7.45(m, 4H). |
| 31 | 3-(CN)-C$_6$H$_4$- | bromo- | — | δ = 0.90(t, 9H), 1.10(t, 6H), 1.35(m, 6H), 1.50(m, 6H), 7.40(dd, 1H) 7.55(d, 1H), 7.70(d, 1H), 7.75(s, 1H). |
| 32 | 3-(CH$_2$C(O)N(CH$_3$)$_2$)-C$_6$H$_4$- | iodo- | Found: C, 56.30; H, 8.45; N, 2.90; C$_{22}$H$_{39}$NOSn.H$_2$O requires C, 56.19; H, 8.78; N, 2.97. | δ = 0.90(t, 9H), 1.10(t, 6H), 1.35 (m, 6H), 1.55(m, 6H), 2.98(s, 3H), 3.00(s, 3H), 3.75(s, 2H), 7.15–7.45(m, 4H). |
| 33 | 3-(C(O)NHC$_2$H$_5$)-C$_6$H$_4$- | bromo- | — | δ = 0.85(t, 9H), 1.10(t, 6H), 1.20–1.45(m, 9H), 1.50 (m, 6H), 3.50(q, 2H), 6.00(s, 1H), 7.35(dd, 1H), 7.58 (d, 1H), 7.60(d, 1H), 7.85(s, 1H). |
| 34 | 4-(CH(OH)CH$_3$)-C$_6$H$_4$- | bromo- | — | δ = 0.90(t, 9H), 1.10(t, 6H), 1.30(m, 6H), 1.40–1.55 (m, 9H), 1.80(d, 1H), 7.35(d, 2H), 7.45(d, 2H). |

PREPARATION 35

3-(1-Benzyloxycarbonylpyrrolidin-2(R)-ylcarbonyl)-5-bromo-1H-indole

To a stirred solution of N-benzyloxycarbonyl-D-proline (1.0 g) in anhydrous dichloromethane (2 ml) and N,N-dimethylformamide (1 drop) was added oxalyl chloride (0.5 ml) and the resulting solution was stirred at room temperature for 1.5 hours. The solution was evaporated under reduced pressure and remaining solvent was removed under high vacuum to give the acid chloride of N-benzyloxycarbonyl-D-proline.

In a separate flask a solution of ethylmagnesium bromide (1.4 ml of a 3M solution in diethyl ether) was added dropwise over 5 minutes to a stirred solution of 5-bromoindole (0.75 g) in dry diethyl ether (18 ml). The mixture was stirred at room temperature for 10 minutes, heated under reflux for 2 hours, then cooled to −30° C. A solution of the above acid chloride of N-benzyloxycarbonyl-D-proline in dry diethyl ether (4 ml) was then added dropwise with stirring and stirring was continued for a further 1 hour. Diethyl ether (12.5 ml) and saturated aqueous sodium bicarbonate (6.5 ml) were added and the reaction was allowed to warm to room temperature. Stirring was continued for a further 10 minutes and the mixture was filtered. The solid was washed with ethyl acetate and the combined filtrate and washings were washed with water then brine and dried (MgSO$_4$). Evaporation of the solvent gave an oil which was chromatographed on silica gel. Elution with ethyl acetate gave, after combination and evaporation of the appropriate fractions, the title compound as a foam, (0.82 g). Found: C,58.85; H,4.51; N,6.38; C$_{21}$H$_{19}$BrN$_2$O$_3$ requires: C,59.02; H,4.48; N,6.56%.

LRMS, m/z (relative intensity)=428 [M+with $^{81}$BR] (5), 426 [M+with $^{79}$Br] (5), 224 (19), 222 (21), 204 (62), 160 (68), 91 (100).

PREPARATION 35B

3-(1-Benzyloxycarbonylpyrrolidin-2(R)-ylmethyl)-5-bromo-1H-indole

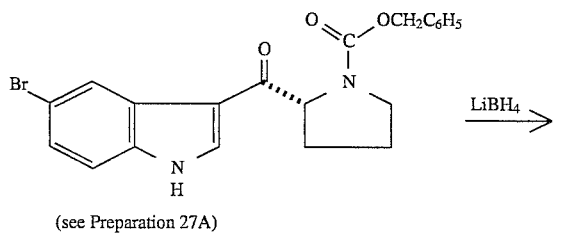

(see Preparation 27A)

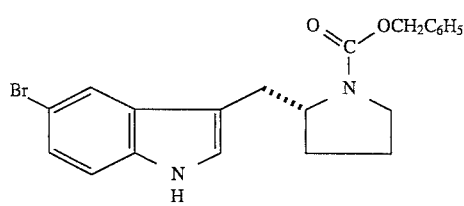

3-(1-Benzyloxycarbonylpyrrolidin-2(R)-ylcarbonyl)-5-bromo-1H-indole (0.67 g, 1.57 mmol) (see Preparation 35) was dissolved in dry tetrahydrofuran (20 ml) and, at room temperature, under nitrogen, lithium borohydride (2M solution in tetrahydrofuran; 1.2 ml, 2.4 mmol) was added. The reaction mixture was stirred at room temperature for 3 hours, heated under reflux for 16 hours, then allowed to cool to room temperature. 2N Hydrochloric acid (10 ml) was added dropwise and the reaction mixture then partitioned between ethyl acetate and water. The separated organic phase was washed with saturated aqueous sodium bicarbonate solution (twice) and brine (once), dried (Na$_2$SO$_4$), and evaporated under reduced pressure to give a colourless oil. Purification by column chromatography on silica gel, eluting with dichloromethane, gave the title compound as an oil (0.32 g). Found: C,59.94; H,5.07; N,6.58. C$_{21}$H$_{21}$BrN$_2$O$_2$.$^{1}/_{10}$CH$_2$Cl$_2$ requires: C,60.08; H,5.07; N,6.64%.

$^1$H-N.M.R. (CDCl$_3$) (consistent with the compound existing as a mixture of two rotamers): δ=1.63–1.90(m,4H), 2.60–2.82(m,1H), 3.10–3.28 (m,1H), 3.30–3.54(m,2H), 4.18(m,1H), 5.15–5.25(m,2H), 5.30(s,⅓H), 6.90 and 6.95 (s,s,1H), 7.05–7.50(m,7H), 7.70 and 7.85(s,s,1H), 8.25(bs, 1H).

PREPARATION 36

5-Bromo-3-(1-methypyrrolidin-2(R)-ylmethyl)-1H-indole

A solution of 3-(1-benzyloxycarbonylpyrrolidin-2(R)-ylcarbonyl)-5-bromo-1H-indole (1.04 g) (see Preparation 35) in dry tetrahydrofuran (20 ml) was added dropwise to a stirred suspension of lithium aluminium hydride (0.27 g) in dry tetrahydrofuran (15 ml) at room temperature under an atmosphere of dry nitrogen. The mixture was heated under reflux with stirring for 18 hours and then cooled. Additional lithium aluminium hydride (50 mg) was added and the mixture heated under reflux for an additional 3 hours. The mixture was again cooled, lithium aluminium hydride (40 mg) was added and the mixture heated under reflux for a further 18 hours. The mixture was cooled, water (0.44 ml) was carefully added with stirring followed by 20% aqueous sodium hydroxide (0.44 ml) and then more water (1.33 ml). The mixture was diluted with ethyl acetate and filtered through a cellulose-based filter aid. The filtrate was washed with water then brine and dried (Na$_2$SO$_4$). Evaporation of the solvent gave an oil which was chromatographed on silica gel. Elution with dichloromethane/ethanol/concentrated aqueous ammonia (90:10:0.5) gave, after combination and evaporation of the appropriate fractions, the title compound as a solid, (0.51 g). A small sample was crystallised from dichloromethane/hexane, m.p. 137°–140° C. Found: C, 56.65; H,5.69; N,9.23; C$_{14}$H$_{17}$N$_2$Br.0.25 H$_2$O requires: C,56,48; H,5,93; N,9.41%.

$^1$H-NMR (DMSO-d$_6$): δ=1.38–1.73 (m,4H), 2.09 (dd,J= 8.7 and 17.3 Hz, 1H), 2.33 (s,3H), 2.26–2.36 (m,1H), 2.47 (dd,J=9.2 and 14.0 Hz, 1H), 2.94–3.03 (m,2H), 7.16 (dd,J= 1.8 and 8.6 Hz, 1H), 7.21 (br d, 1H), 7.31 (d,J=8.6 Hz, 1H), 7.65 (br d,1H), 11.05 (br s,1H) ppm.

[α]$_D^{25}$=+62° (c=0.10 in methanol).

PREPARATION 37

3-(1-Benzyloxycarbonylpyrrolidin-2(R)-ylmethyl)-5-(3-N,N-dimethylcarbamoylphenyl)-1H-indole A mixture of 3-N,N-dimethylcarbamoylphenyltri-n-butylstannane (see Preparation 13) (1.315 g, 3.00 mmol), tri-o-tolylphosphine (240 mg, 0.788 mmol), palladium (II) acetate (30 mg, 0.134 mmol), triethylamine (0.80 ml, 5.74 mmol) and 3-(1-benzyloxycarbonylpyrrolidin-2(R)-ylmethyl)-5-bzromo-1H-indole (1.124 g, 2.72 mmol) (see Preparation 35B) were reacted together using a procedure similar to that described for Example 1. This yielded the title compound as a pale yellow foam (482 mg). Found: C,72.47; H,6.21; N,8.10; C₃₀H₃₁N₃O₃.¼CH₂Cl₂ requires: C,72.26; H,6.31; N,8.36%.

[α]$_D^{25}$=28° (c=0.1 in methanol).

¹H-N.M.R. (CDCl₃) (consistent with the compound existing as two rotamers): δ=1.60–2.00(m,4H), 2.70–2.90(m, 1H), 2.90–3.55(m,8H), 4.20–4.30(m,1H), 5.10–5.30(m,2H), 5.30(s,½H), 6.95, 7.10(s,s,1H), 7.15–7.30(m, integral obscured by solvent), 7.30–7.50(m,8H), 7.50–7.75(m,2H), 7.80, 7.95(s,s, 1H), 8.25(s,1H).

PREPARATION 38

3-(1-Benzyloxycarbonylpyrrolidin-2(R)-ylmethyl)-5-(3-hydroxymethylphenyl)-1H-indole 3-Hydroxymethylphenyltri-n-butylstannane (2.016 g, 5.076 mmol) (see Preparation 25) and 3-(1-benzyloxycarbonylpyrrolidin-2(R)-ylmethyl)-5-bromo-1H-indole (1.902 g, 4.602 mmol) (see Preparation 35B) were reacted together in the presence of tri-o-tolylphosphine, triethylamine and palladium (II) acetate using a procedure similar to that described in Example 1. This yielded the title compound as a white foam (1.050 g). Found: C,75.58; H,6.51; N,5.88; C₂₈H₂₈N₂O₃.¹/₁₂CH₂Cl₂ requires: C,75.36; H,6.34; N,6.26%.

[α]$_D^{25}$=−22° (C=0.1 in methanol).

¹H-N.M.R. (CDCl₃) (consistent with the compound existing as two rotamers): δ=1.65–2.00(m,4H), 2.50(s,1H), 2.80–2.90(m,1H), 3.15–3.30(m,1H), 3.30–3.55(m,2H), 4.20–4.30(m,1H), 4.70–4.80(m,1H), 5.10–5.30(m,2⅙H), 6.95, 7.00(s,s,1H), 7.00–7.70(m, integral obscured by solvent), 7.80, 8.00(s,s,1H), 8.10(s,1H).

PREPARATION 39

3-(1-Benzyloxycarbonyloyrrolidin-2(R)-ylmethyl)-5-(4-hydroxymethylphenyl)-1H-indole 4-Hydroxymethylphenyltri-n-butylstannane (1.008 g, 2.538 mmol) (see Preparation 24) and 3-(1-benzyloxycarbonylpyrrolidin-2(R)-ylmethyl)-5-bromo-1H-indole (0.951 g, 2.301 mmol) (see Preparation 35B) were reacted together in the presence of tri-o-tolylphosphine, triethylamine and palladium (II) acetate using a procedure similar to that described in Example 1. This yielded the title compound as a white foam (450 mg). Found: C,74.61; H,6.49; N,5.63; C₂₈H₂₈N₂O₃.³/₂₀ CH₃CH₂OCOCH₃.¹/₁₀CH₂Cl₂ requires: C,74.57; H,6.43; N,6.02%.

¹H-N.M.R. (CDCl₃) (consistent with the compound existing as two rotamers): δ=1.30(t,³/₁₀H), 1.45–2.00(m,4⁹/₂₀H), 2.65–2.95(m,1H), 3.15–3.55(m,3⁹/₂₀H), 4.15–4.35(m,1H), 4.70(bs,2H), 5.10–5.30 (m,2⅕H), 6.90, 7.00(s,s,1H), 7.05–7.75(m, integral obscured by solvent), 7.80, 7.95(s,s, 1H), 8.25.

PREPARATION 40

3-(1-Benzyloxycarbonylpyrrolidin-2(R)-ylmethyl)-5-(3-carbamoylphenyl)-1H-indole 3-carbamoylphenyltri-n-butylstannane (3.076 g, 7.50 mmol) (see Preparation 9) and 3-(1-benzyloxycarbonylpyrrolidin-2(R)-ylmethyl)-5-bromo-1H-indole (2.81 g, 6.80 mmol) (see Preparation 35B) were reacted together in the presence of tri-o-tolylphosphine, triethylamine and palladium (II) acetate using a procedure similar to that described in Example 1. This yielded the title compound as a pale yellow foam (954 mg). Found: C,68.45; H,5.92; N,8.10; C₂₈H₂₇N₃O₃. ⁷/₁₂CH₂Cl₂ requires: C,68.24; H,5.64; N,8.35%.

¹H-N.M.R. (CDCl₃) (consistent with the compound existing as two rotamers): δ=1.50–2.05(m,4H), 2.65–3.00(m, 1H), 3.00–3.20(m,1H), 3.20–3.50(m,2H), 4.30–4.40(m,1H), 5.00–5.30(m,4⅙H), 5.40–5.80(bs,1H), 7.00–8.10(m, integral obscured by solvent), 8.15, 8.25(s,s,1H), 8.20, 8.30(s,s,1H).

PREPARATION 41

3-(1-Benzyloxycarbonylpyrrolidin-2(R)-ylmethyl)-5-(4-carbamoylphenyl)-1H-indole 4-carbamoylphenyltri-n-butylstannane (1.833 g, 4.469 mmol) (see Preparation 8) and 3-(1-benzyloxycarbonylpyrrolidin-2(R)-ylmethyl)-5-bromo-1H-indole (1.67 g, 4.05 mmol) (see Preparation 35B) were reacted together in the presence of tri-o-tolylphosphine, triethylamine and palladium (II) acetate using a procedure similar to that described in Example 1. This yielded the title compound as an off-white foam (541 mg). Found: C,71.64; H,6.02; N,8.57; C₂₈H₂₇N₃O₃. ¼CH₂Cl₂ requires: C,71.84; H,5.84; N,8.85%.

¹H-N.M.R. (CDCl₃) (consistent with the compound existing as two rotamers): δ=1.65–1.90(m,4H), 2.60–2.90(m, 1H), 3.20–3.50(m,3H), 4.20–4.30(m,1H), 5.00–5.30(m, 2½H), 5.55(bs,1H), 6.10(bs,1H), 7.00, 7.05(s,s, 1H), 7.15–7.50(m, integral obscured by solvent), 7.60, 7.70(d,d, 2H), 8.00–7.90(m,3H), 8.10(s,1H).

PREPARATION 42

5-Methoxycarbonyl-3-pyridyltri-n-butylstannane

3-Bromo-5-methoxycarbonylpyridine was reacted with hexa(n-butyl)distannane in the presence of tri-o-tolylphosphine, triethylamine and palladium (II) acetate using a procedure similar to that described in Preparation 1. The product, which was impure, was used without characterisation in the preparation of Example 48.

PREPARATION 43

5-Carbamoyl-3-pyridyltri-n-butylstannane

3-Bromo-5-carbamoylpyridine was reacted with hexa(n-butyl)distannane in the presence of tri-o-tolylphosphine, triethylamine and palladium (II) acetate using a procedure similar to that described in Preparation 1. This yielded the title compound. Found: C,52.30; H,7.59; N,6.52; C₁₈H₃₂N₂OSn requires: C,52.58; H,7.85; N,6.81.

¹H-N.M.R. (d₆-DMSO): δ=0.85(t,9H), 1.10(t,6H), 1.15–1.35(m,6H), 1.45–1.60(m,6H), 7.55(bs,1H), 8.15(bs, 1H), 8.20(s,1H), 8.65(s,1H), 8.60(s,1H), 8.90(s,1H).

PREPARATIONS 44 to 48

The stannane derivatives of the following tabulated preparations were prepared by similar methods to that of Preparation 1 using the appropriate bromoheteroaromatic starting materials, and they have the following general formula:

RSn[(CH₂)₃CH₃]₃

| Prep No | R | Analysis (%) | ¹H-NMR (CDCl₃) |
|---|---|---|---|
| 44 | ![structure: 4-methylpyridine with C(=O)N(CH₃)₂ at 3-position] | — | δ = 0.90(t, 9H), 1.10(t, 6H), 1.25–1.40(m, 6H), 1.45–1.60(m, 6H), 3.00(s, 3H), 3.15(s, 3H), 7.80(s, 1H), 8.55(s, 1H), 8.60(s, 1H). |
| 45 | ![structure: 4-methylpyrimidine] | — | δ = 0.90(t, 9H), 1.15(t, 6H), 1.30–1.40(m, 6H), 1.45–1.60(m, 6H), 8.65(s, 2H), 9.10(s, 1H). |
| 46 | ![structure: 4-methylpyridine with CN at 3-position] | — | δ = 0.85(t, 9H), 1.10(t, 6H), 1.20–1.40(m, 6H), 1.40–1.65(m, 6H), 7.95(s, 1H), 8.95(s, s, 2H). |
| 47 | ![structure: 2-methylpyrazine] | — | δ = 0.85(t, 9H), 1.15(t, 6H), 1.25–1.40(m, 6H), 1.45–1.65(m, 6H), 7.10(dd, 1H), 8.65(d, 2H). |
| 48 | ![structure: 4-methyl-2-cyanopyridine] | — | δ = 0.85(t, 9H), 1.15(t, 6H), 1.20–1.45(m, 6H), 1.45–1.70(m, 6H), 7.55(d, 1H), 7.75(s, 1H), 8.55(d, 1H). |

PREPARATION 49

Diethyl(3-pyridyl)borane

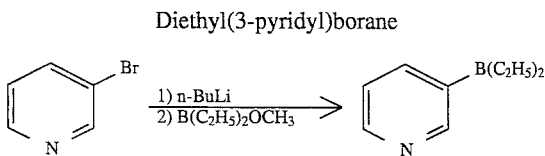

n-Butyllithium (25.6 ml of a 2.5M solution in hexanes, 64 mmol) was added as a rapid stream of droplets to a solution of 3-bromopyridine (10.04 g, 64 mmol) in ether (200 ml) at −40° C., under nitrogen. The addition was carried out over 5 minutes and the reaction temperature was maintained below −40° C. throughout. The reaction was stirred at −40° C. for 20 minutes and then cooled to −70° C. whereupon diethylmethoxyborane in tetrahydrofuran (64.0 ml of a 1M solution, 64 mmol) was added as a rapid stream of droplets over 5 minutes. The reaction temperature was maintained below −63° C. throughout this addiition. The reaction was then allowed to warm slowly to room temperature whereupon it was diluted with ethylacetate and washed with brine. The organic layer was dried (Na₂SO₄) and the solvent removed under reduced pressure to give the crude product. This was purified by column chromatography on silica gel, eluting with dichloromethane to afford, after combination and evaporation of the appropriate fractions, the title compound as a yellow crystalline solid (7.3 g). Found: C,73.40; H,9.53; N,8.92; C₉H₁₄NB requires: C,73.52; H,9.60; N,9.53%.

¹H-N.M.R. (CDCl₃): δ=0.40(t,6H), 0.50–0.75(m,4H), 7.15–7.30(m, integral obscured by solvent), 7.55(s,1H), 7.70(d,1H), 8.00(d,1H).

PREPARATION 50

Diethyl(4-pyridyl)borane

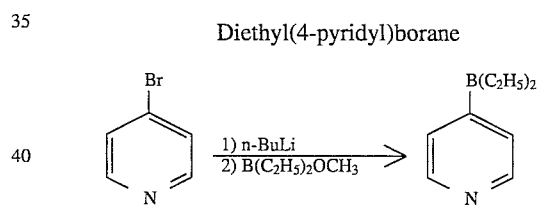

4-Bromopyridine was reacted with n-butyllithium and then with diethylmethoxyborane using a procedure similar to that in Preparation 49. This gave the title compound, which was used without characterisation.

PREPARATION 51

5-Bromo-1-(t-butoxycarbonyl)-3-(1-methylpyrrolidin-2(R)-ylmethyl)-indole

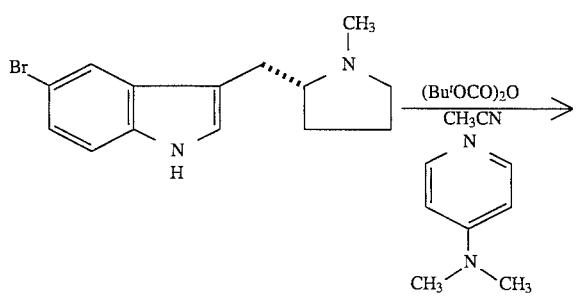

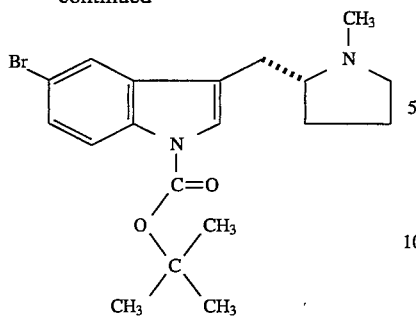

To a stirred solution of 5-bromo-3-(1-methylpyrrolidin-2(R)-ylmethyl)-1H-indole (199 mg, 0.68 mmol) (see Preparation 36) in acetonitrile (4.0 ml) under nitrogen was added a solution of di-t-butyldicarbonate (296 mg, 1.36 mmol) in acetonitrile (1.0 ml). 4-N,N-Dimethylaminopyridine (83 mg, 0.68 mmol) was then added in one portion. The reaction was stirred for 16 hours at room temperature whereupon the solvent was removed under reduced pressure to give the crude product. This was purified by column chromatography on silica gel to afford, after combination of the appropriate fractions, the title compound (240 mg). Found: C,56.37; H,6.38; N,6.74; $C_{19}H_{25}N_2O_2Br \cdot 3/16 CH_2Cl_2$ requires C,56.31; H,6.25; N,6.85%.

$^1$H-N.M.R. (CDCl$_3$): δ=1.65(s,9H), 1.40–1.90(m,4H), 2.15–2.30(m,1H), 2.45(s,3H), 2.35–2.55(m,2H), 2.95–3.17(m,2H), 5.30(s,⅜H), 7.15–7.20 (m,2H), 7.65(s, 1H), 7.95(bs, 1H).

PREPARATION 52

1-(t-butoxycarbonyl)-3-(1-methylpyrrolidin-2(R)-ylmethyl)-5-(tri-n-butylstannyl)-indole

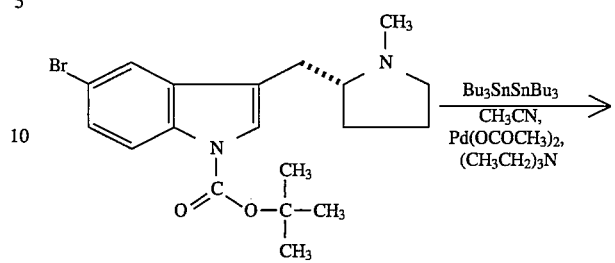

5-Bromo-1-(t-butyloxycarbonyl)-3-(1-methylpyrrolidin-2(R)-ylmethyl)-indole (see Preparation 51 ) was reacted with hexa(n-butyl)distannane in the presence of tri-o-tolyphosphine, triethylamine and palladium (II) acetate using a procedure similar to that described in Preparation 1. This yielded the title compound.

$^1$H-N.M.R. (CDCl$_3$): δ=0.85(t,9H), 1.10(t,6H), 1.15–1.40(m,6H), 1.40–1.95(m,10H), 1.65(s,9H), 2.15–2.30(m,1H), 2.50(s,3H), 2.40–2.65 (m,2H), 3.05–3.40(m,2H), 7.30–7.45(m,2H), 7.60(s,1H), 8.05(bs, 1H).

PREPARATION 53

1-(t-butoxycarbonyl)-5-(5-N-methylcarbamoyl-3-pyridyl)-3-(1-methylpyrrolidin-2(R)-ylmethyl)-indol

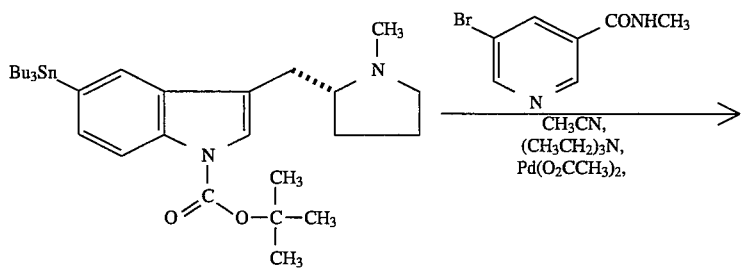

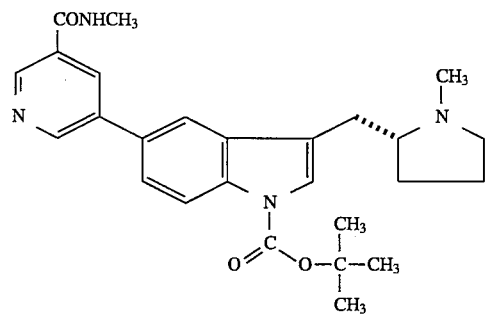

1-(t-Butoxycarbonyl)-3-(1-methylpyrrolidin-2(R)-ylmethyl)-5-(tri-n-butylstannyl)-indole (see Preparation 52) was reacted with 3-bromo-5-(N-methylcarbamoyl)pyridine in the presence of tri-o-tolylphosphine, triethylamine and palladium (II) acetate using a procedure similar to that described in Example 1. This yielded the title compound. Found: C,66.88; H,6.42; N,11.69; $C_{26}H_{32}N_4O_3 \cdot 7/24 CH_2Cl_2$ requires: C,66.71; H,6.94; N,11.84%.

$^1$H-N.M.R. (CDCl3): δ=1.55–1.95(m,4H), 2.20–2.35(m, 1H), 2.45(s,3H), 2.40–2.60(m,1H), 2.65–2.75(m,1H), 3.10(s,s,3H), 3.10–3.30(m,2H), 5.30(s,7/12H), 6.37(bs,1H), 7.10(s,1H), 7.40–7.50(m,2H), 7.85(s,1H), 8.20(s,1H), 8.37(s,1H), 8.87(s,1H), 9.00(s,1H).

PREPARATION 54

1-(t-butoxycarbonyl)-5-(6-N,N-dimethylcarbamoyl-2-pyridyl)-3-(1-methylpyrrolidin-2(R)-ylmethyl)-indole

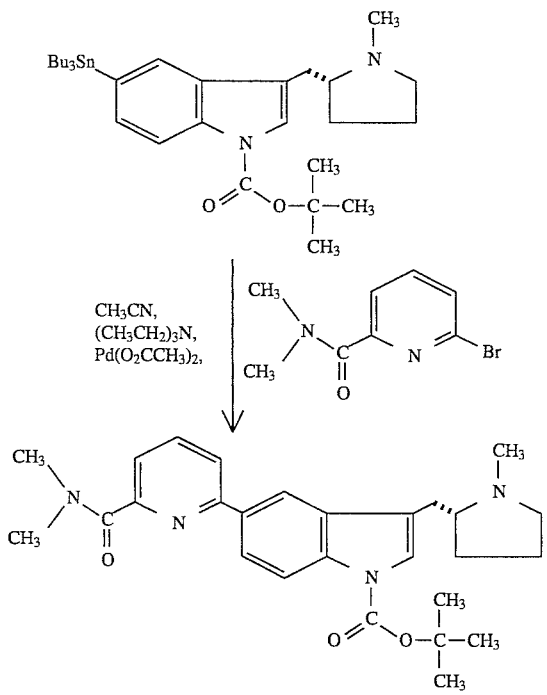

1-(t-Butoxycarbonyl)-3-(1-methylpyrrolidin-2(R)-ylmethyl)-5-(tri-n-butylstannyl)-indole (see Preparation 52) was reacted with 2-bromo-6-(N,N-dimethylcarbamoyl)pyridine in the presence of tri-o-tolylphosphine, triethylamine and palladium (II) acetate using a procedure similar to that described in Example 1. This yielded the title compound. Found: C,68.94; H,7.28; N,11.46; $C_{27}H_{34}N_4O_3 \cdot 1/8 CH_2Cl_2$ requires: C,68.85; H,7.30; N,11.84%.

$^1$H-N.M.R. (CDCl$_3$): δ=1.45–1.95(m,4H), 1.65(s,9H), 2.17–2.30(m,1H), 2.47(s,3H), 2.50–2.70(m,2H), 3.10–3.30(m,2H), 3.20(s,3H), 3.25(s,3H), 5.30(s,¼H), 7.40(s,1H), 7.60(d,1H), 7.75–7.90(m,2H), 7.95(d,1H), 8.15–8.25(m,2H).

PREPARATION 55

5-Bromo-3-(pyrrolidin-2(R)-ylmethyl)-1H-indole

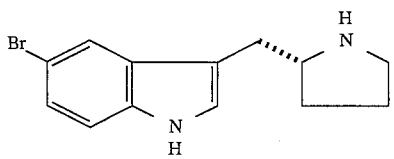

A) To 3-(1-benzyloxycarbonylpyrrolidin-2(R)-ylmethyl)-5-bromo-1H-indole (see Preparation 35B) (10.0 g, 24.2 mmol) was added dropwise hydrogen bromide/acetic acid (36% w/w) (17 ml) at 0° C., with stirring. After 50 minutes at 0° C. the solvent was removed by evaporation under reduced pressure, and the residue azeotroped with toluene. The resulting oil was partitioned between dichloromethane and 2M aqueous sodium carbonate. The separated aqueous phase was re-extracted with dichloromethane and the combined organic phases dried (Na$_2$SO$_4$) and evaporated under reduced pressure. Purification by column chromatography on silica gel, eluting with a gradient of dichloromethane:methanol:0.88 aqueous ammonia (95:5:0 to 95:5:2), yielded the title compound as an oil (2.01 g). Found: C,54.75; H,5.41; N,9.63. $C_{13}H_{15}BrN_2 \cdot 1/5 CH_2Cl_2$ requires: C,54.84; H,5.37; N,9.67%.

[α]$_D^{25}$=–9° (c=0.1 in methanol).

$^1$H-N.M.R. (CDCl$_3$): δ=1.35–1.50(m,1H), 1.68–1.98(m, 3H), 2.45(bs,1H), 2.72–2.92(m,3H), 2.96–3.08(m,1H), 3.28–3.43(m,1H), 5.28(s,⅖H), 7.06(s,1H), 7.18–7.26(m, 2H), 7.72(s,1H), 8.52(bs,1H).

Alternatively the title compound was prepared by the following procedure:

B) 3-(1-Benzyloxycarbonylpyrrolidin-2(R)-ylmethyl)-5-bromo-1H-indole (see Preparation 35B) (5.00 g, 12.10 mmol) was dissolved in dichloromethane and the resulting solution was added dropwise to a stirred mixture of borontrifluoride.etherate (17.15 g, 14.9 ml, 12.1 mmol) and ethane thiol (21.4 g, 25.5 ml, 344 mmol) at room temperature under nitrogen. After 68 hours the reaction mixture was added by pipette to a 10% aqueous sodium carbonate solution (500 ml) and extracted with ethyl acetate (3×400 ml). The combined organic extract was dried (Na$_2$SO$_4$) and the solvent evaporated under reduced pressure. Purification by column chromatography on silica gel, eluting with dichloromethane:methanol:0.880 aqueous ammonia (90:10:1), yielded the title compound as a foam (2.1 g). Found: C,55.04; H,5.29; N,9.83. $C_{13}H_{15}BrN_2 \cdot 3/50 CH_2Cl_2$ requires: C,55.10; H,5.35; N,9.83%.

[α]$_D^{25}$=–12° (c=0.1 in methanol).

$^1$H-N.M.R. (CDCl$_3$): δ=1.38–1.50(m,1H), 1.68–1,98(m, 3H), 2.32(bs,1H), 2.76–2.90(m,3H), 3.00–3.10(m,1H), 3.32–3.41 (m,1H), 5.30(s,3/25H), 7.06(s,1H), 7.22–7.30(m, 2H), 7.75(s,1H), 8.37(bs,1H).

PREPARATION 56

5-Bromo-3-(1-cyclopropylmethylpyrrolidin-2(R)-ylmethyl)-1H-indole

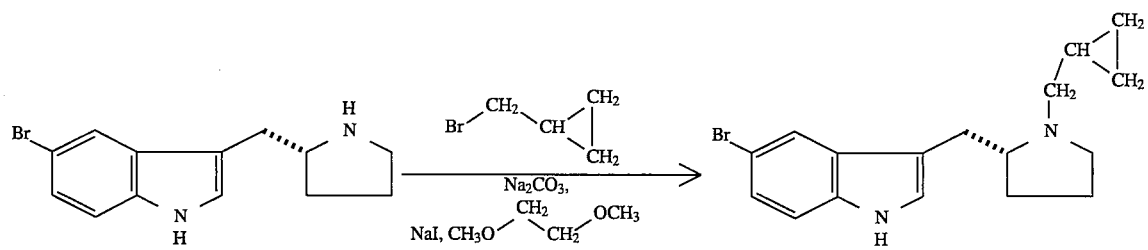

5-Bromo-3-(pyrrolidin-2(R)-ylmethyl)-1H-indole (1.84 g, 6.3 mmol) (see Preparation 55), cyclopropylmethyl bromide (0.67 ml, 6.9 mmol), sodium carbonate (0.73 g, 6.9 mmol) and sodium iodide (1.0 g, 6.7 mmol) in 1,2-dimethoxyethane (10 ml) was refluxed under nitrogen for 14 hours. After cooling to room temperature the reaction mixture was partitioned between ethyl acetate and aqueous sodium carbonate. The organic phase was washed with more aqueous sodium carbonate, dried ($Na_2SO_4$) and the solvent evaporated under reduced pressure. The residue was purified by column chromatography on silica gel, eluting with dichloromethane/methanol/ammonium hydroxide (90:10:0.05) to yield the title compound as a foam (2.09 g). Found: C,61.22; H,6.40; N,8.39. $C_{17}H_{21}BrN_2$ requires: C,61.26; H,6.35; N,8.41%.

$[\alpha]_D^{25}=+72°$ (c=0.1 in methanol).

$^1$H-N.M.R. ($CDCl_3$): δ=0.12–0.20(m,2H), 0.50–0.58(m, 2H), 0.92–1.08(m,1H), 1.50–1.92(m,4H), 1.98–2.08(m,1H), 2.20–2.30(m,1H), 2.55–2.68(m,2H), 2.90–2.98(m,1H), 3.08–3.18(m,1H), 3.38–3.50(m,1H) 7.04(s,1H), 7.20–7.28(m,2H), 7.70(s,1H), 8.10(bs,1H).

PREPARATION 57

5-Bromo-3-[1-(2-methoxyethyl)pyrrolidin-2(R)-ylmethyl]-1H-indole

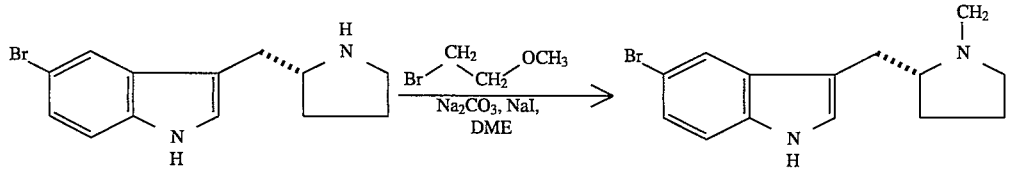

5-Bromo-3-(pyrrolidin-2(R)-ylmethyl)-1H-indole (3.20 g, 11.5 mmol) (see Preparation 55), 1-bromo-2-methyoxyethane (1.67 g, 1.13 ml, 12.1 mmol), sodium carbonate (1.34 g, 12.6 mmol) and sodium iodide (1.89 g, 12.6 mmol) in 1,2-dimethoxyethane (75 ml) was refluxed for 16 hours under nitrogen. The reaction mixture was then concentrated under reduced pressure to a volume of about 20 ml. The resulting slurry was partitioned between ethyl acetate and aqueous sodium carbonate. The organic phase was dried ($Na_2SO_4$) and the solvent evaporated under reduced pressure. The residue was purified by column chromatography on silica gel, eluting with dichloromethane/methanol/ammonium hydroxide (89:10:1) to yield, after combination and evaporation of the appropriate fractions, the title compound. Found: C,57.25; H,6.41; N,8.14. $C_{16}H_{21}BrN_2O$ requires: C,56.98; H,6.28; N,8.31.

$^1$H-N.M.R. ($CDCl_3$): δ=1.50–1.85(m,4H), 2.15–2.30(m, 1H), 2.40–2.50 (m,1H), 2.50–2.75(m,2H), 3.08–3.15(m, 1H), 3.15–3.30(m,2H), 3.40(s,3H), 3.55–3.65(m,2H), 7.03(s,1H), 7.15–7.30(m, integral obscured by solvent), 7.70(s,1H), 8.00(bs,1H).

PREPARATION 58

5-Bromo-3-(1-methylpyrrolidin-2(R)-ylmethyl)-1-triisopropylsilylindole

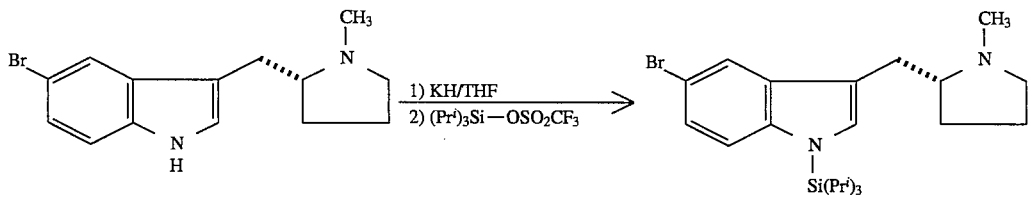

To a suspension of potassium hydride (309 mg of a 30% KH suspension in mineral oil, 2.70 mmol) in tetrahydrofuran (12.0 ml) at 0° C. under nitrogen, was added dropwise a solution of 5-bromo-3-(1-methylpyrrolidin-2(R)-ylmethyl)-1H-indole (528 mg, 1.80 mmol) (see Preparation 36) in tetrahydrofuran (3.0 ml). The ice-bath was removed and the reaction allowed to warm to room temperature with stirring, over 30 minutes. The reaction was cooled back down to 0° C. and triisopropyltriflate (0.761 ml, 2.7 mmol) was then added dropwise. The reaction was stirred for a further 30 minutes during which time the solution was allowed to warm to room temperature. The reaction mixture was then partitioned between ethyl acetate and aqueous sodium carbonate. The organic layer was separated and the aqueous phase reextracted with ethyl acetate. The combined organic phases were dried ($Na_2SO_4$) and the solvent removed under reduced pressure. The residue was purified by column chromatography on silica gel, eluting with ethyl acetate/ diethylamine (98:2), to give, after combination and evaporation of the appropriate fractions, the title compound as an oil (670 mg). Found: C,62.11; H,8.61; N,6.17. $C_{23}H_{37}N_2BrSi$ requires: C,61.45; H,8.30; N,6.23%.

$^1$H-N.M.R. ($CDCl_3$): δ=1.10(d,18H), 1.40–1.85(m,7H), 2.18–2.25(m,1H), 2.38–2.60(m,2H), 2.40(s,3H), 3.05–3.20(m,2H), 7.00(s,1H), 7.20(d,1H), 7.30(d,1H), 7.62(s,1H).

PREPARATION 59

3-(1-methylpyrrolidin-2(R)-ylmethyl)-5-(tri-n-butylstannyl)-1-triisopropylsilylindole

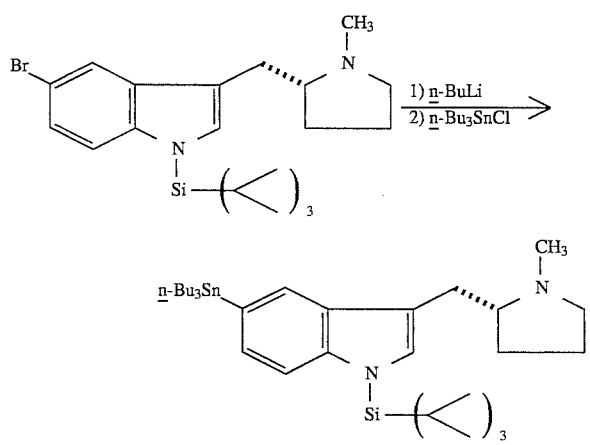

n-ButylLithium (7.80 ml of a 2.5M solution in hexanes, 19.49 ml) was added dropwise to a solution of 5-bromo-3-(1-methylpyrrolidin-2(R)-ylmethyl)-1-triisopropylsilylindole (6.28 g, 13.97 mmol) (Preparation 58) in tetrahydrofuran (430 ml) at −78° C. The reaction was then stirred at −70° C. for ½ hour whereupon tri-n-butylstannylchloride (3.97 ml, 4.64 mmol) was added and the reaction stirred at −70° C. for 20 minutes. The reaction was then warmed to room temperature and 14.4 ml of water was added and the resulting solution partitioned (97½:2½) to afford, after combination and evaporation of the appropriate fractions, the title compound as an oil. Found: C,70.29; H,8.72; N,8.17. $C_{30}H_{43}N_3O_2Si \cdot \frac{1}{8}CH_2Cl_2$ requires: C,70.07; H,8.44; N,8.14%.

$^1$H-N.M.R. ($CDCl_3$): δ=1.10(d,18H), 1.52–1.90(m,7H), 2.18–2.28(m,1H), 2.40–2.55(m,1H), 2.50(s,3H), 2.60–2.75(m,1H), 3.08–3.30(m,2H), 4.02(s,3H), 5.25(s,¼H), 7.10(s,1H), 7.55(d,1H), 7.80–8.02(m,4H), 8.20(s,1H).

PREPARATION 60

5-(6-Methoycarbonyl-2-pyridyl)-3-(1-methylpyrrolidin-2(R)-ylmethyl)-1-triisopropylsilylindole

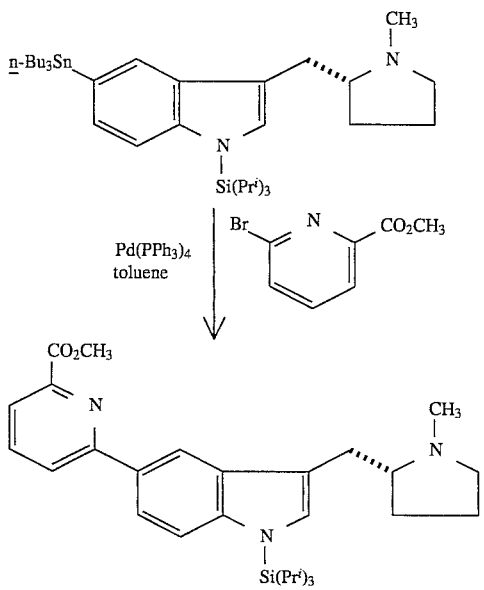

3-(1-methylpyrrolidin-2(R)-ylmethyl)-5-(tri-n-butylstannyl)-1-triisopropylsilylindole (500 mg, 0.910 mmol) (see Preparation 59), 2-bromo-6-methoxycarbonylpyridine (197 mg, 0.910 mmol) and tetrakistriphenylphosphinepalladium(O) ($Pd(PPh_3)_4$) were reacted in refluxing toluene (8.0 ml), under nitrogen, for 16 hours. The solvent was then removed under reduced pressure and the residue purified by column chromatography on silica gel, eluting with ethyl acetate/diethylamine between aqueous sodium carbonate and ethyl acetate. The organic layer was dried ($Na_2SO_4$) and the solvent removed under reduced pressure. The residue was purified by column chromatography, eluting with dichloromethane:methanol:ammonium hydroxide (94.5:5:0.5) to give the title compound as a viscous oil. Found: C,63.90; H,9.56; N,4.13. $C_{35}H_{64}N_2Sisn$ requires: C,63.72; H,9.78; N,4.25%.

$^1$H-N.M.R. (CDCl3): δ=0.90(t,9H), 1.00–1.20(m,24H), 1.40–1.90(m,13H), 2.15–2.30(m,1H), 2.48(s,3H), 2.40–2.70(m,2H), 3.15–3.30(m,2H), 7.00(s,1H), 7.20(d,1H), 7.45(d,1H), 7.65(s,1H).

PREPARATION 61

5-(5-Carbamoyl-2-thienyl)-3-(1-methylpyrrolidin-2(R)-ylmethyl)-1-triisooropylsilylindole

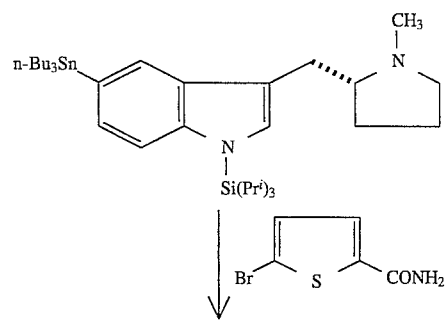

-continued

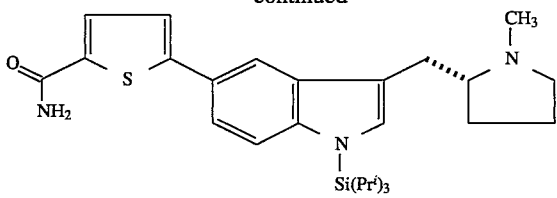

3-(1-methylpyrrolidin-2(R)-ylmethyl)-5-(tri-n-butylstannyl)-1-triisopropylsilylindole (see Preparation 59) was reacted with 2-bromo-5-carbamoylthiophene in the presence of telirakistriphenylphosphinepalladium(O), in toluene, using a procedure similar to that described in Preparation 60. This gave the title compound. Found: C,65.18; H,8.10; N,8.24. $C_{28}H_{41}N_3OSSi.^{5}/_{16}CH_2Cl_2$ requires: C,155.10; H,8.03; N,8.04%.

$^1$H-N.M.R. (CDCl$_3$): δ=1.10(d,18H), 1.45–1.90(m,7H), 2.25–2.35(m,1H), 2.55(s,3H), 2.50–2.70(m,2H), 3.15–3.30(m,2H), 5.30(s,⅝H), 7.10(s,1H), 7.25–7.30(m, integral obscured by solvent), 7.4.0–7.55(m,3H), 7.85(s, 1H).

PREPARATION 62

5-(5-Methoxycarbonyl-2-furyl)-3-(1-methylpyrrolidin-2(R)-ylmethyl)-1-triisopropylsilylindole

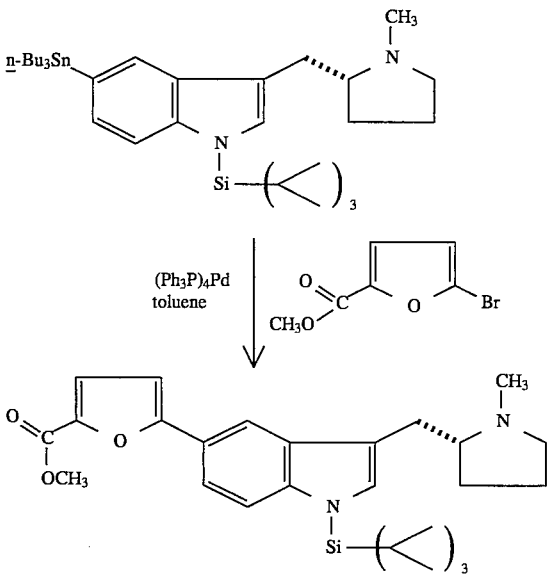

3-(1-methylpyrrolidin-2(R)-ylmethyl)-5-(tri-n-butylstannyl)-1-triisopropylsilylindole (see Preparation 59) was reacted with 2-bromo-5-metlhoxycarbonylfuran in the presence of tetrakistriphenylphosphinepalladium(O), in toluene, using a procedure similar to that described in Preparation 60. This gave the title compound. Found: C,68.21; H,8.55; N,5.84. $C_{29}H_{42}N_2O_3Si.^{5}/_{24}CH_2Cl_2$ requires: C,68,46; H,8.34; N,5.47%.

$^1$H-N.M.R.: δ=1.10(d,18H), 1.40–1.85(m,7H), 2.15–2.25(m,1H), 2.50(s,3H), 2.50–2.70(m,2H), 3.05–3.40(m,2H), 3.95(s,3H), 5.30(s,⁵/₁₂H), 6.70(d,1H), 7.10(s,1H), 7.15–7.25(m, integral obscured by solvent), 7.50(d,1H), 7.60(d,1H), 8.00(s,1H).

We claim:

1. A compound of formula (I):

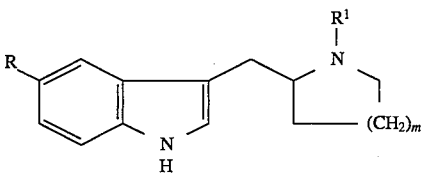

or a pharmaceutically acceptable salt thereof, wherein

R is phenyl, pyridinyl, pyridazinyl, pyrimidinyl, pyrazinyl, furyl or thienyl, all of which may be optionally substituted by halo, $C_1$–$C_4$ alkyl, $C_1$–$C_4$ alkoxy or a group of the formula:

—X—R$^2$;

R$^1$ is H, $C_1$–$C_6$ alkyl, $C_3$–$C_7$ cycloalkyl, $C_5$–$C_7$ cycloalkenyl, $C_3$–$C_6$ alkenyl or $C_3$–$C_6$ alkynyl, said alkyl group being optionally substituted by $C_3$–$C_7$ cycloalkyl, $C_3$–$C_7$ cycloalkyloxy, OH, $C_1$–$C_6$ alkoxy, CONR$^3$R$^4$, SO$_2$NR$^3$R$^4$, COR$^5$, SOR$^5$, SO$_2$R$^5$, CO$_2$R$^6$, aryl, aryloxy, aryl($C_1$–$C_6$)alkoxy or heteroaryl, said alkenyl group being optionally substituted by aryl and said cycloalkyl group being optionally substituted by OH; the cycloalkyl and cycloalkenyl groups of the foregoing groups being optionally linked to the N-atom by a $C_1$–$C_2$ alkylene moiety;

R$^2$ is COR$^7$, CO$_2$R$^7$, SOR$^7$, SO$_2$R$^7$, CONR$^3$R$^4$, SO$_2$NR$^3$R$^4$, NHCOR$^7$, NHCONR$^3$R$^4$, NHSO$_2$R$^7$, NHSO$_2$NR$^3$R$^4$, OH or CN,

R$^3$ and R$^4$ are either each independently selected from H, $C_3$–$C_7$ cycloalkyl and $C_1$–$C_6$ alkyl, said alkyl group being optionally substituted by $C_3$–$C_7$ cycloalkyl or aryl, or R$^3$ and R$^4$ taken together represent $C_3$–$C_6$ alkylene optionally interrupted by O, S(O)$_n$, NH or N($C_1$–$C_6$ alkyl);

R$^5$ is $C_1$–$C_6$ alkyl, $C_3$–$C_7$ cycloalkyl, $C_3$–$C_7$ cycloalkyl($C_1$–$C_6$)alkylene, aryl($C_1$–$C_6$)alkylene or aryl; R$^6$ is $C_1$–$C_6$ alkyl, $C_3$–$C_7$ cycloalkyl or aryl($C_1$–$C_6$)alkylene;

R$^7$ is $C_1$–$C_6$ alkyl;

X is a direct link or $C_1$–$C_7$ alkylene;

m is 1 or 2;

n is 0, 1 or 2; "aryl", when used in the definitions of R$^1$, R$^3$, R$^4$, R$^5$ and R$^6$, means phenyl optionally substituted by $C_1$–$C_6$ alkyl, $C_1$–$C_6$ alkoxy or halo; and "heteroaryl", used in the definition of R$^1$, means pyridinyl, pyrimidinyl, pyrazinyl, furyl, thienyl, pyrrolyl, thiazolyl or oxazolyl.

2. A compound as claimed in claim 1 wherein R is phenyl, pyridinyl, pyrimidinyl, thienyl or furyl, each optionally substituted by a group of the formula

—X—R$^2$;

R$^1$ is H, $C_1$–$C_6$ alkyl, $C_1$–$C_4$ alkoxy($C_1$–$C_6$)alkylene, R$^3$R$^4$NCO($C_1$–$C_6$)alkylene; or $C_3$–$C_6$ cycloalkyl($C_1$–$C_4$)alkylene.

R$^2$ is COR$^7$, CO$_2$R$^7$, SOR$^7$, SO$_2$R$^7$, CONR$^3$R$^4$, SO$_2$NR$^3$R$^4$, NHSO$_2$R$^7$, CN or OH;

R$^3$ and R$^4$ are either each independently selected from H and $C_1$–$C_4$ alkyl, or R$^3$ and R$^4$ taken together represent $C_3$–$C_6$ alkylene interrupted by O;

R$^7$ is methyl, ethyl or n-propyl;

X is a direct link or methylene; and is 1.

3. A compound as claimed in claim 1 wherein R is phenyl optionally substituted at the 3- or 4-position, or 2-, 3- or 4-pyridinyl optionally substituted at the 5- or 6-position, both optionally substituted with sulphamoyl, N,N-dimethylsulphamoyl, carbamoyl, N-methylcarbamoyl, N,N-dimethylcarbamoyl, morpholinocarbonyl, methyl- or ethyl- or n-propyl-sulphonyl or -sulphinyl, methyl- or ethyl-sulphonylmethyl, acetyl, hydroxymethyl, methoxycarbonyl, ethanesulphonamidomethyl, cyano, carbamoylmethyl, 1-hydroxyprop-2-yl, N,N-dimethylcarbamoylmethyl, ethylcarbamoyl, dimethylcarbamoyl or methoxycarbonyl; $R^1$ is hydrogen, methyl, ethyl, 2-methoxyethyl, cyclopropylmethyl, benzyloxycarbonyl, 2-carbamoylethyl, 2-dimethylcarbamoylethyl; and m is 1.

4. A compound as claimed in claim 1 having the R-configuration at the 2-position of the pyrrolidine or piperidine ring.

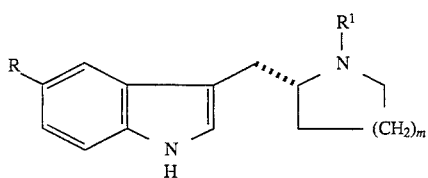

5. A compound as claimed in claim 1 that is selected from the group:.

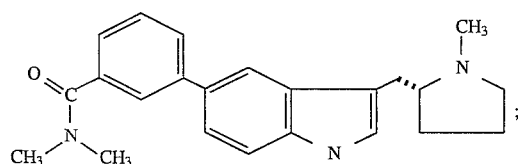

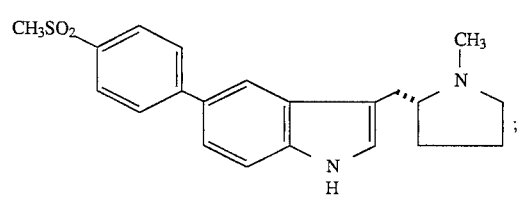

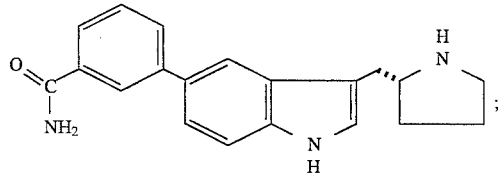

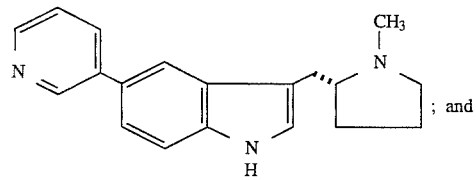

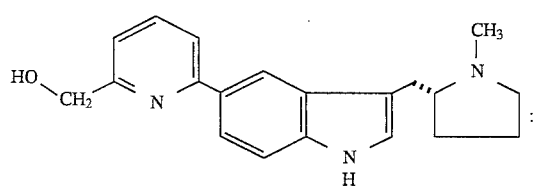

or a pharmaceutically acceptable salt thereof.

6. A compound having the formula:

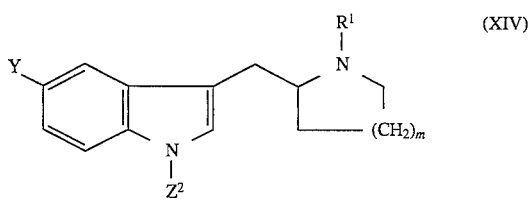

and useful as an intermediate to prepare the compounds claimed in claim 1, and wherein $R^1$ is as defined in claim 1 or is a protecting group $Z^1$ where $Z^1$ is an arylalkoxycarbonyl, benzyloxycarbonyl or alkoxycarbonyl group;

Y is $(alkyl)_3Sn$—; $(alkyl)_2B$—; $(HO)_2B$—; $(alkoxy)_2B$—; Li—; Cu—; chloroZn—; haloMg—; arylHg— or chloroHg—; and $Z^2$ is a trialkylsilyl or alkoxycarbonyl group.

7. A pharmaceutical composition comprising a compound of formula (I), or a pharmaceutically acceptable salt thereof, as claimed in claim 1, together with a pharmaceutically acceptable diluent or carrier.

8. A method for treating a condition selected from migraine or an associated condition such as cluster headache, chronic paroxysmal hemicrania or headache associated with a vascular disorder, or depression, anxiety, an eating disorder, obesity or drug abuse, which comprises treating said human being with an effective amount of a compound of formula (I), or a pharmaceutically acceptable salt thereof, or a pharmaceutical composition containing either entity, as claimed in claim 1.

9. A method for treating a condition selected from a medical condition for which a selective agonist of $5\text{-HT}_1$-like receptors is indicated, which comprises treating said human being with an effective amount of a compound of formula (I), or a pharmaceutically acceptable salt thereof, or a pharmaceutical composition containing either entity, as claimed in claim 1.

10. A compound of the formula

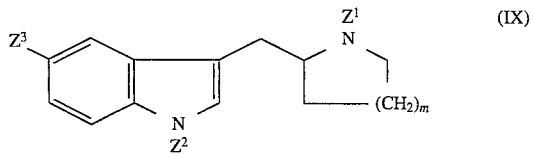

wherein $Z^1$ is a suitable protecting group; $Z^2$ is hydrogen or a suitable indole N-protecting group; $Z^3$ is phenyl, pyridinyl, pyridazinyl, pyrimidinyl, pyrazinyl, furyl or thienyl, all of which may be optionally substituted by halo, $C_1$–$C_4$ alkyl, $C_1$–$C_4$ alkoxy, a group of the formula:

—X—$R^2$, or $Z^3$ is a metal-containing moiety suitable for a cross-coupling reaction; and m is 1 or 2.

11. A compound as claimed in claim 10, wherein $Z^1$ is —$COOR^8$; $Z^2$ is an alkoxycarbonyl group or a trialkylsilyl group; $Z^3$ is $(alkyl)_3Sn$—, $(alkyl)_2B$—, $(HO)_2B$—, $(alkoxy)_2B$—, Li—, Cu—, chloroZn—, haloMg—, arylHg—, or chloroHg—; and $R^8$ is t-butyl or benzyl.

* * * * *